(12) United States Patent
Wood et al.

(10) Patent No.: US 11,654,146 B2
(45) Date of Patent: May 23, 2023

(54) METHODS FOR KILLING ANTIBIOTIC TOLERANT BACTERIA

(71) Applicant: THE PENN STATE RESEARCH FOUNDATION, University Park, PA (US)

(72) Inventors: Thomas Keith Wood, Port Matilda, PA (US); Sooyeon Song, Gwangju (KR)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 17/337,097

(22) Filed: Jun. 2, 2021

(65) Prior Publication Data

US 2021/0401843 A1 Dec. 30, 2021

Related U.S. Application Data

(60) Provisional application No. 63/033,544, filed on Jun. 2, 2020.

(51) Int. Cl.
*A61K 31/519* (2006.01)
*A61K 45/06* (2006.01)
*A61P 31/04* (2006.01)
*A61K 31/4045* (2006.01)

(52) U.S. Cl.
CPC ........ *A61K 31/519* (2013.01); *A61K 31/4045* (2013.01); *A61K 45/06* (2013.01); *A61P 31/04* (2018.01)

(58) Field of Classification Search
CPC .... A61K 31/519; A61K 31/4045; A61P 31/04
See application file for complete search history.

(56) References Cited

PUBLICATIONS

Antonoplis et al., A Dual-Function Antibiotic-Transporter Conjugate Exhibits Superior Activity in Sterilizing MRSA Biofilms and Killing Persister Cells, Journal of the American Chemical Society, 2018, 140(47):16140-16151.
Aizenman et al., An *Escherichia coli* Chromosomal "Addiction Module" Regulated by 3', 5'-Bispyrophosphate: A Model for Programmed Bacterial Cell Death, Proceedings of the National Academy of Sciences, 1996, 93(12):6059-6063.
Baba et al., Construction of *Escherichia coli* K-12 In-Frame, Single-Gene Knockout Mutants: The Keio Collection, Molecular Systems Biology, 2006, Article No. 2006-0008, 11 pages.
Bertani et al., Studies on Lysogenesis, I. The Mode of Phage Liberation by Lysogenic *Escherichia coli*, Journal of Bacteriology, 1951, 62(3):293-300.
Bigger, Treatment of Staphylococcal Infections with Penicillin by Intermittent Sterilisation, The Lancet, 1944, 244(6320):497-500.
Burger et al., Chemotherapeutic Drugs Inhibit Ribosome Biogenesis at Various Levels, Journal of Biological Chemistry, 2010, 285(16):12416-12425.
Chen et al., Structural Insight into the Oxidation-Sensing Mechanism of the Antibiotic Resistance of Regulator MexR, EMBO Reports, 2010, 11(9):685-690.
Cheverton et al., A *Salmonella* Toxin Promotes Persister Formation through Acetylation of tRNA, Molecular Cell, 2016, 63(1):86-96.
Chimerel et al., Indole Prevents *Escherichia coli* Cell Division by Modulating Membrane Potential, Biochimica et Biophysica Acta, 2012, 1818(7):1590-1594.
Chowdhury et al., Persistence Increases in the Absence of the Alarmone Guanosine Tetraphosphate by Reducing Cell Growth, Scientific Reports, 2016, 6:20519, 9 pages.
Chowdhury et al., DNA-Crosslinker Cisplatin Eradicates Bacterial Persister Cells, Biotechnology and Bioengineering, 2016, 113(9):1984-1992.
Conlon et al., Activated ClpP Kills Persisters and Eradicates a Chronic Biofilm Infection, Nature, 2013, 503(7476):365-370.
Cruz-Muniz et al., Repurposing the Anticancer Drug Mitomycin C for the Treatment of Persistent Acinetobacter Baumannii Infections, International Journal of Antimicrobial Agents, 2017, 49(1):88-92.
Cui et al., Identification of Genes Involved in Bacteriostatic Antibiotic-Induced Persister Formation, Frontiers in Microbiology, 2018, vol. 9, Article 413, 10 pages.
Defraine et al., Fighting Bacterial Persistence: Current and Emerging Anti-Persister Strategies and Therapeutics, Drug Resistance Updates, 2018, 38:12-26.
Deleon et al., Synergistic Interactions of Pseudomonas Aeruginosa and *Staphylococcus aureus* in an In Vitro Wound Model, Infection and Immunity, 2014, 82(11):4718-4728.
Donegan et al., Evaluation of Methods for Sampling, Recovery, and Enumeration of Bacteria Applied to the Phylloplane, Applied and Environmental Microbiology, 1991, 57(1):51-56.
Dorr et al., Ciprofloxacin Causes Persister Formation by Inducing the TisB Toxin in *Escherichia coli*, PLoS Biology, 2010, 8(2):e1000317, 8 pages.
Gogol et al., Small RNAs Endow a Transcriptional Activator with Essential Repressor Functions for Single-Tier Control of a Global Stress Regulon, Proceedings of the National Academy of Sciences, 2011, 108(31):12875-12880.
Grassi et al., Generation of Persister Cells of Pseudomonas Aeruginosa and *Staphylococcus aureus* by Chemical Treatment and Evaluation of Their Susceptibility to Membrane-Targeting Agents, Frontiers in Microbiology, 2017, vol. 8, Article 1917, 12 pages.
Gutgsell et al., The Pseudouridine Synthase RluD is Required for Normal Ribosome Assembly and Function in *Escherichia coli*, RNA, 2005, 11(7):1141-1152.
Guyer et al., Identification of a Sex-Factor-Affinity Site in *E. coli* as γδ, Cold Spring Harbor Symposia on Quantitative Biology, 1981, 45:135-140.
Harrison et al., The Chromosomal Toxin Gene yafQ is a Determinant of Multidrug Tolerance for *Escherichia coli* Growing in a Biofilm, Antimicrobial Agents and Chemotherapy, 2009, 53(6):2253-2258.
Hobbs et al., Small RNAs and Small Proteins Involved in Resistance to Cell Envelope Stress and Acid Shock in *Escherichia coli*: Analysis of a Bar-Coded Mutant Collection, Journal of Bacteriology, 2010, 192(1):59-67.

(Continued)

*Primary Examiner* — Sahar Javanmard
(74) *Attorney, Agent, or Firm* — Quarles & Brady LLP

(57) ABSTRACT

Disclosed herein are compounds, compositions, and methods for treating infections by bacteria and for killing bacteria. In particular, the disclosed compounds, compositions, and methods are useful for treating infections by bacteria and for killing persister bacteria that survive antibiotic treatment and then reconstitute infections.

17 Claims, 26 Drawing Sheets

(56) References Cited

PUBLICATIONS

Hobby et al., Observations on the Mechanism of Action of Penicillin, Proceedings of the Society for Experimental Biology and Medicine, 1942, 50(2):281-285.

Hu et al., Toxin YafQ Increases Persister Cell Formation by Reducing Indole Signalling, Environmental Microbiology, 2015, 17(4):1275-1285.

Kim et al., Toxins Hha and CspD and Small RNA Regulator Hfq are Involved in Persister Cell Formation through MqsR in *Escherichia coli*. Biochemical and Biophysical Research Communications, 2010, 391(1):209-213.

Kim et al., Persistent Persister Misperceptions, Frontiers in Microbiology, 2016, vol. 7, Article 2134, pp. 1-7.

Kim et al., Tolerant, Growing Cells from Nutrient Shifts are not Persister Cells, MBio, 2017, 8(2):e00354-17, 5 pages.

Kim et al., Viable but Non-Culturable and Persistence Describe the Same Bacterial Stress State, Environmental Microbiology, 2018, 20(6):2038-2048.

Kim et al., Single Cell Observations Show Persister Cells Wake Based on Ribosome Content, Environmental Microbiology, 2018, 20(6):2085-2098.

Kim et al., A New Class of Synthetic Retinoid Antibiotics Effective Against Bacterial Persisters, Nature, 2018, 556(7699):103-107.

Kitagawa et al., Complete Set of ORF Clones of *Escherichia coli* ASKA Library (A Complete Set of *E. coli* K-12 ORF Archive): Unique Resources for Biological Research, DNA Research, 2005, 12(5):291-299.

Kwan et al., Combatting Bacterial Infections by Killing Persister Cells with Mitomycin C, Environmental Microbiology, 2015, 17(11):4406-4414.

Kwan et al., Phosphodiesterase DosP Increases Persistence by Reducing cAMP which Reduces the Signal Indole, Biotechnology and Bioengineering, 2015, 112(3):588-600.

Kwan et al., Arrested Protein Synthesis Increases Persister-Like Cell Formation, Antimicrobial Agents and Chemotherapy, 2013, 57(3):1468-1473.

Lee et al., Halogenated Indoles Eradicate Bacterial Persister Cells and Biofilms, AMB Express, 2016, 6:123, 12 pages.

Liberati et al., An Ordered, Nonredundant Library of Pseudomonas Aeruginosa Strain PA14 Transposon Insertion Mutants, Proceedings of the National Academy of Sciences, 2006, 103(8):2833-2838.

Lu et al., Reverse Transcription of 16S rRNA to Monitor Ribosome-Synthesizing Bacterial Populations in the Environment, Applied and Environmental Microbiology, 2009, 75(13):4589-4598.

Luidalepp et al., Age of Inoculum Strongly Influences Persister Frequency and Can Mask Effects of Mutations Implicated in Altered Persistence, Journal of Bacteriology, 2011, 193(14):3598-3605.

Narayanaswamy et al., Novel Glycopolymer Eradicates Antibiotic- and CCCP-Induced Persister Cells in Pseudomonas Aeruginosa, Frontiers in Microbiology, 2018, vol. 9, Article 1724, 12 pages.

Piques et al., Ribosome and Transcript Copy Numbers, Polysome Occupancy and Enzyme Dynamics in *Arabidopsis*, Molecular Systems Biology, 2009, vol. 5, Article 314, 17 pages.

Pu et al., ATP-Dependent Dynamic Protein Aggregation Regulates Bacterial Dormancy Depth Critical for Antibiotic Tolerance, Molecular Cell, 2019, 73(1):143-156.

Ronneau et al., Clarifying the Link Between Toxin-Antitoxin Modules and Bacterial Persistence, Journal of Molecular Biology, 2019, 431(18):3462-3471.

Shah et al., Persisters: A Distinct Physiological State of *E. coli*, BMC Microbiology, 2006, 6:53, 9 pages.

Song et al., Post-Segregational Killing and Phage Inhibition are Not Mediated by Cell Death through Toxin/Antitoxin Systems, Frontiers in Microbiology, 2018, vol. 9, Article 814, 6 pages.

Song et al., Identification of a Potent Indigoid Persister Antimicrobial by Screening Dormant Cells, Biotechnology and Bioengineering, 2019, 116(9):2263-2274.

Song et al., ppGpp Ribosome Dimerization Model for Bacterial Persister Formation and Resuscitation, Biochemical and Biophysical Research Communications, 2020, 523(2):281-286.

Sulaiman et al., Specific Enrichment and Proteomics Analysis of *Escherichia coli* Persisters from Rifampin Pretreatment, Journal of Proteome Research, 2018, 17(11):3984-3996.

Sun et al., In Vitro Multispecies Lubbock Chronic Wound Biofilm Model, Wound Repair and Regeneration, 2008, 16(6):805-813.

Tkhilaishvili et al., Bacteriophage Sb-1 Enhances Antibiotic Activity Against Biofilm, Degrades Exopolysaccharide Matrix and Targets Persisters of *Staphylococcus aureus*, International Journal of Antimicrobial Agents, 2018, 52(6):842-853.

Van Den Bergh et al., Formation, Physiology, Ecology, Evolution and Clinical Importance of Bacterial Persisters, FEMS Microbiology Reviews, 2017, 41(3):219-251.

Wang et al., Antitoxin MqsA Helps Mediate the Bacterial General Stress Response, Nature Chemical Biology, 2011, 7(6):359-366.

Wang et al., Toxin-Antitoxin Systems Influence Biofilm and Persister Cell Formation and the General Stress Response. Applied and Environmental Microbiology, 2011, 77(16):5577-5583.

Wood, Combatting Bacterial Persister Cells, Biotechnology and Bioengineering, 2016, 113(3):476-483.

Wood et al., Ribosome Dependence of Persister Cell Formation and Resuscitation, Journal of Microbiology, 2019, 57(3):213-219.

Yamasaki et al., Persister Cells Resuscitate Using Membrane Sensors that Activate Chemotaxis, Lower cAMP Levels, and Revive Ribosomes. iScience, 2020, 23(1):100792, 66 pages.

Yang et al., Amphiphilic Indole Derivatives as Antimycobacterial Agents: Structure-Activity Relationships and Membrane Targeting Properties, Journal of Medicinal Chemistry, 2017, 60(7):2745-2763.

Yuan et al., Repurposing the Anticancer Drug Cisplatin with the Aim of Developing Novel *Pseudomonas aeruginosa* Infection Control Agents, Beilstein Journal of Organic Chemistry, 2018, 14(1):3059-3069.

METHODS FOR KILLING ANTIBIOTIC TOLERANT BACTERIA

CROSS-REFERENCE TO RELATED APPLICATIONS

This application claims the benefit of priority under 35 U.S.C. § 119(e) to U.S. Provisional Application No. 63/033,544, filed Jun. 2, 2020, the content of which is incorporated herein by reference in its entirety

BACKGROUND

The field of the invention relates to compounds, compositions, and methods for reduction and eradication of persister cells in a bacterial population. More specifically, the field of the invention relates to compounds, compositions, and methods for treating bacterial infections.

Bacterial "persister cells" are pathogenic and nonpathogenic bacteria that neither grow nor die in the presence of microbicidal antibiotics. As such, persister cells contribute to the recalcitrance of treatment of clinical infections by reconstituting infections. Persister cells arise due to metabolic inactivity. (See K. Lewis, Nat. Rev. Microbiol. 5, 48 (2007); Kwan, et al. Antimicrob. Agents Chemother. 57, 1468 (2013); and T. K. Wood, et al., Appl. Environ. Microbiol. 79, 7116 (2013)). Persister cells are highly tolerant to all traditional antibiotics, which are primarily effective against actively growing cells, as well as tolerant to other stresses such as lack of nutrients, oxidizing agents, acids, bases, and temperature extremes.

Bacterial persistence is a non-hereditary phenotype that may occur stochastically or through environmental influence in a small sub-population of all tested bacterial species. (See W. Bigger, Lancet 244, 497 (1944); N. Q. Balaban, et al., Science 305, 1622 (2004); Kwan, et al. (2013), N. Moker, et al., J. Bacteriol. 192, 1946 (2010); Y. Hu, et al., Environ. Microbiol., 17, 1275, (2015); T. Dorr, et al. PLoS Biol. 8, e1000317 (2010); and N. M. Vega, et al., Nat. Chem. Biol. 8, 431 (2012); and K. Lewis, Curr. Top. Microbiol. Immunol. 322, 107 (2008)). Few distinctly new antibiotics have been discovered recently. (See T. J. Dougherty, M. J. Pucci, Eds., (Springer, New York, N.Y., 2012). Worse, current antibiotics are ineffective against persister cells. Thus, there is an ongoing and unmet need for improved approaches to treating infections that comprise persister cells. The present disclosure meets this need.

SUMMARY

Disclosed herein are compounds, compositions, and methods for treating infections by bacteria and for killing bacteria. In particular, the disclosed compounds, compositions, and methods are useful for treating infections by bacteria and for killing persister bacteria that survive antibiotic treatment and then reconstitute infections.

The disclosed compounds, compositions, and methods may be utilized for reducing and/or eradicating bacterial persister cells and/or dormant "viable but non-culturable" (VBNC) cells. The disclosed methods typically comprise administering the disclosed compounds or compositions comprising the disclosed compounds to a bacterial population comprising bacterial persister cells and/or dormant VBNC cells where preferably the bacterial persister cells and/or the VBNC cells of the bacterial population are killed, reduced, and/or eradicated. The disclosed compounds for use in the disclosed compositions and methods may include, but are not limited to [(5-nitro-3-phenyl-1H-indol-2-yl)methyl]amine and salts thereof such as [(5-nitro-3-phenyl-1H-indol-2-yl)methyl]amine hydrochloride (NPIMA), and 2-{[2-(4-bromophenyl)-2-oxoethyl]thio}-3-ethyl-5,6,7,8-tetrahydro[1]benzothieno[2,3-d]pyrimidin-4(3H)-one (BPOET) or salts thereof.

The disclosed compounds, compositions, and methods may be utilized for killing, reducing, and/or eradicating bacteria of a variety of types, including Gram-negative and Gram-positive pathogenic bacteria. In certain approaches, the bacteria are pathogenic and/or are selected from *Escherichia* spp. such as enterohemorrhagic *E. coli*, *Staphylococcus* spp. such as *S. aureus*, and *Pseudomonas* spp. such as *Pseudomonas aeruginosa*.

The disclosed compounds, compositions, and methods may be utilized for killing, reducing, and/or eradicating bacteria from a wound of an individual, optionally wherein the wound comprises bacteria that are resistant to one or more antibiotics. Optionally, the individual may have been previously been diagnosed with a bacterial infection and treated with at least one antibiotic, for example, where the bacterial infection was not cleared by such previous treatment.

In the disclosed methods, the bacterial population may be present in a liquid biological sample or liquid environment. In some embodiments of the disclosed methods, the bacterial population is present in suspension.

The disclosed compounds, compositions, and methods may be utilized for killing, reducing, and/or eradicating bacteria in a biofilm, optionally wherein the bacteria are present in a biofilm and are killed, reduced, and/or eradicated, and preferably the biofilm is not dispersed. In some embodiments, the bacteria may be present on an inanimate surface, including but not necessarily limited to a medical device, including but not necessarily limited to implantable or implanted medical devices.

The disclosed compounds, compositions, and methods may be utilized for killing, reducing, and/or eradicating bacteria in aggregates, optionally wherein the bacteria are present in aggregates and are killed, reduced, and/or eradicated, and preferably the aggregates are not dispersed.

DETAILED DESCRIPTION

Figure 1:
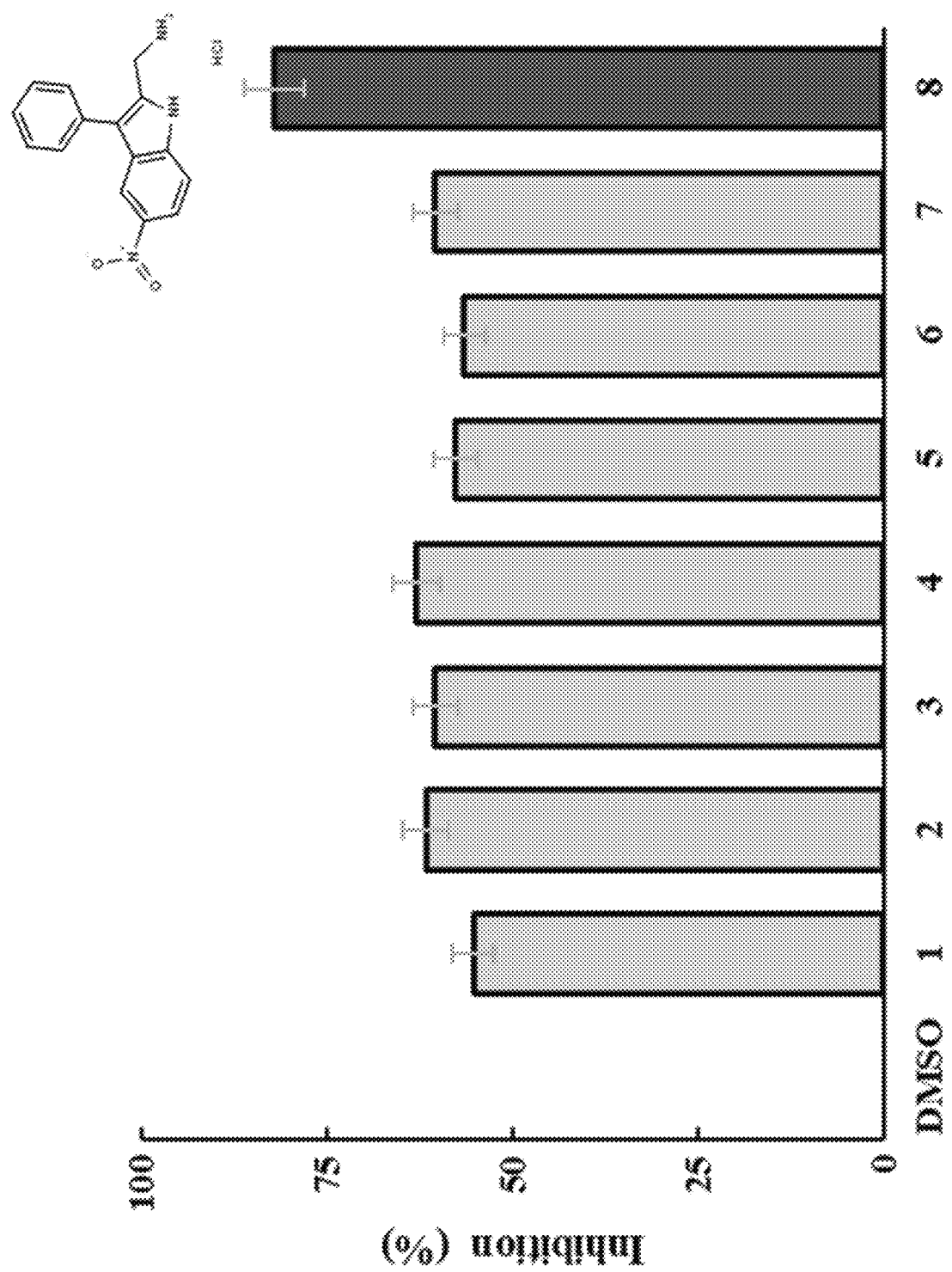
FIG. 1. Most effective persister killing compounds identified from screening persister cells. *Escherichia coli* persister cells were treated for 24 hr at 100 µM with:
1: N-(3,4-dichlorophenyl)-N'-(3-fluorophenyl) thiourea;
2: 2-({2-[(4-bromophenyl)amino]-4-quinazolinyl}amino) ethanol hydrochloride;
3: 2-[(6-phenyl-2,3,4,9-tetrahydro-1H-carbazol-1-yl)amino] ethanol;
4: 1-(3,6-dichloro-9H-carbazol-9-yl)-3-(2-methyl-1H-imidazol-1-yl)-2-propanol;
5: N-[2-(4-fluorophenyl)ethyl]-N'-(4-nitrophenyl) thiourea;
6: N-(4-chlorobenzyl)-N'-4-pyridinylthiourea;
7: N'-(3,5-dichloro-2-hydroxybenzylidene)-2-oxo-4-phenyl-3-pyrrolidinecarbohydrazide; and
8: [(5-nitro-3-phenyl-1H-indol-2-yl)methyl]amine hydrochloride (NPIMA, structure shown in inset).

The present invention is described herein using several definitions, as set forth below and throughout the application.

Definitions

Unless otherwise specified or indicated by context, the terms "a", "an", and "the" mean "one or more." For example, "a compound" or "an antibiotic" should be interpreted to mean "one or more compounds" and "one or more antibiotics," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment, for example, treatment by include administering a therapeutic amount of one or more compounds for killing, reducing, and/or eradicating bacteria from a bacterial population. A "subject in need of treatment" may include a subject having an infection characterized by the presence of bacterial persister cells and/or dormant viable but non-culturable (VBNC) cells.

The present disclosure provides methods for killing, reducing, and/or eradicating bacterial persister cells and/or dormant viable but non-culturable (VBNC) cells in a bacterial population. The persister and/or VBNC cells may be present in population that comprises, consists essentially of, or consists of such cells. The disclosed methods typically comprise administering an effective amount of a compound of Table 1 or Table 4 (or a non-salt or salt form thereof), wherein the bacterial persister cells and/or the VBNC cells in the bacterial population are killed, reduced, and/or or eradicated. Suitable compounds include, but are not limited to [(5-nitro-3-phenyl-1H-indol-2-yl)methyl]amine and salts thereof such as [(5-nitro-3-phenyl-1H-indol-2-yl)methyl]amine hydrochloride (NPIMA), and 2-{[2-(4-bromophenyl)-2-oxoethyl]}-3-ethyl-5,6,7,8-tetrahydro[1]benzothieno[2,3-d]pyrimidin-4(3H)-one (BPOET) or salts thereof.

As used herein, the term "compound" includes any compound listed in Table 1 or Table 4, or salt forms or non-salt forms thereof. In addition, where the compound listed in Table 1 or Table 4 is a salt form, such as NPIMA which is a hydrochloride salt of [(5-nitro-3-phenyl-1H-indol-2-yl)methyl]amine, the term "compound" includes alternative salt forms of the compound listed in Table 1 or Table 4. An alternative salt form of NPIMA may include a salt form that is not a hydrochloride salt form.

"Persister cells" as used herein means bacteria, including pathogenic bacteria, that neither grow nor die in the presence of microbicidal antibiotics with the exception of the compounds disclosed herein. "Persister cells" as used herein also include antibiotic tolerant cells. The disclosed compounds, compositions, and methods may be utilized for killing persister cells and/or reducing or eradicating the number of persister cells in a bacterial population. The population of persister cells can be present in an infection (e.g., in a subject), in a biological sample, or on an inanimate surface. In non-limiting examples, surfaces may include non-porous surfaces, such as surfaces in a hospital, surfaces on a medical device, and/or a surfaces that are used for food processing or preparation.

Persister cells and/or VBNC cells that are killed, reduced, and/or eradicated may be responsible for and/or positively correlated with the presence of recalcitrant infections, such as chronic recalcitrant infections. Chronic recalcitrant infections are known to occur when the functioning of an individual's immune system is less than optimal. Known examples of chronic infection occur in a variety of individuals, such as those who are immunocompromised because of immunosuppressive drug courses, co-infection with viruses, or individuals who have an infection that forms a biofilm or aggregates. "Biofilm" as used herein is an assemblage of surface-associated microbial cells that is enclosed in an extracellular polymeric substance matrix. "Biofilm" as used herein also is an aggregate of free-floating cells. As is also well known in the art, biofilms and aggregates impede access of immune cells and immunological signaling molecules to bacteria, and thus limit the effectiveness of even normally functioning immune systems. Further, biofilms are known to form in a variety of wounds inside the body, as well as on surfaces of indwelling medical devices. In certain instances, such infections and biofilms can be populated by drug-resistant bacteria present on the devices, and in the tissue that comes into contact with them. However, in many instances chronic and recalcitrant infections arise because comparatively slow-growing bacteria develop into drug-tolerant persister cells that are difficult to eradicate with currently used antibiotics, and this can occur with or without the presence of an implanted device. Thus, upon cessation of a course of antibiotics and the subsequent decrease in its concentration, persister cells can exploit an opportunity to grow and repopulate the infection and/or biofilm. The approaches of the present disclosure are particularly suited for reducing the number of and/or eradicating such cells.

In some embodiments, the methods disclosed herein may be utilized to reduce persister cells and/or VBNC cells present in a bacterial population, wherein the reduction is greater than a reference. The reference may comprise any suitable control, value or measurement of the reduction of persister cells, such as a standardized curve, a titration, the area under a curve, or a comparison to the capability of another antimicrobial compound to kill the persister cells and/or the VBNC cells. In some embodiments, the reference comprises a value obtained from measuring the amount of persister cells and/or VBNC cells of the same bacterial species that are killed using an antibiotic that is not a compound of Table 1 or Table 4 (or a salt or non-salt thereof). In some embodiments, the amount of the reference antibiotic used to compare to compound of Table 1 or Table 4, or a salt or non-salt thereof, i.e., an amount of the reference antibiotic that kills non-persistent cells at the same minimum inhibitory concentration (MIC) of compound of Table 1 or Table 4 (or a salt or non-salt thereof), respectively.

The disclosed compositions for killing, reducing, and/or eradicating persister cells may comprise, consist essentially of, or consist of a compound of Table 1 or Table 4 (or a salt or non-salt thereof) such as NPIMA and BPOET, preferably for use as an antibiotic. In some embodiments, the disclosed compositions comprise, consist essentially of, or consist of Table 1 or Table 4 (or a salt or non-salt thereof), as the only antibiotic agent in the composition. In other embodiments, the disclosed composition comprise, consist essentially of, or consist of two or more antibiotic agents including at least a compound of Table 1 or Table 4 (or a salt or non-salt thereof) and further including an antibiotic that that is a member of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, and the like.

In the disclosed methods, a bacterial population may be administered a compound of Table 1 or Table 4 (or a salt or non-salt thereof) as an antibiotic and the bacterial population further may be administered one or more different antibiotics which may be a compound of Table 1 or Table 4 (or a salt or non-salt thereof) or an antibiotic that that is a member of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, and the like. As such, the bacterial population may be administered two or more antibiotics, which may be administered concurrently or sequentially, where one antibiotic is administered to the bacterial population and another antibiotic is subsequently administered to the bacterial population.

In some embodiments of the disclosed methods, a first antibiotic is administered to a bacterial population, which first antibiotic is a member of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, and the like, and subsequently a second antibiotic is administered to the bacterial population, which second antibiotic is a compound of Table 1 or Table 4 (or a salt or non-salt thereof) is administered. In other embodiments, a first antibiotic is administered to a bacterial population, which first antibiotic is a compound of Table 1 or Table 4 (or a salt or non-salt thereof) is administered, and subsequently a second antibiotic is administered to the bacterial population, which second antibiotic is a member of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, and the like.

In some embodiments of the disclosed methods, the persister cells and/or VBNC cells may be resistant to one or more antibiotics. For example, in some embodiments of the disclosed methods, the persister cells and/or VBNC cells may be resistant to an antibiotic which is a member of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, and the like.

Various methods known to those skilled in the art may be used to administer the disclosed compounds and compositions comprising the disclosed compounds for the purpose of reducing or eradicating populations of persister cells and/or VBNC cells, including such populations when they are present in an infection in an individual. These methods include but are not necessarily limited to intradermal, transdermal, intravenous, topical, intramuscular, intraperitoneal, intravenous, subcutaneous, oral, and intranasal routes. In certain aspects the disclosure includes providing the compounds in the form of creams, aqueous solutions, suspensions or dispersions, oils, balms, foams, lotions, gels, cream gels, hydrogels, liniments, serums, films, ointments, sprays or aerosols, other forms of coating, or any multiple emulsions, slurries or tinctures. The compositions may be embedded in materials, such as a medical device or other implement used in treating or manipulating a body, organ, tissue or biological fluid. The compositions can also include liposomes, microsomes, nanoparticles, and any other suitable vehicle for delivering the compounds such that they reduce or eradicate persister cells where present. Further, it will be recognized by those of skill in the art that the form and character of the particular dosing regimen employed in the method of this disclosure will be dictated by the route of administration and other well-known variables, such as the age, sex, health and size of the individual, the type and severity of bacterial infection, or risk of bacterial infection, and other factors that will be apparent to the skilled artisan given the benefit of the present disclosure, improve the time in blood circulation, the disclosed compounds and compositions comprising the disclosed compounds may be combined with nano-formulations comprised of microemulsions, carbon nanoparticles, true nano-spheres, or polyanionic PEG-polyglutamate co-polymers.

In certain embodiments, the method of the disclosure results in eradication of a bacterial population comprising the bacterial persister cells and/or VBNC cells from an infection, such as from an infection of an organ, tissue, skin, or biological fluid from an individual, or from the surface of an inanimate object, including but not necessarily limited to medical devices, such as implantable or implanted medical devices, and/or any medical device that may stay in contact with the skin or be fully or partially present within the body of an individual for a period of time during which the surface of the device may be susceptible to biofilm formation.

The disclosed compounds, compositions, and methods may be utilized for killing, reducing, and/or eradicating bacteria that are present in anaerobic conditions. The disclosed compounds, compositions, and methods may be utilized for killing, reducing, and/or eradicating bacteria of a variety of types, include Gram-negative and Gram-positive pathogenic bacteria. In certain approaches, the bacteria are pathogenic and/or are selected from *Escherichia* spp. such as *E. coli*, *Staphylococcus* spp. such as *S. aureus*, and *Pseudomonas* spp. such as *Pseudomonas aeruginosa*. In other embodiments, disclosed compounds, compositions, and methods may be utilized for killing, reducing, and/or eradicating bacteria that are selected from *V. cholerae*. *B. burgdorferi*, *Streptococcus* spp., *S. typhimurium*, *E. faecalis*, *A. baumannii*, *A. iwoffli*, *S. marcescens*, *P. mirabilis*, *K. pneumoniae*, *A. calcoaceticus*, *S. mutans*, *P. gingivalis*, *H. influenza*, *H. pylori*, *N. meningitides*, *N. gonorrhea*, *M. kansasii*, *B. anthracis*, *P. acnes*, *C. tetani*, *C. trachomatis*, *L. pneumophila*, *Y. pestis*, *B. abortus*, *F. tularensis*, *V. harveyi*, and combinations thereof.

In some embodiments, the disclosed compounds, compositions, and methods may be utilized for killing, reducing, and/or eradicating bacteria that are present in a wound of an individual. In some embodiments, the disclosed methods comprise administering to a subject in need thereof a composition comprising an effective amount of a compound of Table 1 or Table 4 (or a salt or non-salt form thereof). A subject in need thereof includes a subject known to be in need of reducing or eradicating an infection, including an infection comprising persister cells and/or VBNC cells.

In some embodiments, the disclosed compounds, compositions, and methods may be utilized for killing, reducing, and/or eradicating bacteria that are present in a liquid biological sample or liquid environment. For example, the disclosed compounds, compositions, and methods may be utilized for killing, reducing, and/or eradicating bacteria that are present in suspension.

In some embodiments, the disclosed compounds, compositions, and methods may be utilized to kill, reduce, and/or eradicate persister cells and/or VBNC cells in an infection in a subject who has been diagnosed with a bacterial infection and has been treated with at least one antibiotic other than the compounds disclosed in Table 1 and Table 4 (or salt or non-salt forms thereof), optionally where the diagnosed bacterial infection was not cleared by the previous treatment. In some embodiments, the subject has been treated with an antibiotic that is a member of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, and the like.

In some embodiments, the disclosed compounds, compositions, and methods may be utilized to kill, reduce, and/or eradicate persister cells and/or VBNC cells that are present in a biofilm. In some embodiments, the bacterial persister cells and/or VBNC cells are reduced or eradicated from a biofilm, but the biofilm is not dispersed.

In some embodiments, the disclosed compounds, compositions, and methods may be utilized to kill, reduce, and/or eradicate persister cells and/or VBNC cells that may be present on an inanimate surface. Inanimate surfaces may include, but are not limited to surfaces present on an implanted medical device or surfaces outside a body.

The compounds disclosed herein may be administered as pharmaceutical compositions and, therefore, pharmaceutical compositions incorporating the compounds are considered to be embodiments of the subject matter disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-. 1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds disclosed herein or salts, esters, and/or amides, thereof. Solvate forms may include ethanol solvates, hydrates, and the like.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered: the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Illustrative Embodiments

Embodiment 1. A method for killing bacterial persister cells and/or dormant "viable but non-culturable" (VBNC) cells in a bacterial population, the method comprising administering to the bacterial population an effective amount of a compound of Table 1 or Table 4 or a salt or non-salt form thereof.

Embodiment 2. The method of claim 1, wherein the compound is [(5-nitro-3-phenyl-1H-indol-2-yl)methyl]amine having the formula:

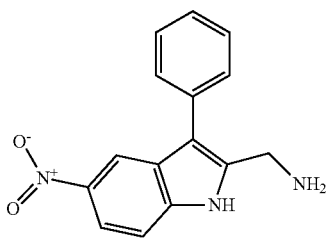 [SMILES: NCc1[nH]c2ccc([N+](=O)[O-])cc2c1-c1ccccc1]

or a salt thereof such as [(5-nitro-3-phenyl-1H-indol-2-yl)methyl]amine hydrochloride (NPIMA), having the formula:

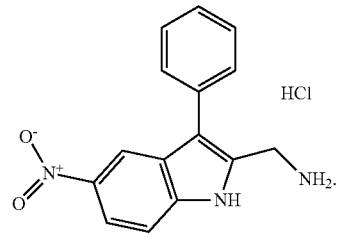 [SMILES: NCc1[nH]c2ccc([N+](=O)[O-])cc2c1-c1ccccc1 ; Cl]

Embodiment 3. The method of claim 1, wherein the compound is 2-{[2-(4-bromophenyl)-2-oxoethyl]thio}-3-ethyl-5,6,7,8-tetrahydro[1]benzothieno[2,3-d]pyrimin-4(3H)-one (BPOET) having the formula:

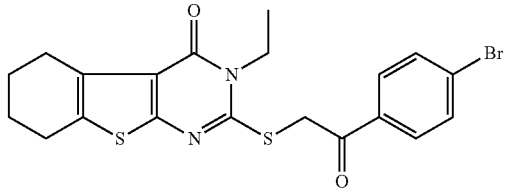 [SMILES: CCn1c(SCC(=O)c2ccc(Br)cc2)nc2sc3c(c2c1=O)CCCC3]

or a salt thereof.

Embodiment 4. The method of claim 1, wherein the bacterial persister cells and/or VBNC cells are resistant to one or more antibiotics which do not comprise any compound of Table 1 or Table 4 or a salt or non-salt form thereof.

Embodiment 5. The method of claim 1, wherein the bacterial persister cells and/or VBNC cells comprise pathogenic Gram-negative bacteria.

Embodiment 6. The method of claim 1, wherein the bacterial persister cells and/or VBNC cells comprise pathogenic Gram-positive bacteria.

Embodiment 7. The method of claim 1, wherein the bacterial persister cells and/or VBNC comprise bacteria selected from *Escherichia* spp., *Staphylococcus* spp., and *Pseudomonas* spp.

Embodiment 8. The method of claim 1, wherein the bacterial persister cells and/or VBNC comprise *E. coli*.

Embodiment 9. The method of claim 1, wherein the bacterial persister cells and/or VBNC comprise *S. aureus*.

Embodiment 10. The method of claim 1, wherein the bacterial persister cells and/or VBNC comprise *P. aeruginosa*.

Embodiment 11. The method of claim 1, wherein the bacterial persister cells and/or VBNC cells are present in anaerobic conditions.

Embodiment 12. The method of claim 1, wherein the bacterial population is present in a biofilm.

Embodiment 13. The method of claim 1, wherein the bacterial population is present in a biofilm and the bacterial persister cells and/or VBNC cells are reduced or eradicated, but the biofilm is not dispersed.

Embodiment 14. The method of claim 1, wherein the bacterial population is present in an infection in a wound of an individual, and/or wherein the bacterial population is present in a liquid biological sample or liquid environment (e.g., wherein the bacterial population is present in suspension).

Embodiment 15. The method of claim 1, wherein the population comprises an infection in an individual, wherein the individual has been previously diagnosed with a bacterial infection and has been treated with at least one antibiotic which does not comprise any compound of Table 1 or Table 4 or a salt or non-salt form thereof.

Embodiment 16. The method of claim 1, further comprising administering to the bacterial population an antibiotic which does not comprise any compound of Table 1 or Table 4 or a salt or non-salt form thereof.

Embodiment 17. The method of claim 1, wherein the bacterial persister cells and/or VBNC cells are reduced in the bacterial population.

Embodiment 18. The method of claim 1, wherein the bacterial persister cells and/or VBNC cells are eradicated from the bacterial population.

Embodiment 19. The method of claim 1, wherein a reduction in the bacterial persister cells and/or the VBNC cells in the population occurs after the compound is administered to the population.

Embodiment 20. The method of claim 19, wherein the reduction of the persister cells and/or the VBNC cells is greater than a reference, wherein the reference comprises a value obtained from reducing persister cells and/or or reducing VBNC cells of the same bacterial species using a corresponding amount of an antibiotic which does not comprise any compound of Table 1 or Table 4, such as ciprofloxacin, ampicillin, or gentamicin.

Examples

The following Examples are illustrative and should not be interpreted to limit the scope of the claimed subject matter.

Example 1—Identification of a Potent Indigoid Persister Antimicrobial by Screening Dormant Cells Reference is made to Song S., et al., "Identification of a Potent Indigoid Persister Antimicrobial by Screening Dormant Cells," Biotechnology and Bioengineering, Volume 116, Issue 9, pages 2263-2274, 4 Jun. 2019, the content of which is incorporated herein by reference in its entirety.

Abstract

The subpopulation of bacterial cells that survive myriad stress conditions (e.g., nutrient deprivation and antimicrobials) by ceasing metabolism, revive by activating ribosomes. These resuscitated cells can reconstitute infections; hence, it is imperative to discover compounds which eradicate persister cells. By screening 10,000 compounds directly for persister cell killing, we identified 5-nitro-3-phenyl-1Hindol-2-yl-methylamine hydrochloride (NPIMA) as a compound that kills *Escherichia coli* persister cells more effectively than the best indigoid found to date, 5-iodoindole, and better than the DNA-crosslinker cisplatin. In addition, NPIMA eradicated *Pseudomonas aeruginosa* persister cells in a manner comparable to cisplatin. NPIMA also eradicated *Staphylococcus aureus* persister cells but was less effective than cisplatin. Critically, NPIMA kills Gram-positive and Gram-negative bacteria by damaging membranes and causing lysis as demonstrated by microscopy and release of extracellular DNA and protein. Furthermore, NPIMA was effective in reducing *P. aeruginosa* and *S. aureus* cell numbers in a wound model, and no resistance was found after 1 week. Hence, we identified a potent indigoid that kills persister cells by damaging their membranes.

1|Introduction

Nearly all bacterial cells are stressed (e.g., lack of nutrients and antimicrobials: Kim, Chowdhury, Yamasaki, & Wood, 2018; Song & Wood, 2018), so they reduce their metabolism and a subpopulation becomes dormant (Bigger, 1944; Hobby, Meyer, & Chaffee, 1942); this dormant state is known as persistence. Beyond being prevalent in the environment, persistence is relevant in medicine since these cells likely reconstitute recurring infections (Van den Bergh, Fauvart, & Michiels, 2017). Because traditional antibiotics target growing cells and are largely ineffective against persister cells that lack the metabolic activity (Defrain, Fauvart, & Michiels, 2018), it is critical to identify new compounds for killing persister cells to control infections.

To target effectively persister cells with new compounds, it is germane to understand how they form and how they resuscitate. Cells have myriad ways to combat stress: for example, they utilize sigma factors like RpoS in *Escherichia coli* that redirect gene expression upon nutrient depletion (Wang, Kim, et al., 2011), and most cells in a population employ such an active response. However, a subpopulation of cells, as a result of noisy gene expression or through elegant regulation, becomes dormant (Wood, Song, & Yamasaki, 2019). To reduce metabolism and become persistent, cells utilize toxin/antitoxin (TA) systems (Wang & Wood, 2011); direct evidence of the importance of specific TA systems in persistence is that deletion of toxins MqsR (Kim & Wood, 2010; Luidalepp, Jõers, Kaldalu, & Tenson, 2011), TisB (Dörr, Vulić, & Lewis, 2010), and YafQ (Harrison et al., 2009) reduces persistence, and production of toxins generally increases persistence (Chowdhury, Kwan, & Wood, 2016).

After surviving stress through dormancy, single-cell experiments demonstrate *E. coli* persister cells resuscitate by activating ribosomes (Kim, Yamasaki, Song, Zhang, & Wood, 2018). Resuscitation is heterogeneous as some cells wake immediately and others do not divide or elongate until their ribosome levels are increased (Kim, Yamasaki, et al., 2018). In contrast to ineffective traditional antibiotics, some compounds have been identified that kill persister cells. For example, two compounds approved by the U.S. Food and Drug Administration for anticancer treatments, mitomycin C and cisplatin, kill *Escherichia coli*, *Staphylococcus aureus*, *Pseudomonas aeruginosa*, *Acinetobacter baumannii*, and EHEC persister cells by cross-linking their DNA while they are dormant (Chowdhury, Wood, Martinez-Vázquez, Garcia-Contreras, & Wood, 2016; Cruz-Muñiz et al., 2016; Kwan, Chowdhury, & Wood, 2015). As originally suggested due to its toxicity (Chowdhury, Wood, et al., 2016), cisplatin has been shown to be effective when applied topically for treating *P. aeruginosa* infections in a murine keratitis model (Yuan et al., 2018). In addition, Trp/Arg containing antimicrobial peptides kill persister cells by disrupting the cell structure of the dormant cells (Kwan, Chowdhury, et al., 2015), and ADEP4, an acyldepsipeptide antibiotic, combined with rifampicin, can eradicate *S. aureus* persisters by causing ClpP protease to degrade proteins nonspecifically (Conlon et al., 2013). By conjugating the traditional antibiotic vancomycin to the cell-penetrating transporter D-octaarginine, *S. aureus* persisters and biofilm cells were killed (Antonoplis et al., 2018). In addition, the vitamin A derivatives, retionoids CD437 and CD1530, have been identified that kill *S. aureus* persisters by disrupting lipid bilayers after screening 82,000 small molecules (Kim, Zhu, et al., 2018). Since indole reduces persistence (flu, Kwan, Osbourne, Benedik, & Wood, 2015; Kwan, Osbourne, Hu, Benedik, & Wood, 2015), indole derivatives, such as 5-iodoindole and 4-fluoroindole, have been tested and found to kill *E. coli*, *S. aureus*, and EHEC persister cells (Lee, Kim, Gwon, Wood, & Lee, 2016), but they are not effective against *P. aeruginosa*.

In the present study, by screening 10,000 compounds, we identified that 5-nitro-3-phenyl-1H-indol-2-yl methylamine hydrochloride (NPIMA) kills *E. coli* persister cells. In addition, we found the mechanism of killing is via cell lysis. Furthermore, we found that NPIMA is more effective than 5-iodoindole with the opportunistic pathogen *P. aeruginosa* and that NPIMA eradicates the persister cells of both *P. aeruginosa* and *S. aureus*.

2|Materials and Methods 2.1|Bacteria and Growth Conditions

The bacteria used in this study are *E. coli* K-12 BW25113 (Baba et al., 2006), *S. aureus* ATCC29213, and *P. aeruginosa* PA14 (Liberati et al., 2006). Lysogeny broth (LB; Bertani, 1951) was used at 37° C. for culturing the bacteria. 2-(Aminomethyl)-indole was obtained from Sigma-Aldrich (catalog number 563838), and 2-methyl-5-nitro-3-phenyl-1H-indole was obtained from ChemBridge (San Diego, Calif.).

2.2|Persister Cells

*E. coli* persister cells were prepared following our previous method (Kim, Yamasaki, et al., 2018; Kwan, Valenta, Benedik, & Wood, 2013). Exponentially-growing cells (turbidity of 0.8 at 600 nm) were treated with rifampicin (100 µg/ml for 30 min) to stop transcription, washed, and any remaining nonpersister cells were lysed by ampicillin in LB (100 µg/ml for 3 hr). Cells were harvested by centrifugation (17,000 g for 1 min) and washed with 1×phosphate-buffered saline buffer (PBS, 8 g NaCl, 0.2 g KCl, 1.15 g $Na_2HPO_4$, and 0.2 g $KH_2PO_4$ per 1,000 ml) twice to remove all possible carbon sources, then resuspended with 1×PBS. Natural *E. coli* persister cells were generated by treating stationary-phase cells (turbidity of 6 at 600 nm) with ampicillin (100 µg/ml) for 3 hr. *P. aeruginosa* PA14 persister cells were prepared by incubating to the stationary phase, diluting sixfold, and treating with carbonyl cyanide m-chlorophenylhydrazone (CCCP, 50 mg/ml stock solution in dimethyl sulfoxide [DMSO]) to stop adenosine triphosphate (ATP) production (200 µg/ml for 3 hr), washed twice with 0.85% NaCl (5,000 g for 10 min), and any nonpersister cells were killed by ciprofloxacin (5 µg/ml) in LB for 3 hr. Following the antibiotic treatment, bacteria were washed twice with 0.85% NaCl (5,000 g for 10 min).

2.3|ChemBridge Screen

To identify compounds that kill *E. coli* persister cells, 10,000 compounds of the DIVERset Library from ChemBridge (San Diego, Calif.) were tested by adding 4 µl of each (in DMSO, final concentration 100 µM) to 186 µl of LB in 96-well plates along with 10 µl of persister cells; the persister cells were added after the ChemBridge chemical since LB wakes persister cells (Kim, Yamasaki, et al., 2018). For the negative control, pure DMSO (final concentration 2 vol %) was used. The degree of inhibition was determined by the change in turbidity at 600 nm after 24 hr. The best 26 compounds were re-tested with the same conditions.

2.4|Minimum Inhibitory Concentration (MIC)

To determine the MICs of NPIMA and 5-iodoindole for *E. coli* K-12, *S. aureus*, and *P. aeruginosa* PA14, cells were inoculated into LB at varying concentrations and grown for 24 hr. The MIC was determined as the lowest concentration that prevented an increase in growth as evidenced by a lack of change of turbidity.

2.5|Live/Dead Assay

Cell viability after treating with NPIMA was determined using the using the LIVE/DEAD BacLight Bacterial Viability Kit (catalog number, L7012; Molecular Probes, Inc., Eugene, Oreg.). The fluorescence signal was analyzed via a Zeiss Axioscope.A1 using excitation at 485 nm and emission at 530 nm for green fluorescence and using excitation at 485 nm and emission at 630 nm for red fluorescence.

2.6|In Vitro Wound Model

Overnight cultures of *S. aureus* and *P. aeruginosa* PA14 were diluted in wound-like media (45% Bolton broth, 50% bovine plasma, and 5% laked horse blood; Sun, Dowd, Smith, Rhoads, & Wolcott, 2008) to a turbidity of 0.5 at 600 nm in 1 ml. Each culture (1%) was used to inoculate fresh 5 ml of wound-like media. The combined culture (200 µl/well) was placed into 96-well plates and incubated at 37° C. with shaking for 24 hr. The non-gel liquid was removed, then the gel was washed once with PBS. NPIMA (0.1 and 0.5 mM) and DMSO were then added (200 µl/well) to the plates, which were incubated for another 6 hr with shaking. By triturating, the gel with cells was removed and added to 0.8 ml of PBS, and the cell viability was measured by spreading 100 µl of diluted culture on LB plates.

2.7|Transmission Electron Microscopy (TEM)

For transmission electron microscopy (TEM), *E. coli* BW25113 was grown to a turbidity of 0.8 at OD600, contacted with NPIMA at 100 µM for 0.75 hr in PBS, centrifuged at 8000 g, and resuspended in PBS. The samples were fixed with buffer (2.5% glutaraldehyde in 0.1M cacodylate buffer, pH 7.4) and negative stained with 2% uranyl acetate in the dark for 1 hr, then dehydrated. The sectioned specimens were stained again with uranyl acetate and lead citrate after dehydration and resin embedded. TEM images were obtained using a JEOL JEM 1200 EXII instrument.

2.8|Lysis Assays

Exponentially-growing *E. coli* BW25113 cells (turbidity 0.8 at 600 nm) were washed twice with 0.85% NaCl, resuspended in 1 ml of 1×PBS, and NPIMA (100 µM) was added for 1 hr for *E. coli* and *P. aeruginosa* and 6 hr for *S. aureus* with shaking at 250 rpm (0.1% DMSO was used as the negative control). Cell supernatants were collected after centrifuging at 6,500 g (4° C. for 15 min), and total protein was measured by the Bicinchoninic Acid (BCA) protein assay Kit (Prod #23227; Pierce). DNA in the supernatant (199 l) was detected by adding 1 µl of Picogreen (P7589; Invitrogen) and incubating for 5 mm at room temperature in the dark room. The fluorescence signal was read by a Tecan microplate reader (Infinite M200PRO) with 480 nm excitation and 520 nm emission by utilizing a calibration curved made with plasmid pEX18Ap at 0, 0.004, 0.008, 0.016, 0.063, 0.125, 0.25, and 0.5 ng/µl.

2.9|Viability and Cytotoxicity Assays

For bacterial viability, cells were washed twice with 0.85% NaCl, resuspended in 1×PBS, and cell counts were determined via the drop assay (Donegan, Matyac, Seidler, & Porteous, 1991). For human cell viability, pre-cultured human cancer HT-29 cells were dispensed in 98 µl in 96-well plates with approximately 5,000 cells/well. NPIMA was added (2 µl) to produce concentrations of 5, 10, 100, and 200 µM. For controls, Triton X-100 (positive control) and DMSO (negative solvent control), were used, and the medium was used for background. Plates were incubated in a humidified incubator (37° C., 5% $CO_2$) for 24 hr. Cell viability was determined via a cell counting kit (CCK-8 Kit, ab228554: Abcam), and cytotoxicity was determined via the lactate dehydrogenase (LDH) assay (LDH Assay Kit, MK401; Takara).

3|Results 3.1|NPIMA Kills *E. coli* Persister Cells

To identify compounds capable of killing *E. coli* persister cells, we created a population that consists solely of persister cells and has their population increased by 105-fold by pretreating exponentially-growing cells with rifampicin (100 μg/ml) for 30 min to stop transcription followed by ampicillin treatment (100 μg/ml) for 3 hr to kill any non-persister cells (Kwan et al., 2013). This method for generating persister cells has been evaluated eight ways (Kim, Yamasaki, et al., 2018) and used by us to determine that persister cells wake via ribosome resuscitation (Kim, Yamasaki, et al., 2018) and to show that the cells capable of resuscitation in a viable but not culturable population are equivalent to persister cells (Kim, Chowdhury, et al., 2018). In addition, this method has been adopted by at least six independent groups (Cui et al., 2018; Grassi et al., 2017; Narayanaswamy et al., 2018; Pu et al., 2019; Sulaiman, Hao. & Lam, 2018; Tkhilaishvili, Lombardi, Klatt, Trampuz, & Di Luca, 2018).

To screen directly for killing persister cells, a high-throughput approach using 96-well microtiter plates was devised that consisted of (a) washing persister cells formed from exponentially-growing cells using rifampicin pretreatment followed by ampicillin treatment, (b) adding 10 μl of the persister cells to 190 μl of LB containing one each of the 10,000 compounds of the DiverSet library dissolved in dimethyl sulfoxide (100 μM final concentration), and (c) monitoring for growth via change in turbidity for 24 hr. With this approach, we allowed for up to a 140-fold change in turbidity (0.005 could be increased to 0.69).

Table 1 shows the 25 persister cell inhibitors and their structures that were identified in the initial screen. Of these 25 persister inhibitors, a second screen was performed under the same conditions as the original screen; 8 of these 25 compounds were selected as the most potent (FIG. 1) with NPIMA substantially more effective than the other compounds. Critically, NPIMA was the only compound which reduced the turbidity during the first and second screen, suggesting NPIMA lyses persister cells. Hence, we focused on this compound.

TABLE 1

Persister cell inhibitors and their structures that were identified in the initial screen

| Name | Structure |
| --- | --- |
| [(5-nitro-3-phenyl-1H-indol-2-yl)methyl]amine hydrochloride (NPIMA) | 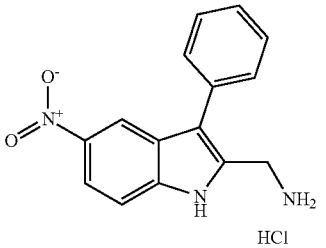 [SMILES: NCc1[nH]c2ccc([N+](=O)[O-])cc2c1-c1ccccc1 ; Cl] |
| 2-({2-[(4-chlorophenyl)amino]-4-quinazolinyl}amino)ethanol hydrochloride | 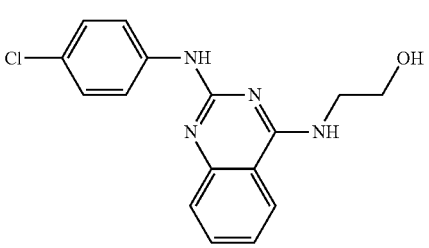 |
| 1-[2-(4-chlorophenoxy)-2-methylpropanoyl]-4-methylpiperazine | 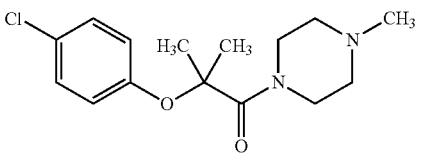 [SMILES: CN1CCN(C(=O)C(C)(C)Oc2ccc(Cl)cc2)CC1] |

TABLE 1-continued

Persister cell inhibitors and their structures that were identified in the initial screen

| Name | Structure |
|---|---|
| N-benzyl-N-{[3-(4-methoxyphenyl)-1-phenyl-1H-pyrazol-4-yl]methyl}acetamide | 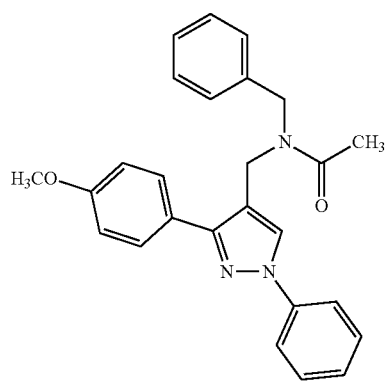 [SMILES: COc1ccc(-c2nn(-c3ccccc3)cc2CN(Cc2ccccc2)C(C)=O)cc1] |
| N-(3,4-dichlorophenyl)-N'-(3-fluorophenyl)thiourea | 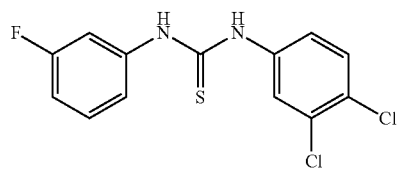 [SMILES: Fc1cccc(NC(=S)Nc2ccc(Cl)c(Cl)c2)c1] |
| 2-({2-[(4-bromophenyl)amino]-4-quinazolinyl}amino)ethanol hydrochloride | 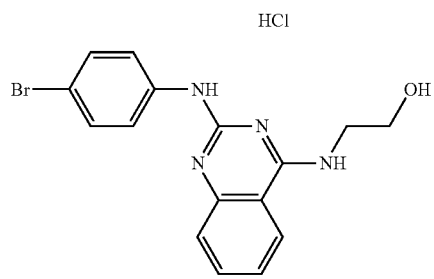 [SMILES: Cl ; OCCNc1nc(Nc2ccc(Br)cc2)nc2ccccc12] |
| N-2-(4-ethoxyphenyl)-2,4-quinazolinediamine hydrochloride | 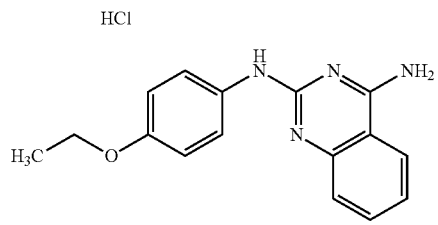 [SMILES: Cl ; CCOc1ccc(Nc2nc(N)c3ccccc3n2)cc1] |
| 4-{[(5-nitro-2-thienyl)methylene]amino}benzamide | 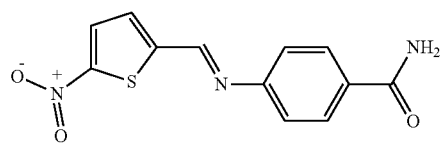 |
| 2-[(6-phenyl-2,3,4,9-tetrahydro-1H-carbazol-1-yl)amino]ethanol | 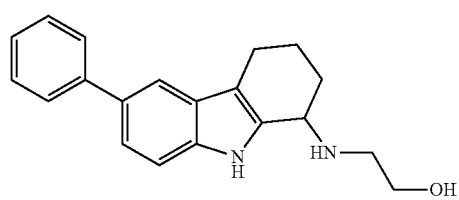 [SMILES: OCCNC1CCCc2c1[nH]c1ccc(-c3ccccc3)cc21] |

TABLE 1-continued

Persister cell inhibitors and their structures that were identified in the initial screen

| Name | Structure |
|---|---|
| 2-bromo-4-chlorophenyl phenylcarbamate | 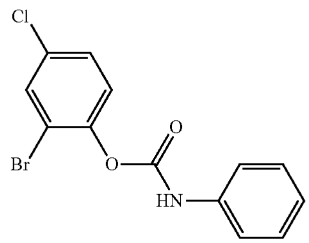 [SMILES: O=C(Nc1ccccc1)Oc1ccc(Cl)cc1Br] |
| 1-(3,6-dichloro-9H-carbazol-9-yl)-3-(2-methyl-1H-imidazol-1-yl)-2-propanol | 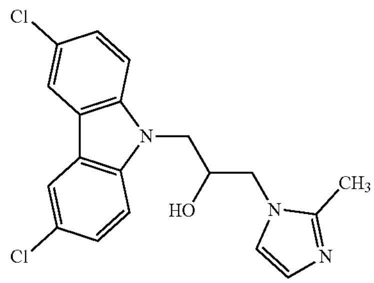 [SMILES: Cc1nccn1CC(O)Cn1c2ccc(Cl)cc2c2cc(Cl)ccc21] |
| N-(3-chloro-4-fluorophenyl)-N'-[2-(difluoromethoxy)phenyl]thiourea | 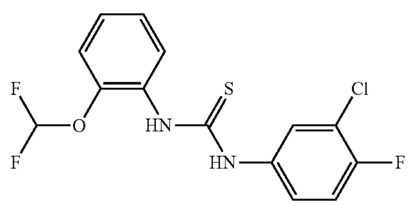 [SMILES: Fc1ccc(NC(=S)Nc2ccccc2OC(F)F)cc1Cl] |
| 2-(butyryloxy)-1H-benzo[de]isoquinoline-1,3(2H)-dione | 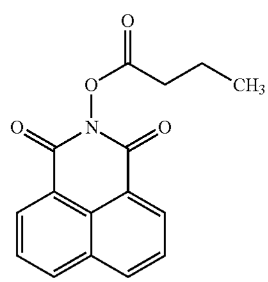 [SMILES: CCCC(=O)ON1C(=O)c2cccc3cccc(c23)C1=O] |
| N-phenyl-N'-[(1-phenylcyclopentyl)methyl]thiourea | 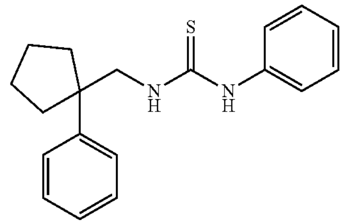 [SMILES: S=C(NCC1(c2ccccc2)CCCC1)Nc1ccccc1] |
| N-[2-(4-fluorophenyl)ethyl]-N'-(4-nitrophenyl)thiourea | 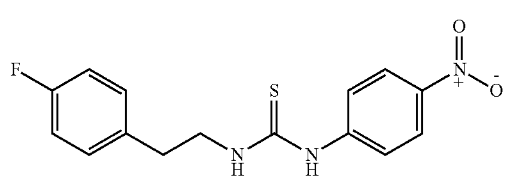 |

TABLE 1-continued

Persister cell inhibitors and their structures that were identified in the initial screen

| Name | Structure |
| --- | --- |
| 2,4-dichloro-5-(5-nitro-2-furyl)benzoic acid | 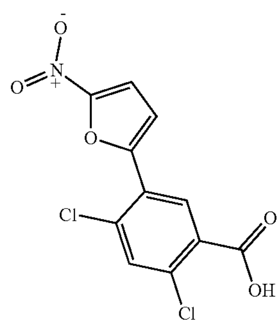 |
| N-(3-chlorophenyl)-N'-[3-(trifluoromethyl)phenyl]thiourea | 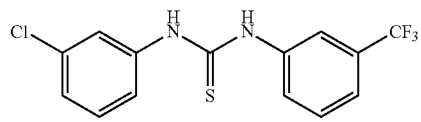 [SMILES: FC(F)(F)c1cccc(NC(=S)Nc2cccc(Cl)c2)c1] |
| N-(3-chloro-4-fluorophenyl)-N'-(2-methoxy-4-nitrophenyl)thiourea | 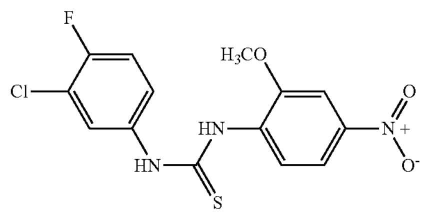 |
| 4-({[3-chloro-4-fluorophenyl]amino}-carbonothioyl)amino-N-ethylbenzenesulfonamide | 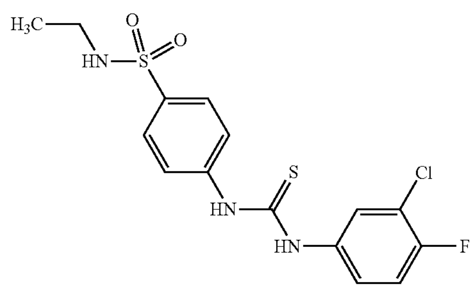 [SMILES: CCNS(=O)(=O)c1ccc(NC(=S)Nc2ccc(F)c(Cl)c2)cc1] |
| 2-[({2-[(2-chlorobenzyl)oxy]-1-naphthyl}methyl)amino]ethanol hydrochloride | 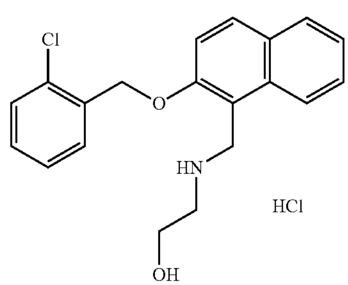 [SMILES: OCCNCc1c(OCc2ccccc2Cl)ccc2ccccc12 ; Cl] |
| 17-(4-bromophenyl)-17-azapentacyclononadeca-2,4,6,9,11,13-hexaene-16,18-dione | 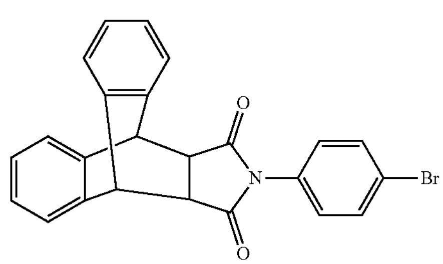 [SMILES: O=C1C2C3c4ccccc4C(c4ccccc43)C2C(=O)N1c1ccc(Br)cc1] |

TABLE 1-continued

Persister cell inhibitors and their structures that were identified in the initial screen

| Name | Structure |
|---|---|
| N-(3-chloro-4-fluorophenyl)-N'-3-pyridinylthiourea | 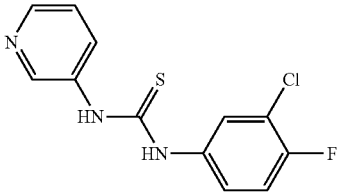 [SMILES: Fc1ccc(NC(=S)Nc2cccnc2)cc1Cl] |
| N-(4-chlorobenzyl)-N'-4-pyridinylthiourea | 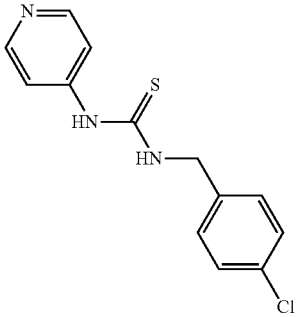 [SMILES: S=C(NCc1ccc(Cl)cc1)Nc1ccncc1] |
| 5-bromo-N-{2-[(4-methylphenyl)thio]ethyl}-2-thiophenesulfonamide | 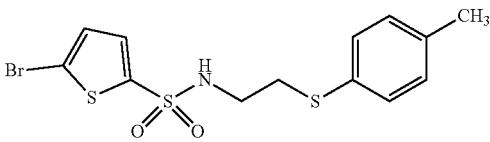 [SMILES: Cc1ccc(SCCNS(=O)(=O)c2ccc(Br)s2)cc1] |
| N'-(3,5-dichloro-2-hydroxybenzylidene)-2-oxo-4-phenyl-3-pyrrolidinecarbohydrazide | 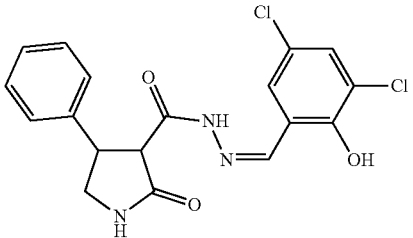 [SMILES: O=C1NCC(c2ccccc2)C1C(=O)N/N=C\c1cc(Cl)cc(Cl)c1O] |

3.2|NPIMA Kills *E. coli* Exponential Cells

Figure 9:
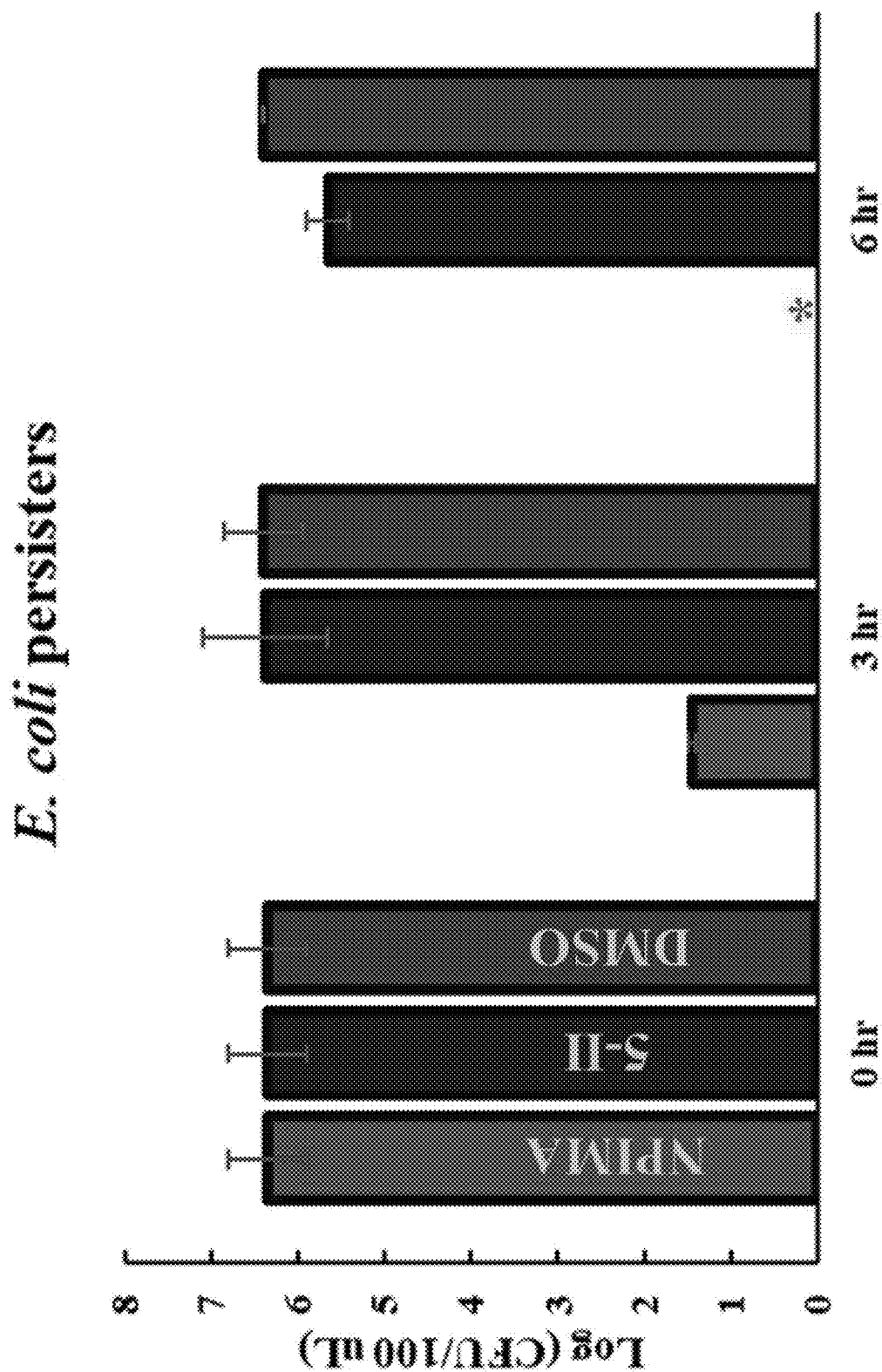
FIG. 9. NPIMA kills naturally-occurring *E. coli* persister cells. Survival of *E. coli* with 5-iodoindole and solvent negative control (DMSO) also shown. Asterisk (*) indicates no viable cells were detected. The persister cells were harvested at stationary-phase of *E. coli* (turbidity of 6.0 at 600 nm) and non-persister cells were removed by treatment.

Since NPIMA was identified as killing persister cells, we tested whether it is effective on both persister cells and exponential cells. The MIC for NPIMA with *E. coli* was determined to be 100 μM (15 μg/ml) (Table 2); hence, we tested it at 100 μM (1 MIC) and found NPIMA eradicates exponentially-growing *E. coli* within 3 hr (FIG. 2a). Furthermore, NPIMA (100 μM) also eradicated *E. coli* persisters in 6 hr (FIG. 3a). Critically, persister cells generated with only ampicillin treatment ("natural persisters") were killed in an identical manner (FIG. 9), which confirms our rifampicin-treatment persister model. Therefore, NPIMA is kills both persister and exponentially-growing *E. coli*.

TABLE 2

MICs (mM) for 5-iodoindole, NPIMA, and cisplatin

| Strain | 5-Iodoindole | NPIMA | Cisplatin |
|---|---|---|---|
| *Escherichia coli* BW251113 | 2 | 0.1 | 0.3 |
| *Staphylococcus aureus* | 2 | 0.1 | 1 |
| *Pseudomonas aeruginosa* PA14 | 2 | 0.25 | 0.15 |

Note:

Values for cisplatin are from (Chowdhury, Wood, et al., 2016).

Abbreviations: MIC, minimum inhibitory concentration; NPIMA, 5-nitro-3-phneyl-1H-indol-2-yl-methylamine hydrochloride.

3.3|NPIMA Damages the Cell Membrane and Causes Cell Lysis

Figure 4:
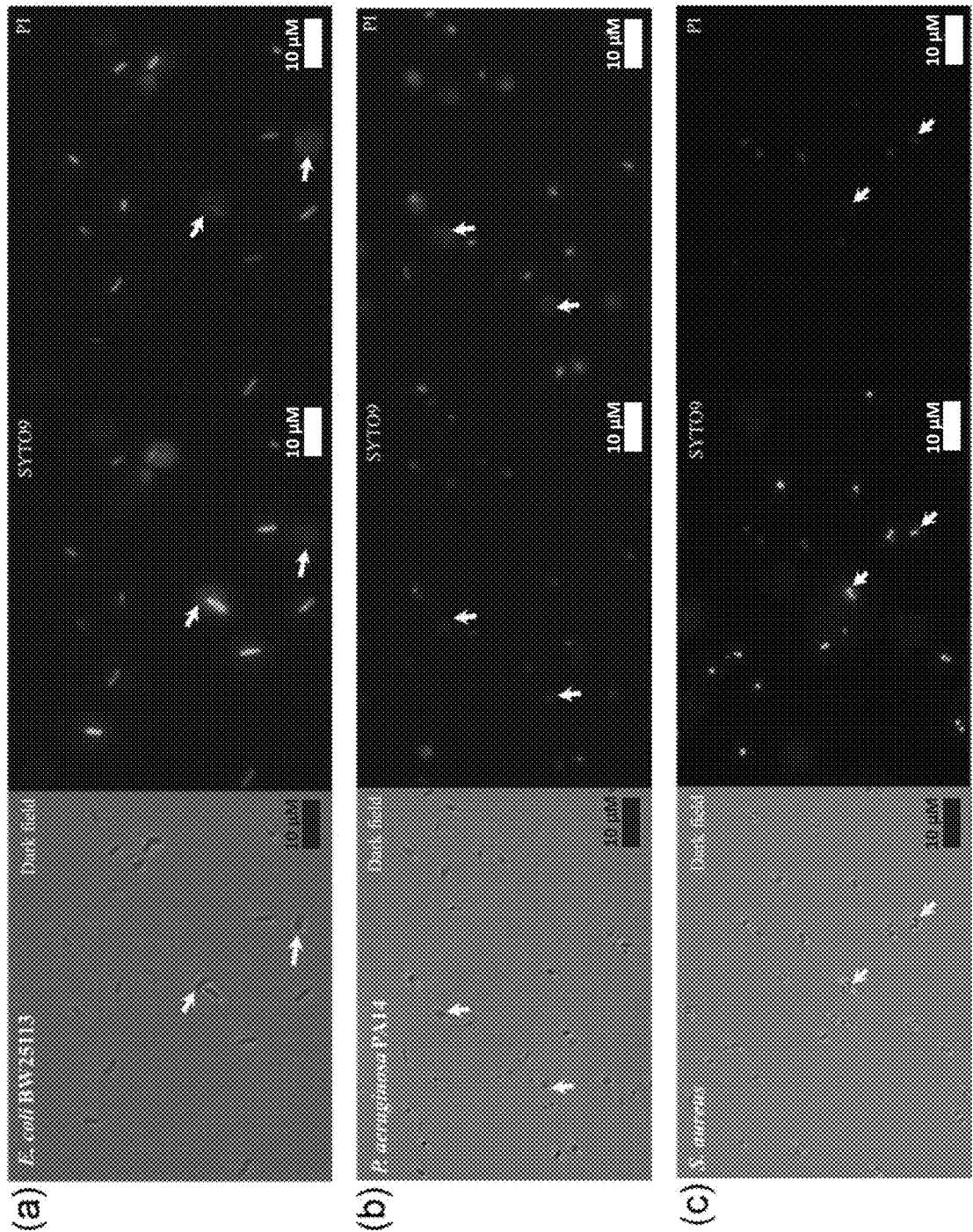
FIG. 4. NPIMA lyses *Escherichia coli, Pseudomonas aeruginosa*, and *Staphylococcus aureus*. LIVE/DEAD staining of (a) *E. coli* BW251 13 after 0.75 hr, (b) *P. aeruginosa* PA14 after 1 hr, and (c) *S. aureus* after 1 hr treatment with NPIMA at 100 μM. Left shows dark field, middle shows all cells stained by Syto9, and right shows dead cells stained by propidium iodide. White arrows indicate lysed cells. Representative images are shown. Scale bar=10 μM. NPIMA, 5-nitro-3-phenyl-1H-indol-2-ylmethylamine hydrochloride.
Figure 5:
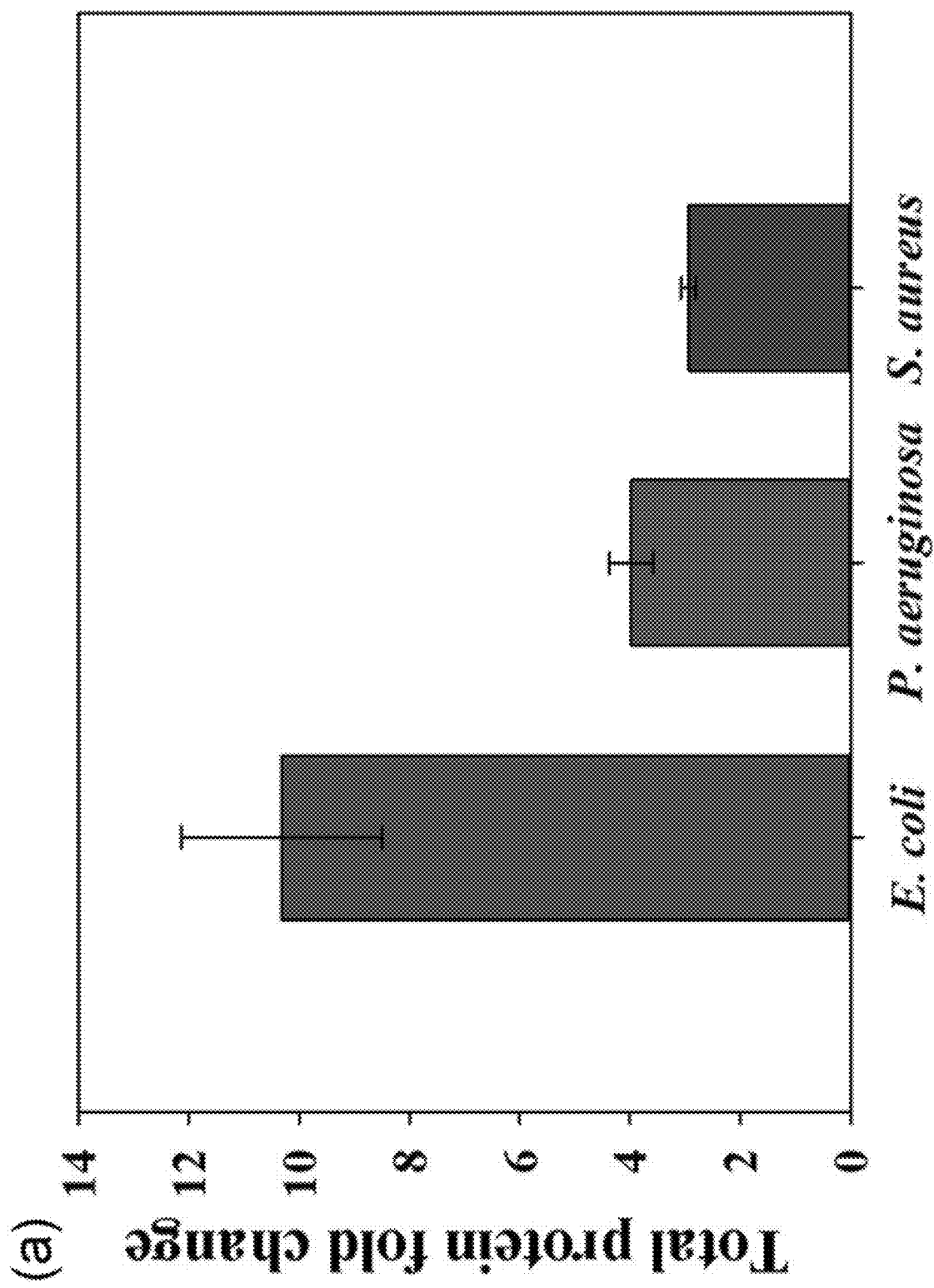
FIG. 5. NPIMA lyses *Escherichia coli, Pseudomonas aeruginosa*, and *Staphylococcus aureus*. Total protein (a) and DNA (b) found in supernatants as evidence of cell lysis after treatment of cells at a turbidity of 0.8 at 600 nm with 100 μM NPIMA after 1 hr for *E. coli* and *P. aeruginosa* and 6 hr for *S. aureus*. NPIMA, 5-nitro-3-phenyl-1H-indol-2-yl-methylamine hydrochloride.
Figure 5:
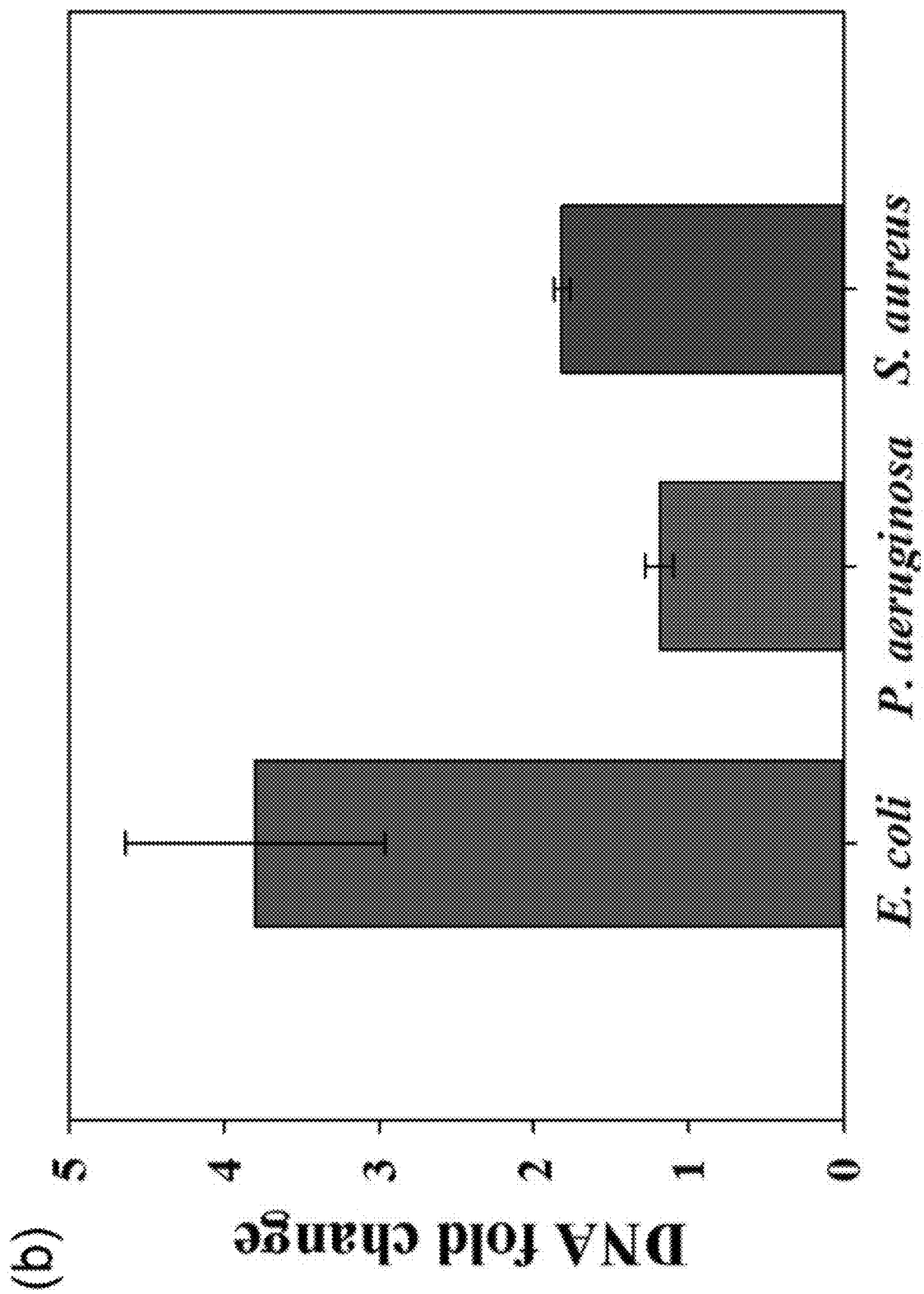
Figure 6:
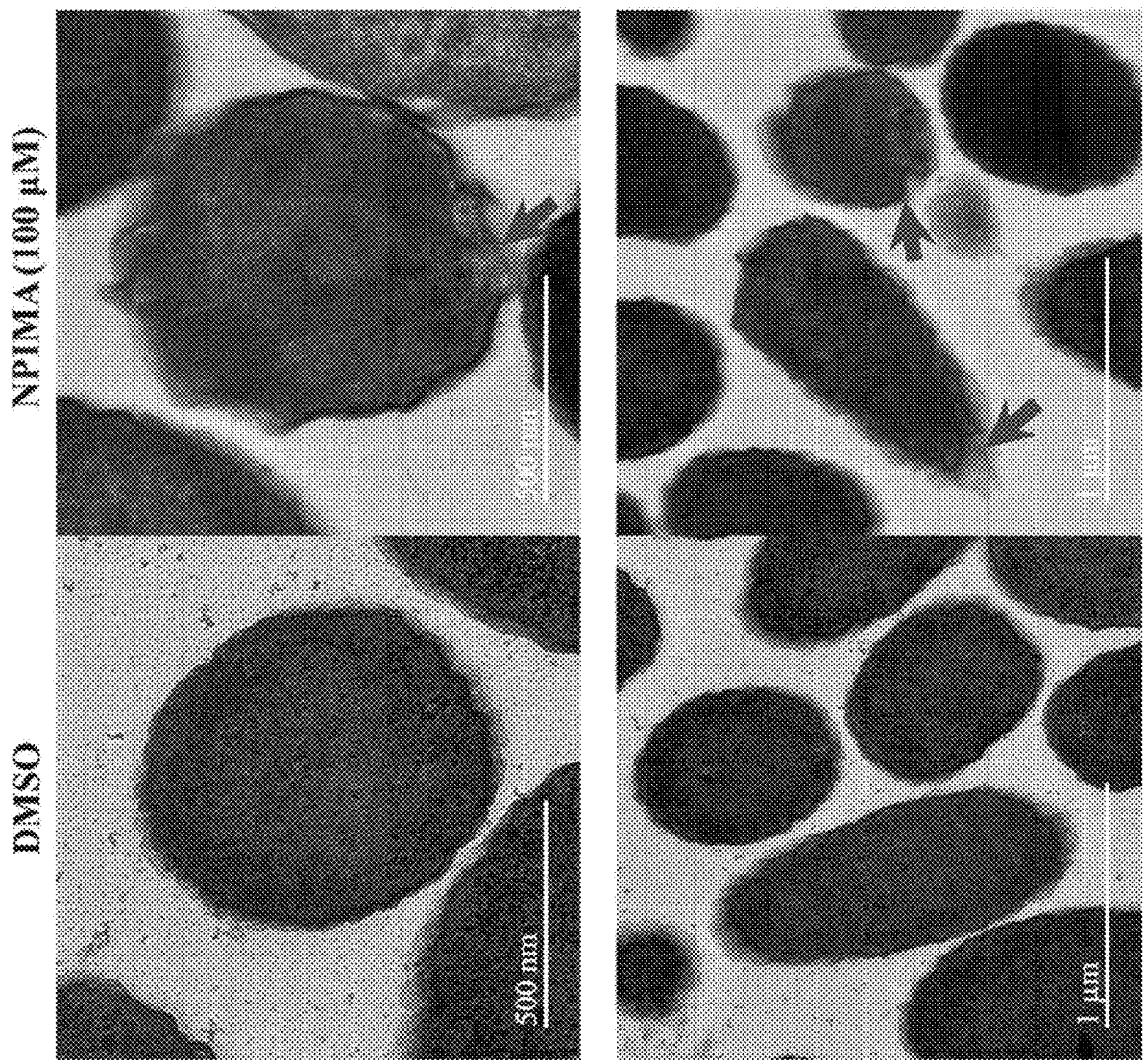
FIG. 6. NPIMA damages the *Escherichia coli* cell membrane. Transmission electron microscopic (TEM) images of *E. coli* BW25113 after NPIMA (100 μM) treatment for 40 min. Two representative images are shown. The arrow indicates membrane damage. NPIMA, 5-nitro-3-phenyl-11H-indol-2-ylmethylamine hydrochloride.

To initially explore how NPIMA kills cells, we treated exponentially-growing E. coli BW25113 cells with 100 µM NPIMA and stained with the LIVE/DEAD kit. Remarkably, we found that cells treated with 100 µM NPIMA lysed as evidenced by the extracellular DNA seen surrounding cells that was stained by both Syto9 and propidium iodide of the LIVE/DEAD kit (FIG. 4); note there were no dead cells seen with the solvent control (DMSO). Corroborating the cells lysis seen with the DNA dyes, treatment of exponentially-growing E. coli with 100 µM NPIMA for 1 hr led to both a 10±2 increase in total cell protein in supernatants as well as a 3.8±0.8 increase in DNA in the supernatants compared to the addition of DMSO alone (FIG. 5). To investigate further the cell lysis caused by NPIMA, we used transmission electron microscopy and found clear cell envelope damage (FIG. 6). Together, these five lines of evidence show NPIMA lyses E. coli cells.

3.4|NPIMA is More Effective with E. coli Persisters than 5-Iodoindole

Since 5-iodoindole is the most effective indigo derivative for killing E. coli persister cells (kills 99.993% of persisters at 1 mM; Lee et al., 2016), we compared the effectiveness of this compound to NPIMA. Using both compounds at 100 µM, as indicated above, NPIMA eradicated both exponential (FIG. 2a), persister cells (FIG. 3a) of E. coli whereas 5-iodoindole was much less effective. Corroborating these results, we found the MIC for 5-iodoindole to be 2 mM (Table 2)

3.5|NPIMA has Broad Activity

We also tested whether NPIMA was effective at killing P. aeruginosa and S. aureus persister cells. At 100 µM, NPIMA eradicated exponentially-growing P. aeruginosa PA14 cells in 6 hr (FIG. 2b) as well as eradicated P. aeruginosa persister cells in 3 hr (FIG. 3b). Similarly, NPIMA eradicated S. aureus cells at 200 µM in 3 hr (FIG. 2c). In contrast, 5-iodoindole was ineffective with both P. aeruginosa at 100 µM and S. aureus at 200 µM. Corroborating these results, the MIC for 5-iodoindole for P. aeruginosa was 2 mM versus 0.25 mM for NPIMA, and the MIC for 5-iodoindole for S. aureus was 2 mM versus 0.1 mM for NPIMA (Table 2). Therefore, NPIMA is highly effective with P. aeruginosa and S. aureus.

3.6|NPIMA Lyses S. aureus and P. aeruginosa

We also investigated the mechanism by which NPIMA kills S. aureus and P. aeruginosa persister cells. Using the LIVE/DEAD staining Kit, we found after 1 hr, 100 µM NPIMA killed 27% for the S. aureus cells (FIG. 4c). Critically, we also saw evidence of S. aureus cell lysis in the form of hazy staining with Syto9 only around cells with NPIMA. Hence, we checked for the presence of extracellular DNA and protein as evidence of lysis and found 2.9±0.1-fold total protein and 1.82±0.05-fold DNA released due to 100 µM NPIMA treatment after 6 hr compared with the addition of DMSO alone (FIG. 5).

Similar to S. aureus, 100 µM NPIMA also lysed P. aeruginosa as indicated by LIVE/DEAD staining that shows distinct extracellular DNA after treating for 1 hr for both Syto9 and propidium iodide (FIG. 4b); however, unlike with S. aureus, all (100%) of the P. aeruginosa cells were killed in 1 hr. Therefore, we checked for the presence of extracellular DNA and protein as evidence of lysis and found a 1.19±0.09-fold increase in DNA and a 4.0±0.4-fold total protein released due to 100 µM NPIMA treatment after 1 hr compared to the addition of DMSO alone (FIG. 5). Hence, as with E. coli, NPIMA lyses both Gram-positive S. aureus and Gram-negative P. aeruginosa.

3.7|Wound Model

Figure 10:
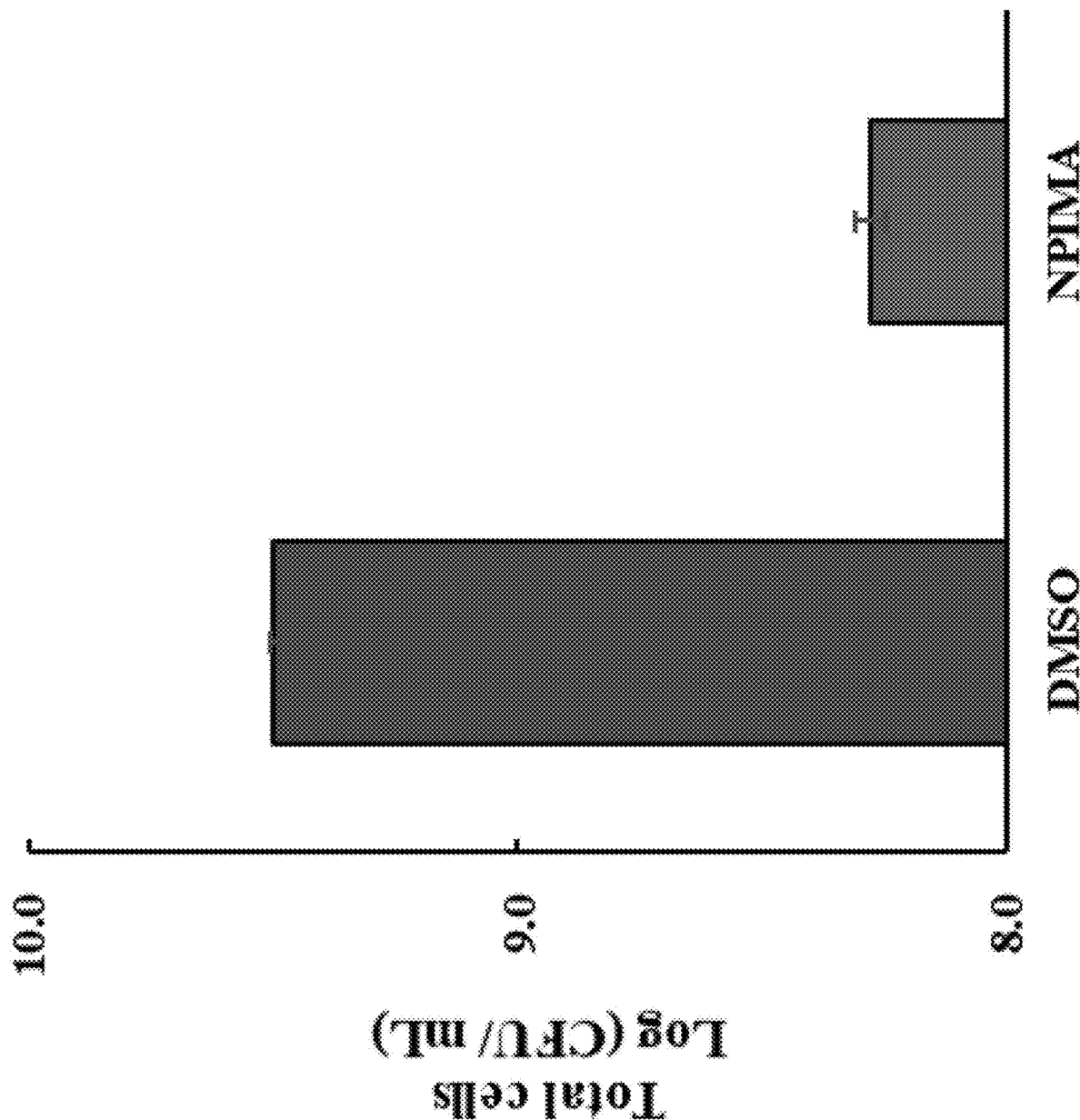
FIG. 10. NPIMA kills *S. aureus* and *P. aeruginosa* in a wound model. Survival of total cells (*P. aeruginosa*+*S. aureus*) in the wound model after treatment with NPIMA for 6 h. The left bar is the solvent (DMSO) negative control.

To test NPIMA against the pathogen P. aeruginosa and S. aureus in a realistic infection model, we chose the in vitro Lubbock chronic wound pathogenic biofilm model (Sun et al., 2008), since both pathogens are frequently found together in wounds (DeLeon et al., 2014) and this model mimics the conditions of polyclonal infections. We found NPIMA (0.5 mM) reduced the total viable number of cells of S. aureus and P. aeruginosa in the wound model 10-fold in 6 hr compared to the DMSO solvent control (FIG. 10).

Figure 7:
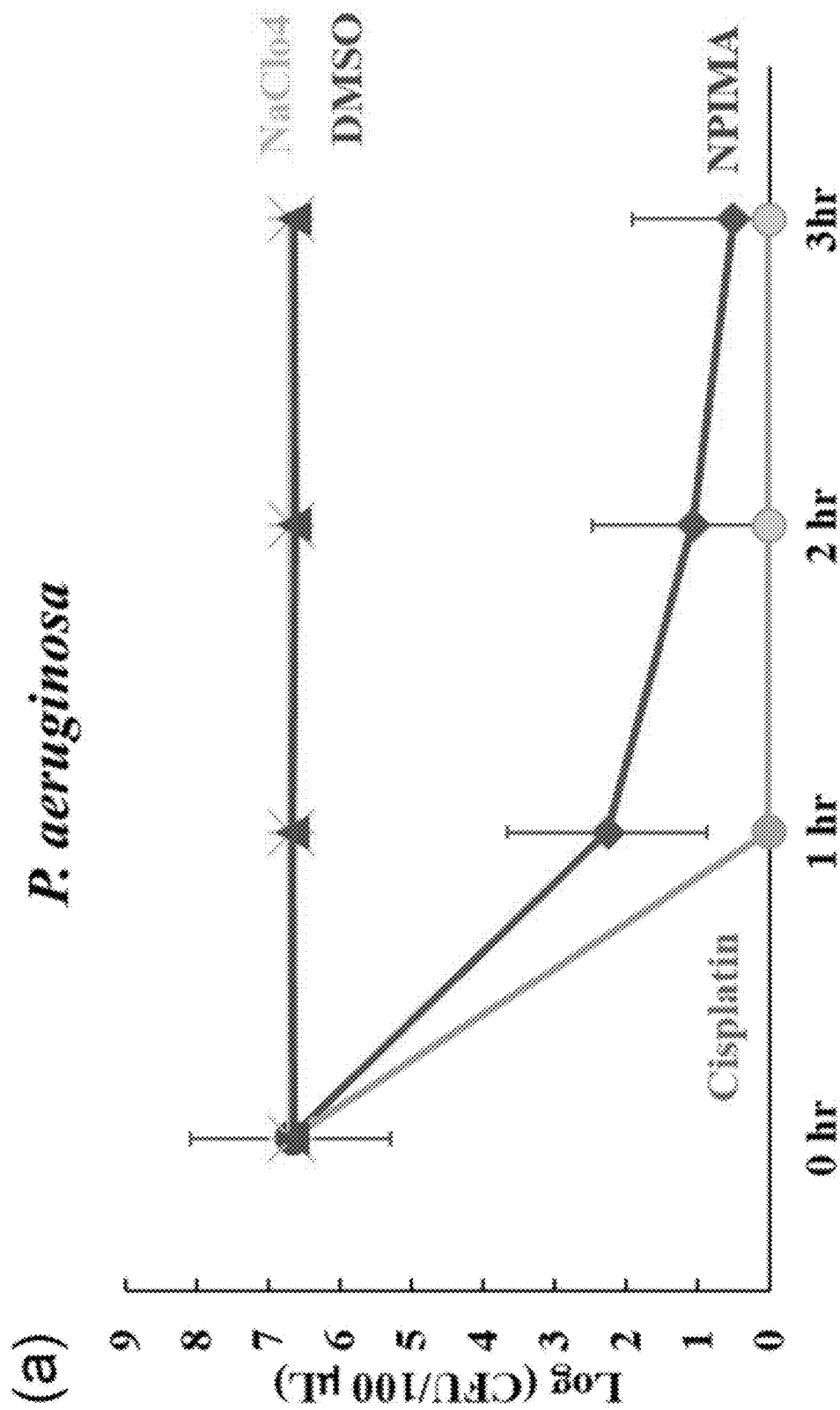
FIG. 7. NPIMA compared width cisplatin for killing *Pseudomonas aeruginosa, Escherichia coli*, and *Staphylococcus aureus*. Survival of exponentially-growing cells of *P. aeruginosa* PA14 (a), *E. coli* (b), and *S. aureus* (c) treated with one MIC of NPIMA (+) and cisplatin (e) for 3 hr in PBS. DMSO (Δ) and NaClO4 (*) were used as a negative controls. MIC, minimum inhibitory concentration; NPIMA, 5-nitro-3-phenyl-1H-indol-2-yl-methylamine hydrochloride.
Figure 7:
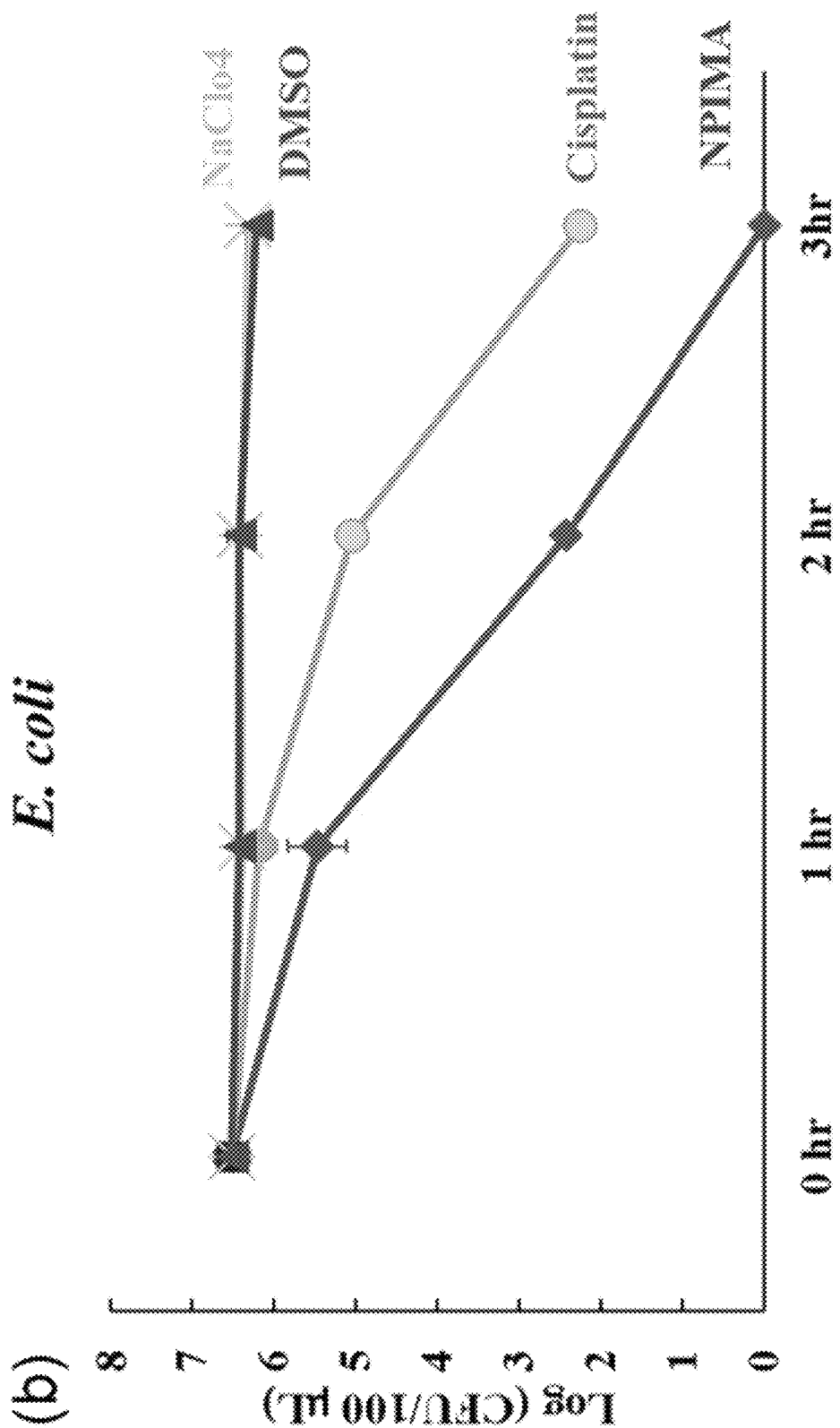
Figure 7:
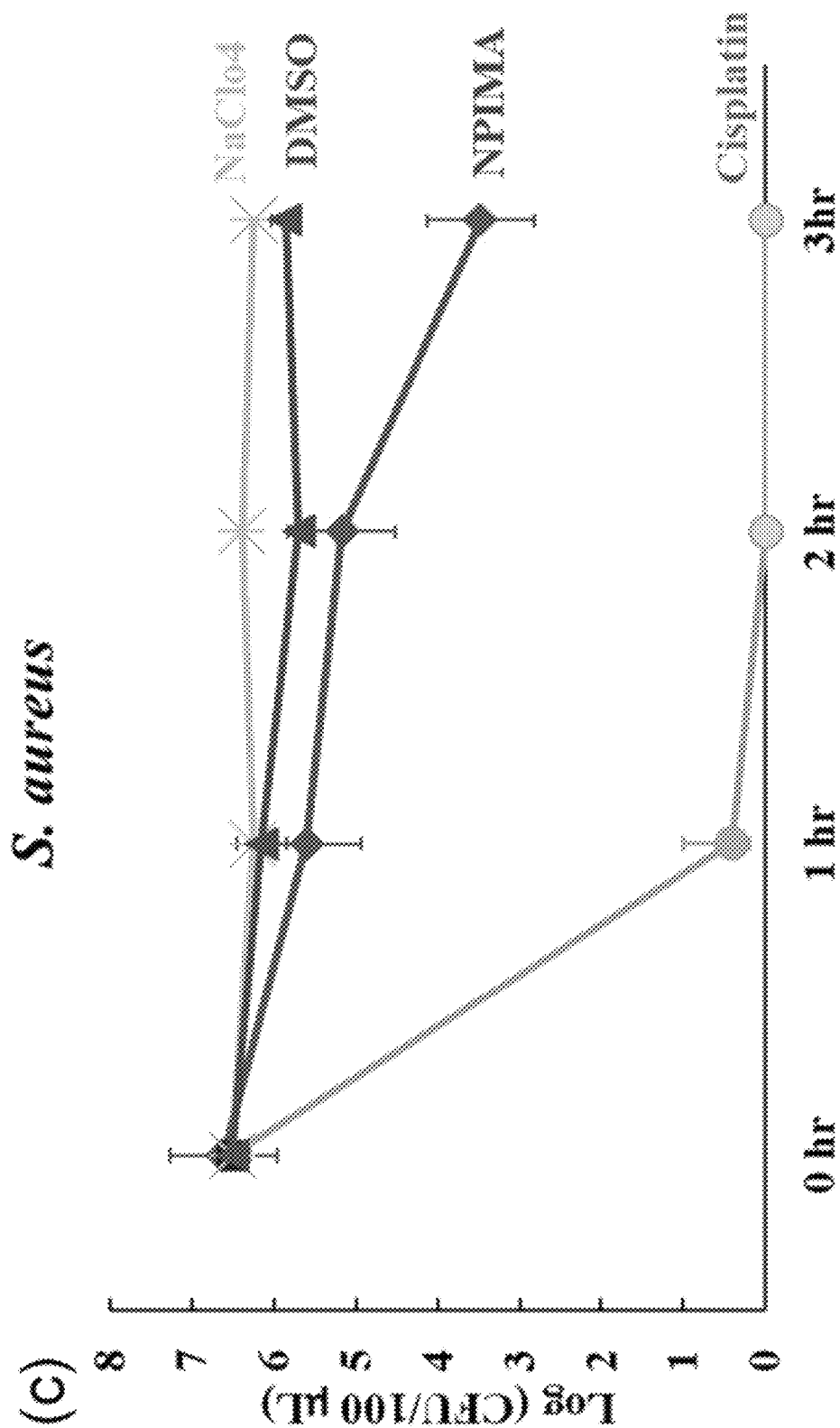

3.8|NPIMA is More Effective for E. coli but Less Effective for P. aeruginosa and S. aureus than the DNA Cross-linker Cisplatin To gauge its effectiveness, we compared NPIMA to cisplatin, which has been shown to be effective for killing P. aeruginosa (Chowdhury, Wood, et al., 2016; Yuan et al., 2018), with each compound used at one MIC (Table 2). As shown in FIG. 7a, cisplatin eradicated P. aeruginosa cells in 1 hr whereas NPIMA was less effective. For E. coli (FIG. 7b), NPIMA was more effective than cisplatin, but for S. aureus (FIG. 7c), NPIMA was less effective than cisplatin.

3.9|Resistance

To test if E. coli could obtain resistance easily to NPIMA, cells were propagated daily in LB with 0.25 MIC of NPIMA (25 µM) for 7 days. After 7 days, the sequentially-propagated E. coli cells were contacted with LB with 1 MIC of NPIMA (100 µM) and incubated overnight to allow any putative resistant cells to grow and increase the turbidity. Critically, all of the E. coli cells were killed. Hence, resistance to NPIMA does not occur readily.

3.10|Structure Activity Relationships

Figure 8:
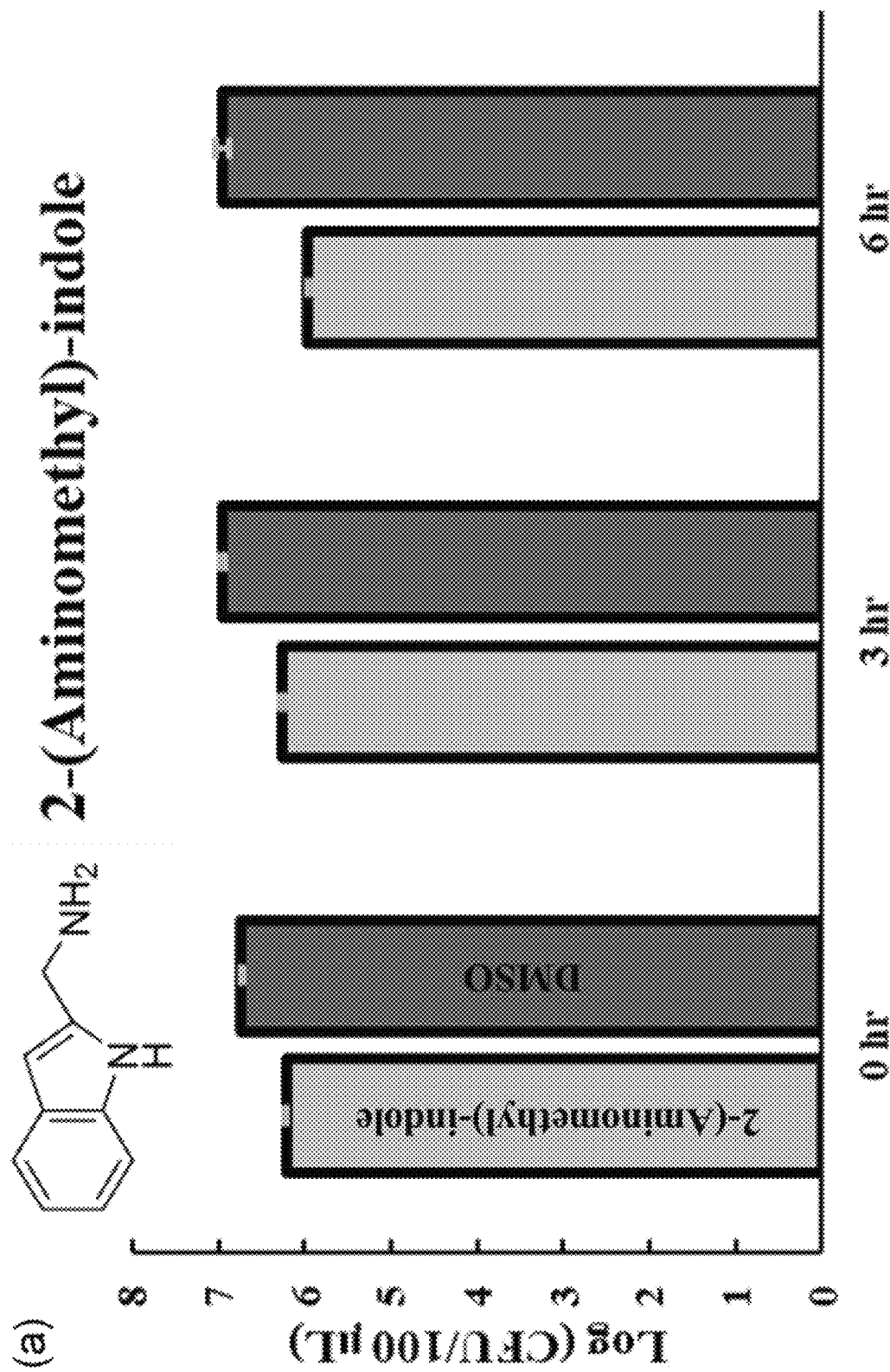
FIG. 8. NPIMA structure function relationships. Exponential cells of *Escherichia coli* BW25113 were treated with (a) 2-(aminomethyl) indole, and (b) 2-methyl-5-nitro-3-phenyl-1H-indole for 6 hr. NPIMA, 5-nitro-3-phenyl-1Hindol-2-yl-methylamine hydrochloride.
Figure 8:
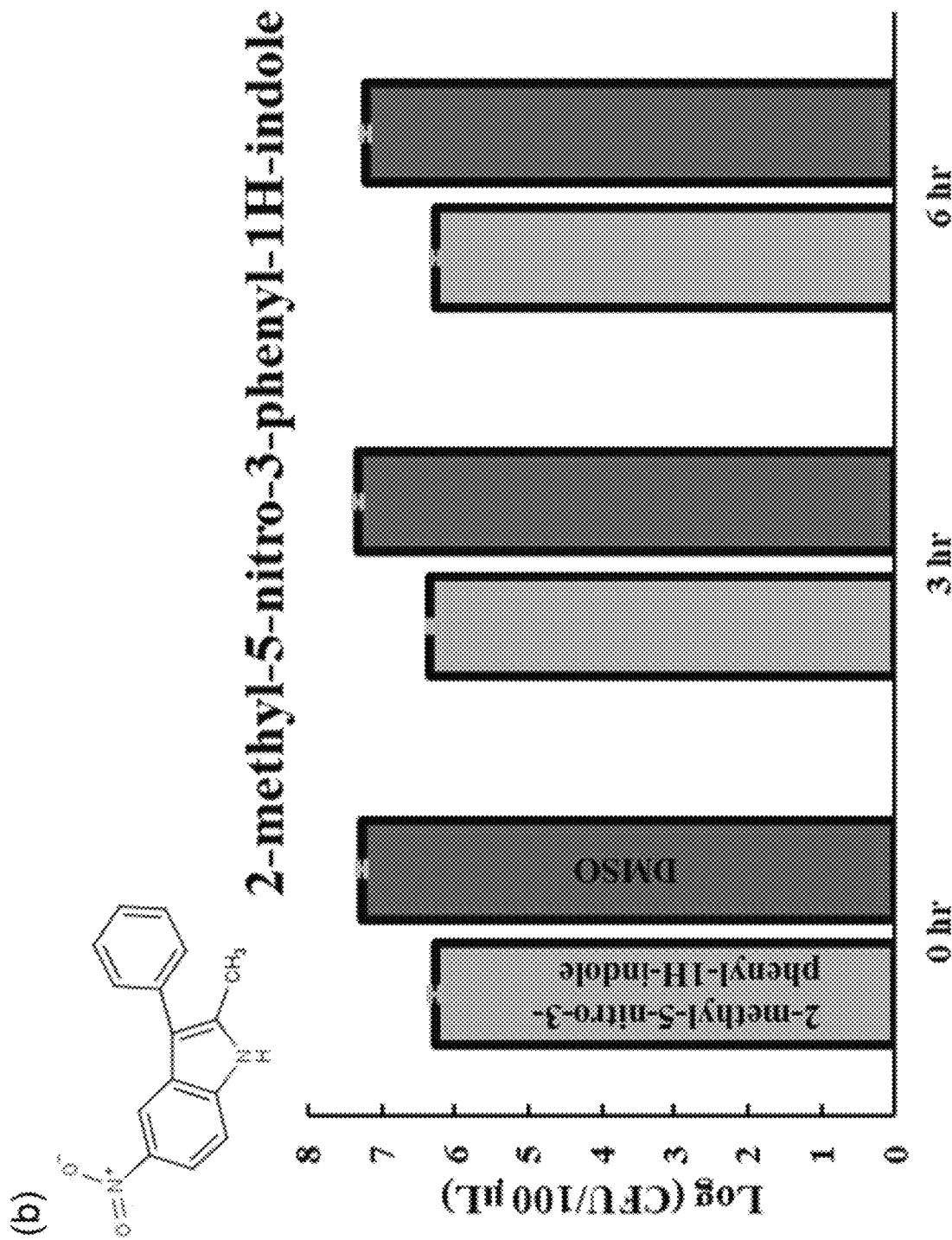

To discern insights about the importance of the three substituents on the indole ring of NPIMA, we tested the importance of both the nitro and phenyl groups by assaying the killing of 2-(aminomethyl)-indole with E. coli and found 2-(aminomethyl)-indole (100 µM) is unable to kill E. coli (FIG. 8). In addition, 2-methyl-5-nitro-3-phenyl-1H-indole was used to ascertain the importance of the amine group, and we found 2-methyl-5-nitro-3-phenyl-1H-indole (100 µM) is unable to kill E. coli (FIG. 8). Hence, all three substituents are important for NPIMA activity.

3.11|NPIMA Cytotoxicity

Figure 11:
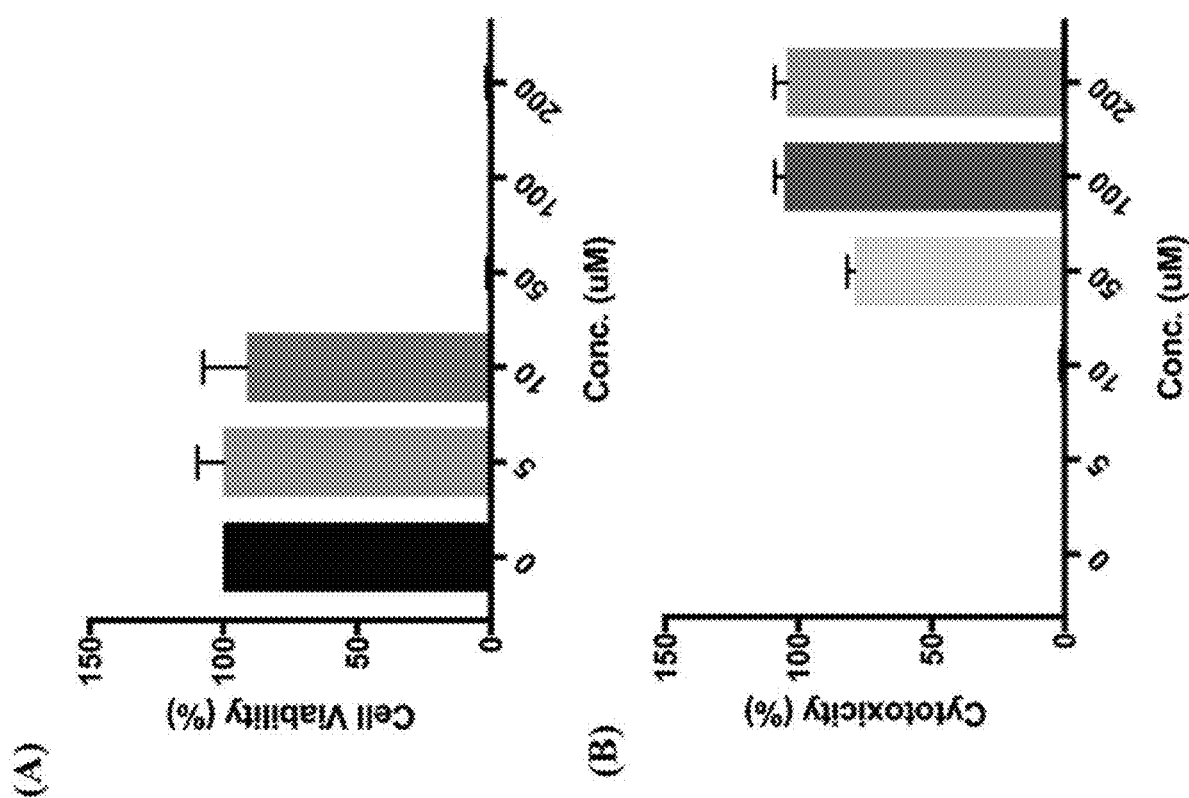
FIG. 11. Cytotoxicity of NPIMA with HT-29 cells. (A) Cell viability was measured via a CCK-8 assay. (B) Cytotoxicity was measured with various concentrations of NPIMA (0, 5, to each well along with—in 98) for 24 h. Cell viability was measured at 450 nm, and cell toxicity was measured at 492 nm and a reference wavelength (620 nM) was used.

To determine the cytotoxicity of NPIMA, we performed both an LDH assay and CCK-8 assay with human cells. NPIMA was not toxic at 5 and 10 µM but showed toxicity in both tests at concentrations of 50 µM and higher (FIG. 11).

4|Discussion

Previously, we demonstrated through two independent approaches that cell signaling through indole decreases persistence (Iu et al., 2015; Kwan, Osbourne, et al., 2015). Specifically, by producing the RNase toxin YafQ of the E. coli YafQ/DinJ TA system, we found YafQ cleaves the mRNA of tryptophanase, which produces indole from tryptophan; hence, there is less indole production and a dramatic increase in persistence (Hu et al., 2015). Additionally, we showed that producing the phosphodiesterase DosP reduces cAMP concentrations which in turn reduces tryptophanase and indole production which leads to a dramatic increase in persistence (Kwan, Osbourne, et al., 2015).

Figure 2:
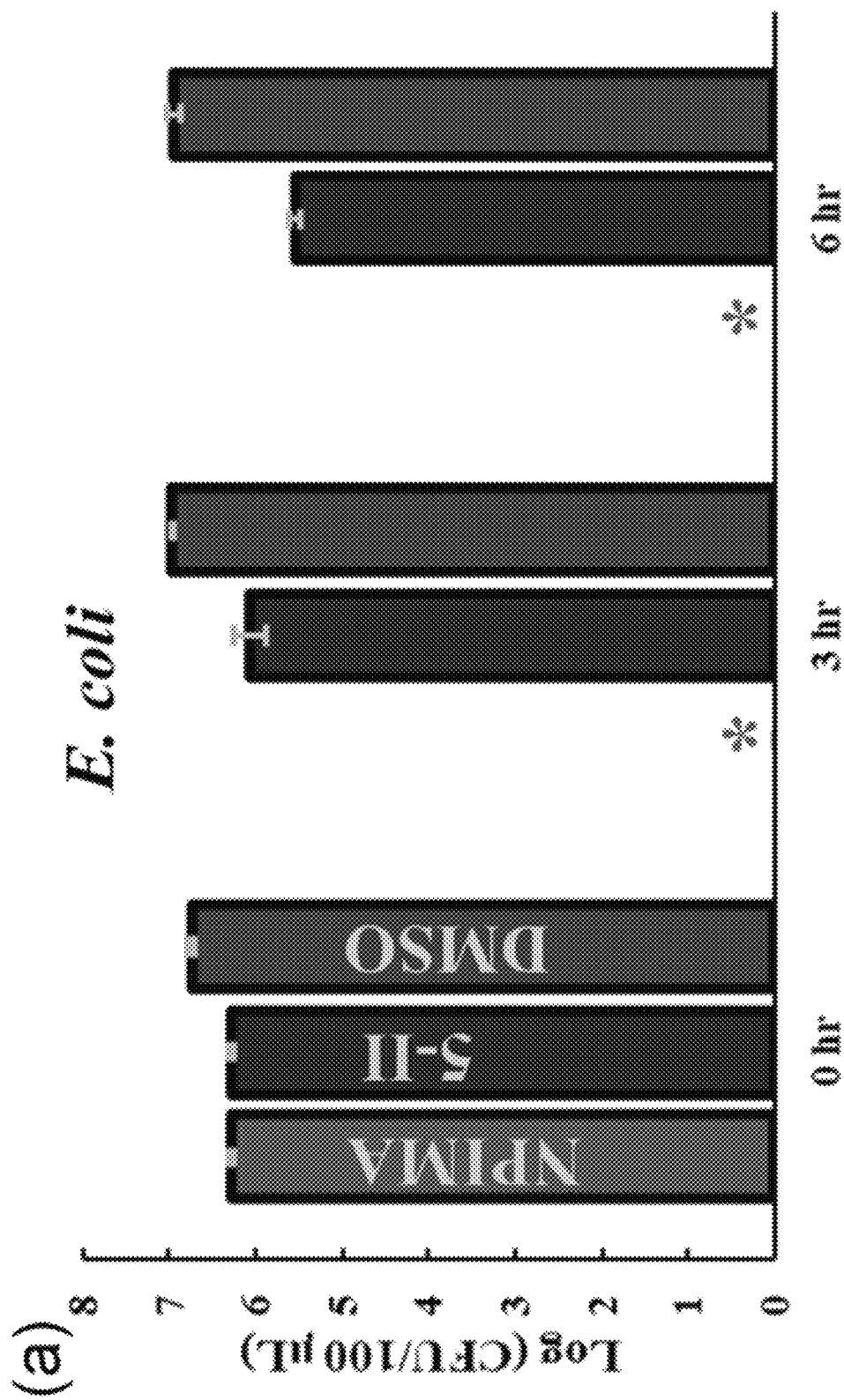
FIG. 2. NPIMA eradicates *Escherichia coli*, *Pseudomonas aeruginosa*, and *Staphylococcus aureus* exponential cells. Survival after 6 hr for (a) *E. coli* BW25113 with NPIMA and 5-iodoindole at 100 µM, (b) *P. aeruginosa* PA14 with NPIMA and 5-iodoindole at 100 µM, and (c) *S. aureus* with NPIMA and 5-iodoindole at 200 µM. Asterisk indicates no viable cells detected. NPIMA, 5-nitro-3-phenyl-1H-indol-2-yl-methylamine hydrochloride.
Figure 2:
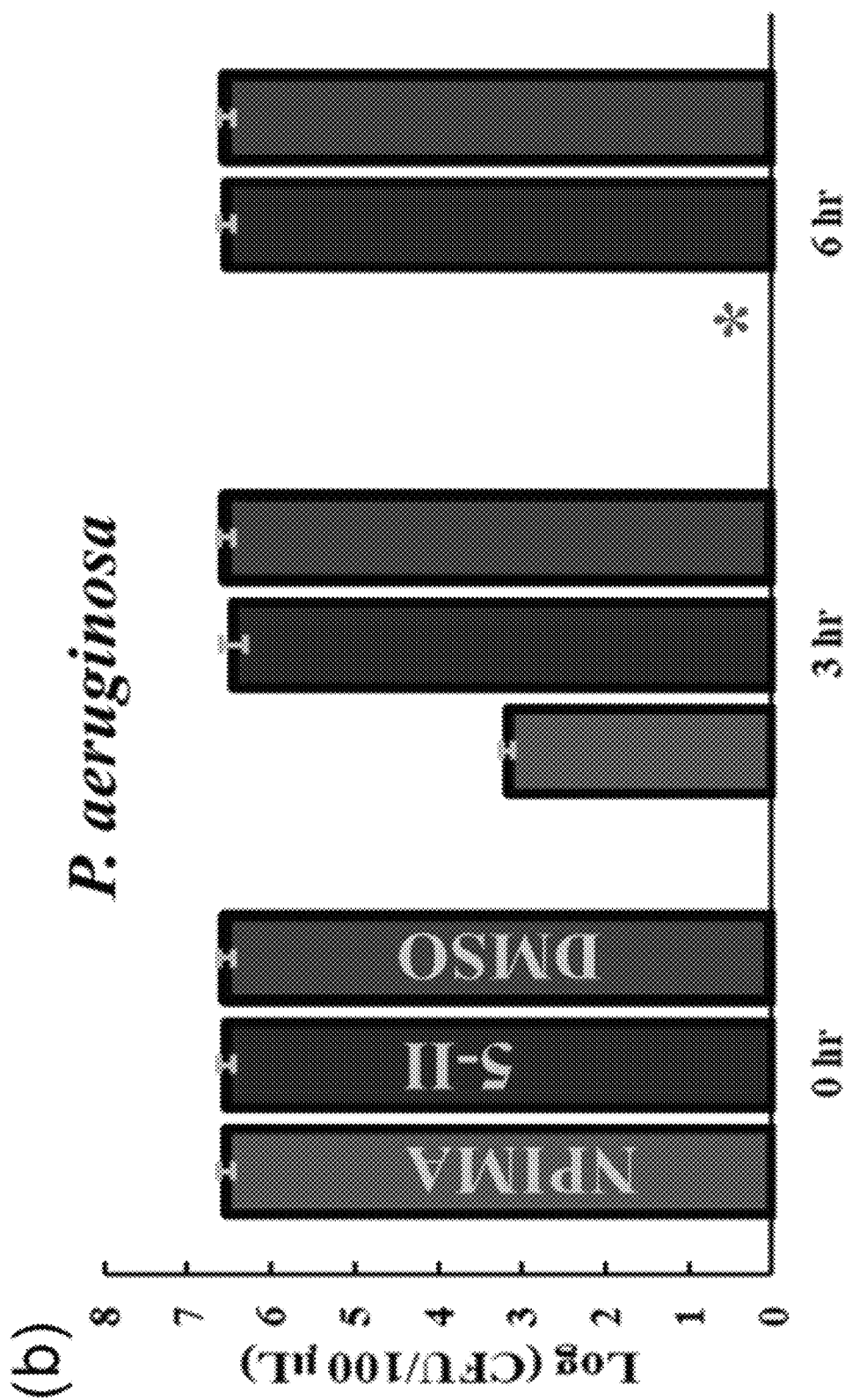
Figure 2:
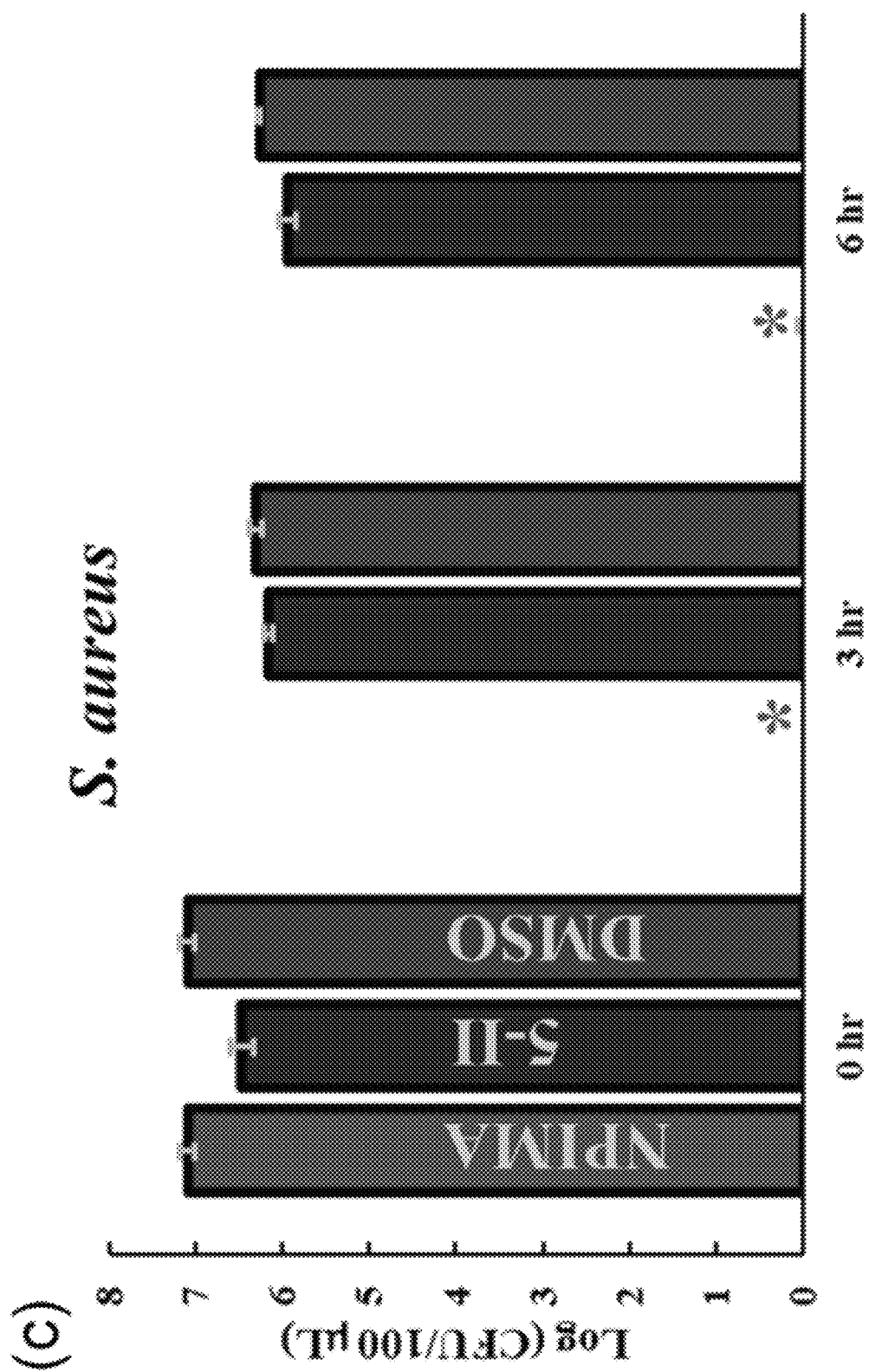
Figure 3:
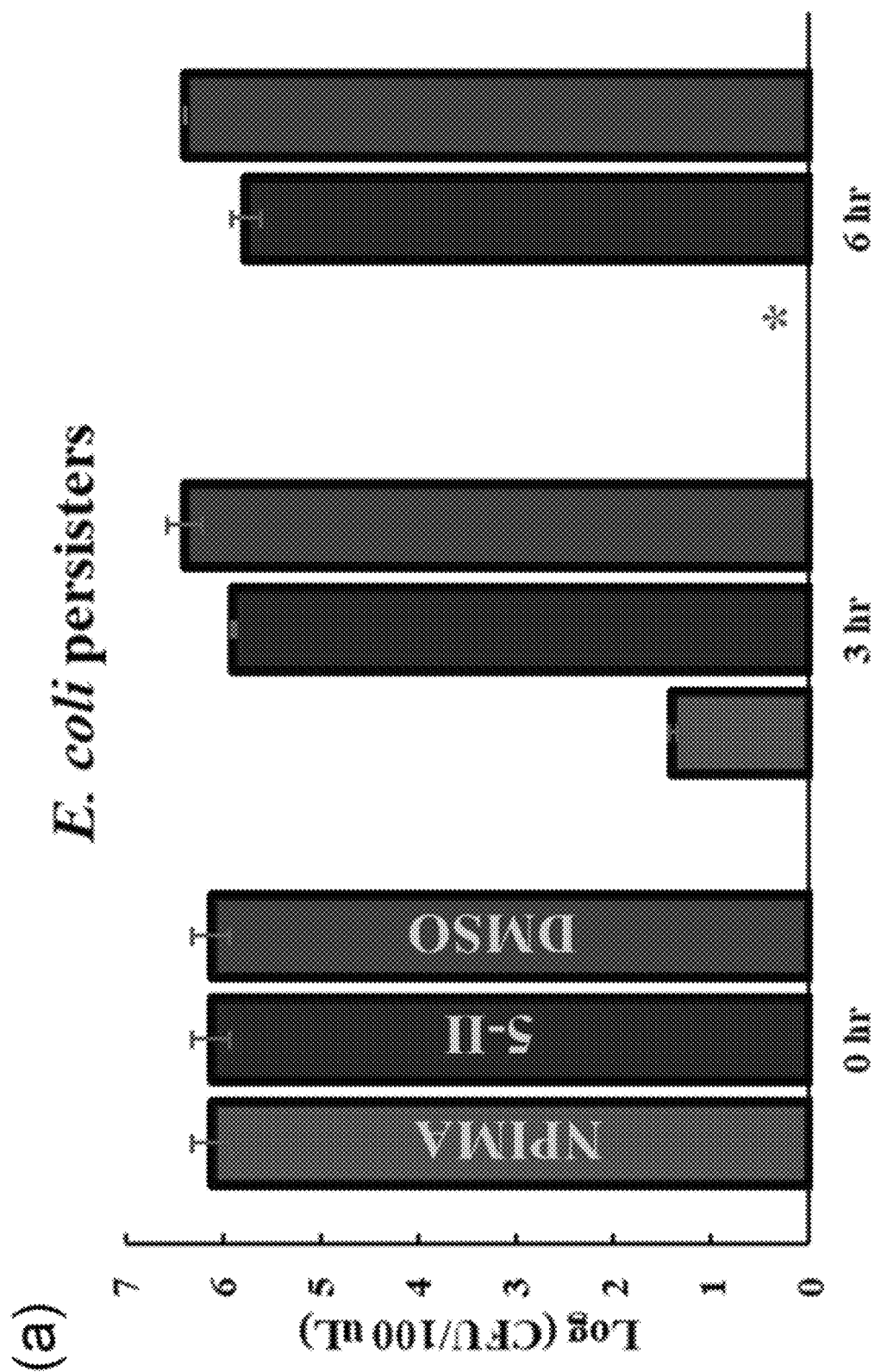
FIG. 3. NPIMA kills *Escherichia coli, Pseudomonas aeruginosa*, persister cells. Survival of (a) *E. coli* BW25113 and (b) *P. aeruginosa* PA14 after treatment with NPIMA (100 μM), 5-iodoindole (5-II, 100 μM), and DMSO for 6 hr. Asterisk indicates no viable cells detected. DMSO, dimethyl sulfoxide; NPIMA, 5-nitro-3-phenyl-1H-indol-2-yl-methylamine hydrochloride.
Figure 3:
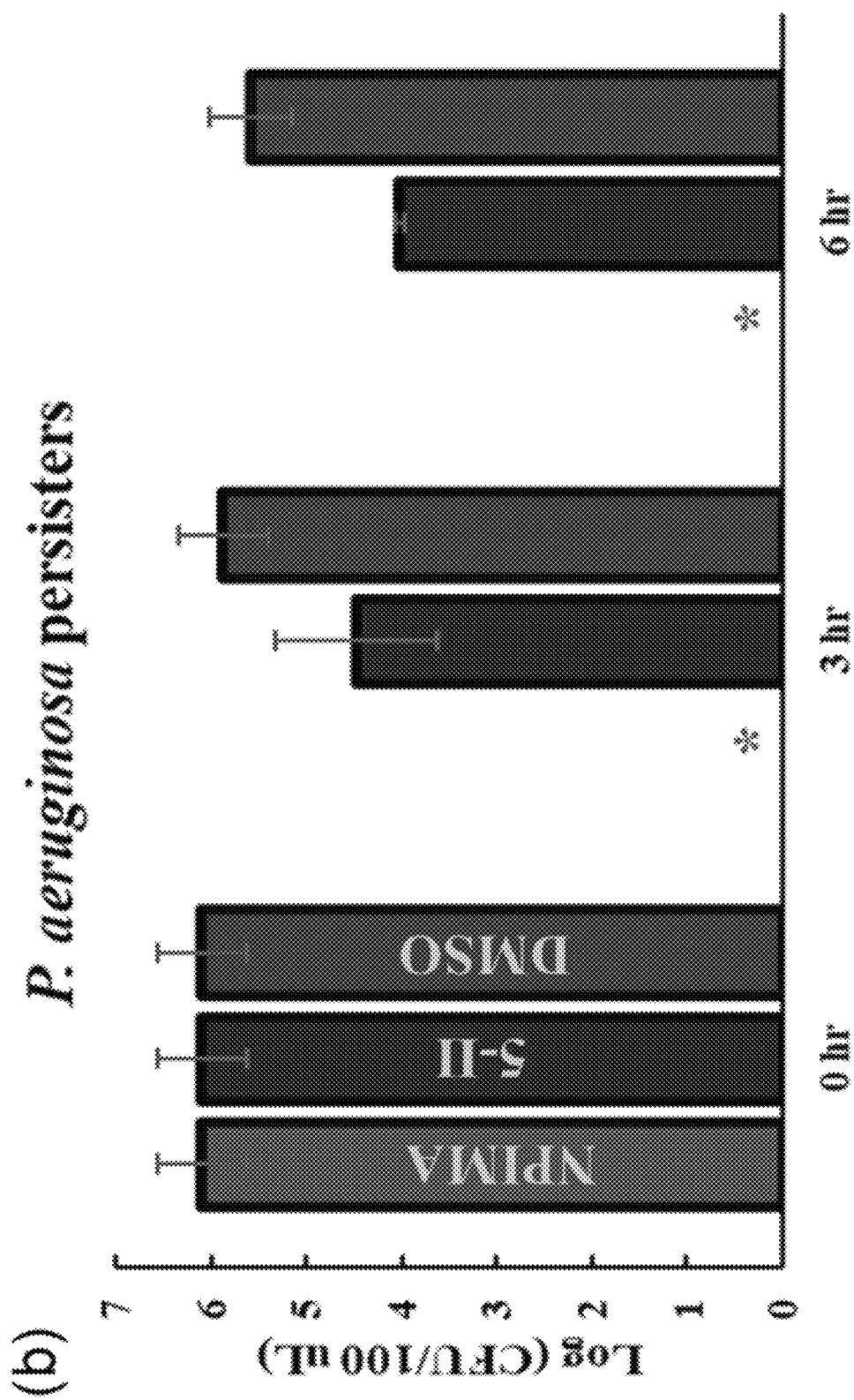

Also, direct addition of both indole and halogenated indoles reduces persistence (Lee et al., 2016); hence, indole signaling reduces persister cell formation. For compounds to kill persister cells by corrupting cytosolic functions, they must be able to enter the cytosol of the dormant cell through passive diffusion, like the DNA-crosslinkers mitomycin C (Kwan, Chowdhury, et al., 2015; Wood, 2016) and cisplatin (Chowdhury, Wood, et al., 2016) or they can attack the outside of the cell by damaging the membrane, like retinoids (Kim, Zhu, et al., 2018). Critically, we found here that NPIMA, a substituted indole, reduces persistence, not by changing indole signaling and altering tryptophanase activity (Hu et al., 2015; Kwan, Osbourne, et al., 2015), but by killing cells through lysis from membrane damage (FIGS. 4-6). This mode of killing was found to be general for both Gram-negative and Gram-positive bacteria since we found NPIMA was effective with *E. coli, P. aeruginosa,* and *S. aureus*. NPIMA is probably less effective in the complete lysis of Gram-positive strains (FIG. 4), which results in the release of cellular protein and DNA, due to the protective cell wall of Gram-positive strains that Gram-negative strains lack. Although there is less lysis of Gram-positive *S. aureus*, NPIMA kills *S. aureus* as well as *E. coli* (FIG. 2); hence, complete lysis of Gram-positive strains must not be necessary for NPIMA to cause cell death. Furthermore, comparing Gram-negative strains, actively growing *P. aeruginosa* was lysed (FIGS. 4 and 5) and killed (FIG. 2) less effectively than actively-growing *E. coli*, most likely due to the innate resistance of *P. aeruginosa* due to its active efflux (Chen et al., 2010). However, NPIMA was able to kill the most recalcitrant of cells, persister cells, of all three bacteria since it eradicated the generated persister cells of *E. coli* and *P. aeruginosa* equally well (FIG. 3) as well as eradicated the complete population of *S. aureus* cells, which includes persisters (FIG. 2c). Note that due to its cytotoxicity at 50 µM to human cells, NPIMA would have to be used in combination with other antimicrobials or less toxic derivatives need to be found.

Previously, indole (Chimerel, Field, Piñero-Fernandez, Keyser, & Summers, 2012) and the indole derivative 1-geranylindole (Yang et al., 2017) [5-fluoro-[(E)-1-(3,7-dimethylocta-2,6-dien-1-yl)]-3-(piperidin-1-ylmethyl)-1H-indole] have been shown to disrupt the cell membrane. In addition, 1-geranylindole killed nongrowing *Mycobacterium bovis*; however, unlike NPIMA, 1-geranylindole has no effect on *E. coli* (Yang et al., 2017). Therefore, we have discovered a potent substituted indole that is effective in killing a wide-range of bacteria.

REFERENCES

Antonoplis, A., Zang, X., Huttner, M. A., Chong, K. K. L., Lee, Y. B., Co, J. Y., . . . Cegelski, L. (2018). A dual-function antibiotic-transporter conjugate exhibits superior activity in sterilizing MRSA biofilms and killing persister cells. Journal of the American Chemical Society, 140, 16140-16151.

Baba, T., Ara, T., Hasegawa, M., Takai, Y., Okumura, Y., Baba, M., . . . Mori, H. (2006). Construction of *Escherichia coli* K-12 in-frame, single-gene knockout mutants: The Keio collection. Molecular Systems Biology, 2, 2006.0008.

Bertani, G. (1951). Studies on lysogenesis 0.1. The mode of phage liberation by lysogenic *Escherichia coli*. Journal of Bacteriology, 62, 293-300.

Bigger, J. W. (1944). Treatment of staphylococcal infections with penicillin—By intermittent sterilisation. Lancet, 2, 497-500.

Chen, H., Yi, C., Zhang, J., Zhang, W., Ge, Z., Yang, C.-G., & He, C. (2010). Structural insight into the oxidation-sensing mechanism of the antibiotic resistance of regulator MexR. EMBO Reports, 11, 685-690.

Chimerel, C., Field, C. M., Piñero-Fernandez, S., Keyser, U. F., & Summers, D. K. (2012). Indole prevents *Escherichia coli* cell division by modulating membrane potential. Biochimica et Biophysica Acta-Biomembranes, 1818, 1590-1594.

Chowdhury, N., Kwan, B. W., & Wood, T. K. (2016). Persistence increases in the absence of the alarmone guanosine tetraphosphate by reducing cell growth. Scientific Reports, 6, 20519.

Chowdhury, N., Wood, T. L., Martinez-Vázquez, M., Garcia-Contreras, R., & Wood, T. K. (2016). DNA-crosslinker cisplatin eradicates bacterial persister cells. Biotechnology and Bioengineering, 113, 1984-1992.

Conlon, B. P., Nakayasu, E. S., Fleck, L. E., LaFleur, M. D., Isabella, V. M., Coleman, K., . . . Lewis, K. (2013). Activated ClpP kills persisters and eradicates a chronic biofilm infection. Nature, 503, 365-370.

Cruz-Muñiz, M. Y., López-Jacome, L. E., Hernández-Duran, M., Franco-Cendejas, R., Licona-Limón, P., Ramos-Balderas, J. L., . . . Garcia-Contreras. R. (2016). Repurposing the anticancer drug mitomycin C for the treatment of persistent *Acinetobacter baumannii* infections. International Journal of Antimicrobial Agents, 49, 88-92.

Cui, P., Niu, H., Shi, W., Zhang, S., Zhang, W., & Zhang, Y. (2018). Identification of genes involved in bacteriostatic antibiotic-induced persister formation. Frontiers in Microbiology, 9, 413.

Defrain, V., Fauvart, M., & Michiels, J. (2018). Fighting bacterial persistence: Current and emerging anti-persister strategies and therapeutics. Drug Resistance Updates, 38, 12-26.

DeLeon, S., Clinton, A., Fowler, H., Everett, J., Horswill, A. R., & Rumbaugh, K. P. (2014). Synergistic Interactions of *Pseudomonas aeruginosa* and *Staphylococcus aureus* in an in vitro wound model. Infection and Immunity, 82, 4718-4728.

Donegan, K., Matyac, C., Seidler, R., & Porteous, A. (1991). Evaluation of methods for sampling, recovery, and enumeration of bacteria applied to the phylloplane. Applied and Environmental Microbiology, 57, 51-56.

Dorr, T., Vulić, M., & Lewis, K. (2010). Ciprofloxacin causes persister formation by inducing the TisB toxin in *Escherichia coli*. PLOS Biology, 8, e1000317.

Grassi, L., Di Luca, M., Maisetta, G., Rinaldi, A. C., Esin, S., Trampuz, A., & Batoni, G. (2017). Generation of persister cells of *Pseudomonas aeruginosa* and *Staphylococcus aureus* by chemical treatment and evaluation of their susceptibility to membrane-targeting agents. Frontier in Microbiology, 8, 1917.

Harrison, J. J., Wade, W. D., Akierman, S., Vacchi-Suzzi, C., Stremick, C. A., Turner, R. J., & Ceri, H. (2009). The chromosomal toxin gene yafQ is a determinant of multi-drug tolerance for *Escherichia coli* growing in a biofilm. Antimicrobial Agents and Chemotherapy, 53, 2253-2258.

Hobby, G. L., Meyer, K., & Chaffee, E. (1942). Observations on the mechanism of action of penicillin. Proceedings of the Society for Experimental Biology and Medicine, 50, 281-285.

Hu, Y., Kwan, B. W., Osbourne, D. O., Benedik, M. J., & Wood, T. K. (2015). Toxin YafQ increases persister cell formation by reducing indole signalling. Environmental Microbiology, 17, 1275-1285.

Kim, J.-S., Chowdhury, N., Yamasaki, R., & Wood, T. K. (2018). Viable but non-culturable and persistence describe the same bacterial stress state. Environmental Microbiology, 20, 2038-2048.

Kim, J.-S., Yamasaki, R., Song, S., Zhang, W., & Wood, T. K. (2018). Single cell observations show persister cells wake based on ribosome content. Environmental Microbiology, 20, 2085-2098.

Kim, W., Zhu, W., Hendricks, G. L., VanTvne, D., Steele, A. D., Keohane, C. E., . . . Mylonakis, E. (2018). A new class of synthetic retinoid antibiotics effective against bacterial persisters. Nature, 556, 103-107.

Kim, Y., & Wood, T. K. (2010). Toxins Hha and CspD and small RNA regulator Hfq are involved in persister cell formation through MqsR in *Escherichia coli*. Biochemical Biophysical Research Communications, 391, 209-213.

Kwan, B. W., Chowdhury, N., & Wood, T. K. (2015). Combatting bacterial infections by killing persister cells with mitomycin C. Environmental Microbiology, 17, 4406-4414.

Kwan, B. W., Osbourne, D. O., Hu, Y., Benedik, M. J., & Wood, T. K. (2015). Phosphodiesterase DosP increases persistence by reducing cAMP which reduces the signal indole. Biotechnology and Bioengineering, 112, 588-600.

Kwan, B. W., Valenta, J. A., Benedik, M. J., & Wood, T. K. (2013). Arrested protein synthesis increases persister-like cell formation. Antimicrobial Agents and Chemotherapy, 57, 1468-1473.

Lee, J.-H., Kim, Y.-G., Gwon, G., Wood, T. K., & Lee, J. (2016). Halogenated indoles eradicate bacterial persister cells and biofilms. AMB Express, 6, 123.

Liberati, N. T., Urbach, J. M., Miyata, S., Lee, D. G., Drenkard, E., Wu, G., . . . Ausubel, F. M. (2006). An ordered, nonredundant library of *Pseudomonas aeruginosa* strain PA14 transposon insertion mutants. Proceeding of the National Academy of Sciences of United States of America, 103, 2833-2838.

Luidalepp, H., Jóers, A., Kaldalu, N., & Tenson, T. (2011). Age of inoculum strongly influences persister frequency and can mask effects of mutations implicated in altered persistence. Journal of Bacteriology, 193, 3598-3605.

Narayanaswamy, V. P., Keagy, L. L., Duris, K., Wiesmann, W., Loughran, A. J., Townsend, S. M., & Baker, S. (2018). Novel glycopolymer eradicates antibiotic- and CCCP-induced persister cells in *Pseudomonas aeruginosa*. Frontier in Microbiology, 9, 1724.

Pu, Y., Li, Y., Jin, X., Tian, T., Ma, Q., Zhao, Z., . . . Bai, F. (2019). ATPdependent dynamic protein aggregation regulates bacterial dormancy depth critical for antibiotic tolerance. Molecular Cell, 73, 143-156.

Song, S., & Wood, T. K. (2018). Post-segregational killing and phage inhibition are not mediated by cell death through toxin/antitoxin systems. Frontier in Microbiology, 9, 814.

Sulaiman, J. E., Hao, C., & Lam, H. (2018). Specific enrichment and proteomics analysis of *Escherichia Escherichia coli coli* persisters from rifampin pretreatment. Journal of Proteome Research, 17, 3984-3996.

Sun, Y., Dowd, S. E., Smith, E., Rhoads, D. D., & Wolcott, R. D. (2008). In vitro multispecies Lubbock chronic wound biofilm model. Wound Repair and Regeneration, 16, 805-813.

Tkhilaishvili, T., Lombardi, L., Klatt, A.-B., Trampuz, A., & Di Luca, M. (2018). Bacteriophage Sb-1 enhances antibiotic activity against biofilm, degrades exopolysaccharide matrix and targets persisters of *Staphylococcus aureus*. International Journal of Antimicrobial Agents, 52, 842-853.

Vanden Bergh, B., Fauvart, M., & Michiels, J. (2017). Formation, physiology, ecology, evolution and clinical importance of bacterial persisters. FEMS Microbiology Reviews, 41, 219-251.

Wang, X., Kim, Y., Hong, S. H., Ma, Q., Brown. B. L., Pu, M., . . . Wood, T. K. (2011). Antitoxin MqsA helps mediate the bacterial general stress response. Nature Chemical Biology, 7, 359-366.

Wang, X., & Wood, T. K. (2011). Toxin-antitoxin systems influence biofilm and persister cell formation and the general stress response. Applied and Environmental Microbiology, 77, 5577-5583.

Wood, T. K. (2016). Combatting bacterial persister cells. Biotechnology and Bioengineering, 113, 476-483.

Wood, T. K., Song, S., & Yamasaki, R. (2019). Ribosome dependence of persister cell formation and resuscitation. Journal of Microbiology, 57, 213-219.

Yang, T., Moreira, W., Nyantakyi, S. A., Chen, H., Aziz, db, Go, M.-L., & Dick, T. (2017). Amphiphilic indole derivatives as antimycobacterial agents: Structure-activity relationships and membrane targeting properties. Journal of Medicinal Chemistry, 60, 2745-2763.

Yuan, M., Chua, S. L., Liu, Y., Drautz-Moses, D. I., Yam, J. K. H., Aung, T. T., . . . Nielsen, T. E. (2018). Repurposing the anticancer drug cisplatin with the aim of developing novel *Pseudomonas aeruginosa* infection control agents. Beilstein Journal of Organic Chemistry, 14, 3059-3069.

Example 2—Persister Cells Resuscitate Via Ribosome Modification by 23S rRNA Pseudouridine Synthase RluD Reference is made to Song S. and Wood T K, "Persister Cells Resuscitate via Ribosome Modification by 23S rRNA Pseudouridine Synthase RluD," bioRxiv, doi: https://doi.org/10.1101/678425, available on-line Jun. 21, 2019; now published in Environmental Microbiology doi: 10.1111/1462-2920.14828, Volume 22, Issue 3, Pages 850-857, March 2020, first published 13 Oct. 2019.

Abstract

Upon a wide range of stress conditions (e.g., nutrient, antibiotic, oxidative), a subpopulation of bacterial cells known as persisters survive by halting metabolism. These cells resuscitate rapidly to reconstitute infections once the stress is removed and nutrients are provided. However, how these dormant cells resuscitate is not understood well but involves reactivating ribosomes. By screening 10.000 compounds directly for stimulating *Escherichia coli* persister cell resuscitation, we identified that 2-{[2-(4-bromophenyl)-2-oxoethyl]thio}-3-ethyl-5,6,7,8-tetrahydro[1]benzothieno [2,3-d]pyrimidin-4(3H)-one (BPOET) stimulates resuscitation. Critically, by screening 4.267 L. *coli* proteins, we determined that BPOET activates hibernating ribosomes via 23S rRNA pseudouridine synthase RluD, which increases ribosome activity. Corroborating the increased waking with RluD, production of RluD increased the number of active ribosomes in persister cells. Also, inactivating the small RNA RybB which represses rhuD led to faster persister resuscitation. Hence, persister cells resuscitate via activation of RluD.

Introduction

Upon myriad stresses such as antibiotic stress, a subpopulation of bacterial cells becomes dormant and multi-stress tolerant (1, 2), these cells are known as persisters. The persister phenotype is not due to genetic change, since upon re-growth, persisters cells behave the same as the original culture. Persistence is relevant in the environment since almost all cells face starvation (3) and relevant in medicine since recurring infections may be the result of regrowth of persister cells (4). The persister sub-population should be distinguished from slow-growing cells such as those in the stationary-phase or those generated by nutrient shifts (5); these slow-growing cells may be distinguished from persisters since the whole population of slow-growing cells are tolerant to antimicrobials whereas the non-growing persister population is a small sub-population (less than 1%) (6). This distinction is critical since tolerant cells utilize alternate sigma factors like RpoS in *Escherichia coli* to redirect gene expression as an active response against stress (7), whereas persisters cease responding and become dormant (5, 8.

To treat persister cell infections, it is important to understand how they form and how they resuscitate. The prevailing view for their formation (6) is that to reduce metabolism, cells activate toxins of toxin/antitoxin (TA) systems (2). The best genetic evidence for this is that deletion of toxins MqsR (10, 11), TisB (12), and YafQ (13) decreases persistence. Moreover, production of non-TAs toxins also increases persistence (14). However, since nutrient deprivation also results in persistence (15), the sub-population of cells may become dormant simply by running out of food. In addition, we have proposed a model whereby the alarmone ppGpp (synthesized as a result of myriad stress conditions), directly creates persister cells via ribosome dimerization, without the need of TA systems (16). Regardless of the mechanism, persistence appears to be an elegantly-regulated response to an unfavorable environment (17).

In regard to resuscitating persister cells, little has been determined about the mechanism. It has been suggested that persister cells resuscitate by inactivating toxins such as TacT acetyltransferase via peptidyl-tRNA hydrolase Pth (18), but this has not been demonstrated. It is established that persister cells revive in response primarily to environmental signals, such as fresh nutrients (rather than stochastically) (19). In addition, persisters revive in an heterogeneous manner, by activating ribosomes; cells increase their ribosome content until a threshold is reached, then they begin to elongate or divide (19). For resuscitation, the persisters sense nutrients by chemotaxis and phosphotransferase membrane proteins, reduce cAMP levels to rescue stalled ribosomes, unhybridize 100S ribosomes via HflX, and undergo chemotaxis toward fresh nutrients (20).

In the present study, to discern additional insights into how ribosomes are active as persister cells resuscitate, we converted the complete *E. coli* population into persister cells so that we could screen for the first time compounds that enhance persister resuscitation. From a 10,000 compound library, we identified that 2-{[2-(4-bromophenyl)-2-oxoethyl]thio}-3-ethyl-5,6,7,8-tetrahydro[1]benzothieno[2,3-d]pyrimidin-4(3H)-one (BPOET) stimulates persister cell waking. Critically, we determined that the mechanism by which BPOET resuscitates persisters is via activation of the 23S rRNA pseudouridine synthase RluD, which is important for ribosome activity. Hence, BPOET stimulates persister resuscitation by activating ribosomes via RluD.

Materials and Methods

Bacteria and growth conditions. *E. coli* K-12 and its isogenic mutants (Table 3) were grown routinely in lysogeny broth (21) (22) at 37° C. BPOET was obtained from ChemBridge (San Diego, Calif.).

TABLE 3

E. coli bacterial strains and plasmids used in this study. KmR and CmR indicate kanamycin and chloramphenicol resistance, respectively.

| Strains and Plasmids | Features | Source |
|---|---|---|
| BW25113 | Wild type | (39) |
| BW25113 ΔrluD | ΔrhD Km$^R$ | (39) |
| MG1655 | Wild type | (40) |
| MG1655 ΔrybB | ΔrybB Km$^R$ | (41) |
| MG1655 □ASV Plasmids | rrnbP1::GFP[ASV] | (26) |
| pC7A24N | Cm$^R$; lacI$^q$ | (25) |
| pCA24N_rluD | Cm$^R$; lacI$^q$, P$_{T5-lac}$::rluD$^+$ | (25) |

Persister cells. *E. coli* persister cells were generated (19, 23) by treating exponentially-growing cells (turbidity of 0.8 at 600 nm) with rifampicin (100 μg/mL) for 30 min to stop transcription, centrifuging, and adding LB with ampicillin (100 μg/mL) for 3 h to lyse any non-persister cells. Cells pellets were washed twice with 0.85% NaCl then re-suspended in 0.85% NaCl.

ChemBridge screen to identify resuscitation compounds. To identify compounds that resuscitate *E. coli* persister cells, the DIVERset Library from ChemBridge (San Diego, Calif.) containing 10,000 druglike compounds with high pharmacophore diversity was evaluated by adding 4 μL of each compound (final concentration 100 μM, dissolved in DMSO) to 186 μL of LB in 96 well plates and then adding 10 μL of persister cells. The negative control was 2 vol % DMSO. Resuscitation was calculated as the change in turbidity at 600 nm. The compounds that were identified initially were re-tested in M9 minimal medium with 5×alanine (24).

Pooled ASKA screen to identify resuscitation proteins. To identify proteins responsible for resuscitation, all 4,267 ASKA clones (GFP-) (25) were combined, grown to a turbidity of 2 at 600 nm in LB medium, and their plasmids isolated using a plasmid DNA Mini Kit I (OMEGA Bio-Tek, Inc., Norcross, Ga. USA). The pooled ASKA plasmids (1 μL containing 30 ng DNA) were electroporated into 50 μL of *E. coli* BW25113 competent cells, 1 mL LB medium was added, and the cells were grown to a turbidity of 0.5 at 600 nm. Chloramphenicol was added (30 μg/mL) to the culture to maintain the plasmids, and the cells were incubated at 250 rpm to a turbidity of 0.8. Rifampicin followed by ampicillin was added to make persister cells, then the persister cells were washed twice with 1×PBS buffer, contacted with 100 μM BPOET for 2 h in M9 medium that lacked a carbons source, and plated on LB (Cm) agar plates. Faster colony appearance indicated faster persister resuscitation. Plasmids were isolated from the colonies and sequenced using primer pCA24N_F: GCCCTTTCGTCTTCACCTCG.

Single-cell persister resuscitation. As described previously (19), 5 μL of cell populations consisting of 100% persister cells were added to 1.5% agarose gel pads containing either M9 medium with glucose (0.4 w-t %) or alanine (5×) as a carbon source (24), and resuscitation was monitored at 37° C. via a light microscope (Zeiss Axio Scope.A1, bl_ph channel at 1000 ms exposure).

Active 70S ribosome assay. The GFP signal of resuscitating persisters of *E. coli* K-12 MG1655-ASVGFP (26) with RluD was monitored using a fluorescence microscope (Zeiss Axioscope.A1, bl_ph channel at 1,000 ms exposure and GFP channel at 10,000 ms exposure). F. *coli* K-12 MG1655-ASVGFP produces an unstable variant of GFP (half-life less than 1 h) under the control of the 16S rRNA ribosomal promoter rrnbP1 (2).

Results & Discussion

BPOET resuscitates *E. coli* persister cells. To identify compounds that resuscitate *E. coli* persister cells, we first increased by $10^5$-fold the persister cell population by pre-treating with rifampicin to cease metabolism by stopping transcription followed by ampicillin treatment to kill any remaining non-persister cells (23). In this way, nearly 100% of bacterial cell population was converted into persister cells. Hence, we were able to both screen for compounds that more rapidly resuscitate persister cells as well as confirm our hypotheses via single-cell microscopy. The persister cells generated in this way have been (i) confirmed eight ways (19), (ii) used to determine that persister cells wake via ribosome activation (19) and chemotaxis (20), (iii) used to show that the cells capable of resuscitation in a viable but not culturable population are equivalent to persister cells (15), (iv) used to identify compounds that kill persister cells (27), and (v) used to show that the alarmone ppGpp directly creates persister cells by stimulating ribosome dimerization (16). In addition, our method to generate a high population of persister cells has been utilized by at least six independent groups (28-33).

Using 96-well plates, the persister cells (10 μL) were added to 190 μL of LB containing one each of the 10,000 compounds of the DiverSet library dissolved in dimethyl sulfoxide (100 μM final concentration), and growth was monitored via the change in turbidity for up to 48 h. Starting at a turbidity of 0.05, a 140-fold increase in growth was possible (maximum final turbidity of 0.69). Table 4 shows the 27 compounds that were identified that stimulated persister cell resuscitation relative to the negative control of dimethyl sulfoxide.

TABLE 4

Compounds that resuscitate persister cells and their structures that were identified in the initial screen.

| Name | Structure |
|---|---|
| 2-{[2-(4-bromophenyl)-2-oxoethyl]thio}-3-ethyl-5,6,7,8-tetrahydro[1]benzothieno[2,3-d]pyrimidin-4(3H)-one (BPOET) | |
| methyl 5-[(dimethylamino)carbonyl]-4-methyl-2-({[(1-methyl-1H-pyrazol-3-yl)amino]carbonothioyl}amino)-3-thiophenecarboxylate | 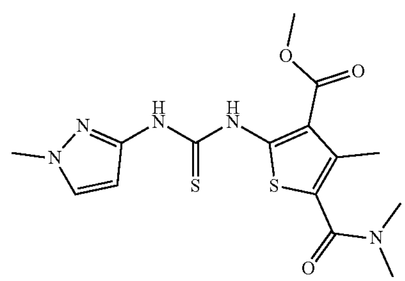 |
| N-[2-(3,4-dimethoxyphenyl)ethyl]-N'-[1-(pentafluorobenzyl)-1H-pyrazol-3-yl]thiourea | 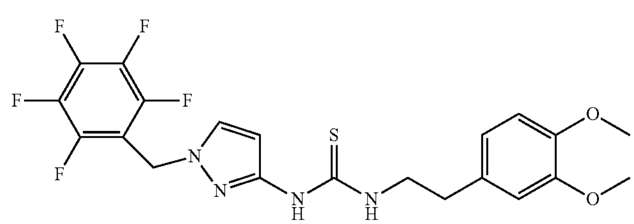 [SMILES: COc1ccc(CCNC(=S)Nc2ccn(Cc3c(F)c(F)c(F)c(F)c3F)n2)cc1OC] |
| 4-chloro-N-(6,7-dimethoxy-4-oxo-1,4-dihydro-2-quinazolinyl)benzamide | 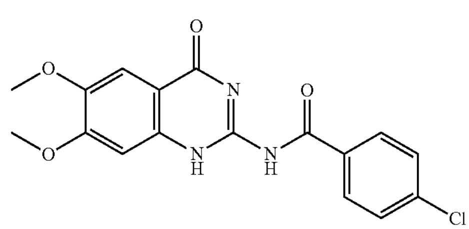 [SMILES: COc1cc2[nH]c(NC(=O)c3ccc(Cl)cc3)nc(=O)c2cc1OC] |
| (4-methoxyphenyl)(phenyl)methanone | 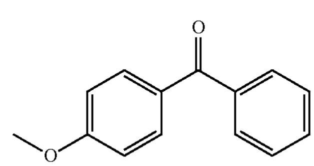 [SMILES: COc1ccc(C(=O)c2ccccc2)cc1] |

TABLE 4-continued

Compounds that resuscitate persister cells and their structures that were identified in the initial screen.

| Name | Structure |
| --- | --- |
| N-(3-acetylphenyl)-4,5-dimethyl-2-furamide | 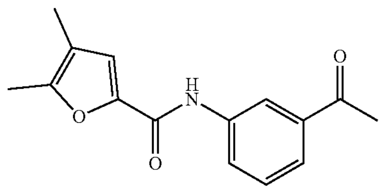 [SMILES: CC(=O)c1cccc(NC(=O)c2cc(C)c(C)o2)c1] |
| 6-(4-iodophenyl)-2-methylimidazo[2,1-b][1,3]thiazole | 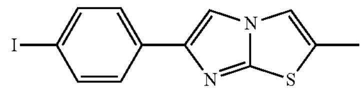 |
| N-{[(4-bromophenyl)amino]carbonothioyl}-2,2-dimethylpropanamide | 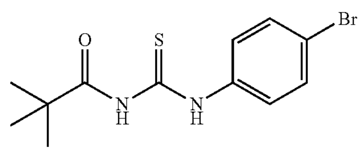 [SMILES: CC(C)(C)C(=O)NC(=S)Nc1ccc(Br)cc1] |
| 1-(2,4-dichlorobenzoyl)-2,3-dihydro-1H-imidazo[1,2-a]benzimidazole | 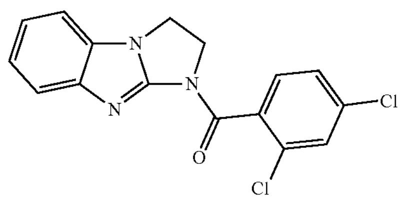 [SMILES: O=C(c1ccc(Cl)cc1Cl)N1CCn2c1nc1ccccc12] |
| 3-(3-chlorophenyl)-5,5-dimethyl-4-methylene-1,3-oxazolidin-2-one | 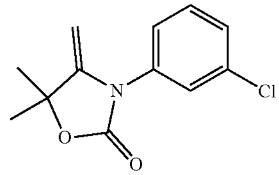 [SMILES: C=C1N(c2cccc(Cl)c2)C(=O)OC1(C)C] |
| 2-methyl-4-[4-(methylthio)phenyl]-5-oxo-N-phenyl-1,4,5,6,7,8-hexahydro-3-quinolinecarboxamide | 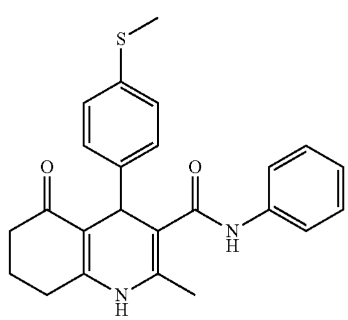 [SMILES: CSc1ccc(C2C(C(=O)Nc3ccccc3)=C(C)NC3=C2C(=O)CCC3)cc1] |
| 4-(isopropoxycarbonyl)benzyl 2-pyrazinecarboxylate | 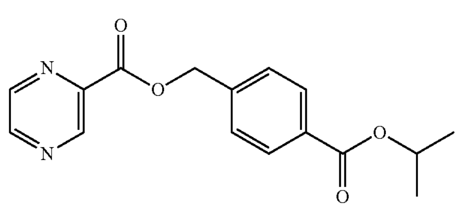 [SMILES: CC(C)OC(=O)c1ccc(COC(=O)c2cnccn2)cc1] |

TABLE 4-continued

Compounds that resuscitate persister cells and their structures that were identified in the initial screen.

| Name | Structure |
|---|---|
| N-[4-(2-oxo-1-pyrrolidinyl)phenyl]-1H-1,2,4-triazole-3-carboxamide | 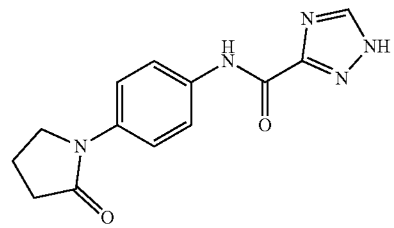 [SMILES: O=C(Nc1ccc(N2CCCC2=O)cc1)c1nc[nH]n1] |
| 4-chloro-N-(4-oxo-1,4-dihydro-2-quinazolinyl)benzamide | 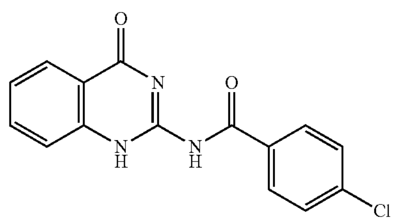 [SMILES: O=C(Nc1nc(=O)c2ccccc2[nH]1)c1ccc(Cl)cc1] |
| 3-hydroxy-5-(4-propoxyphenyl)-1-(3-pyridinylmethyl)-4-(2-thienylcarbonyl)-1,5-dihydro-2H-pyrrol-2-one | 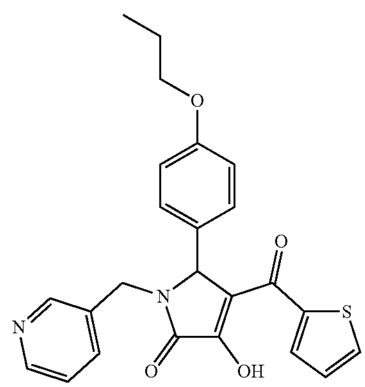 [SMILES: CCCOc1ccc(C2C(C(=O)c3cccs3)=C(O)C(=O)N2Cc2cccnc2)cc1] |
| 4-(3,4-dimethoxyphenyl)-2-hydrazino-6-phenylpyrimidine | 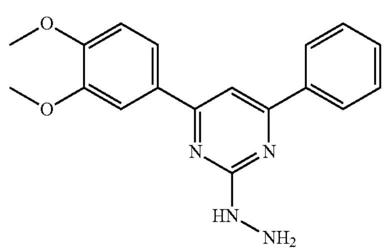 [SMILES: COc1ccc(-c2cc(-c3ccccc3)nc(NN)n2)cc1OC] |
| N'-[1-(3,4-dimethoxyphenyl)ethylidene]-3-phenyl-1H-pyrazole-5-carbohydrazide | 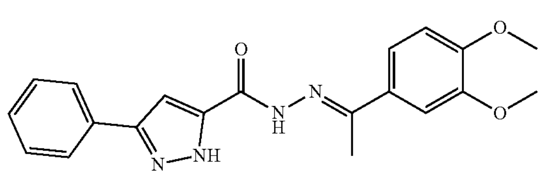 [SMILES: COc1ccc(/C(C)=N/NC(=O)c2cc(-c3ccccc3)n[nH]2)cc1OC] |
| 3-[4-(4-chlorophenyl)-1-piperazinyl]-1-(4-iodophenyl)-2,5-pyrrolidinedione | 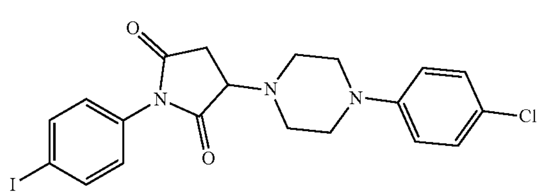 [SMILES: O=C1CC(N2CCN(c3ccc(Cl)cc3)CC2)C(=O)N1c1ccc(I)cc1] |

TABLE 4-continued

Compounds that resuscitate persister cells and their structures that were identified in the initial screen.

| Name | Structure |
|---|---|
| N-(3-oxo-1,3-dihydro-2-benzofuran-5-yl)-1H-1,2,4-triazole-3-carboxamide | 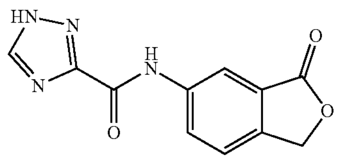 [SMILES: O=C(Nc1ccc2c(c1)C(=O)OC2)c1nc[nH]n1] |
| 3-[(5-methyl-2-furoyl)amino]benzoic acid | 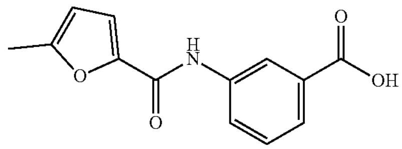 [SMILES: Cc1ccc(C(=O)Nc2cccc(C(=O)O)c2)o1] |
| N-(4-{[(2,4-dimethoxyphenyl)amino]sulfonyl}phenyl)-3-[(4-methylphenyl)thio]propanamide | 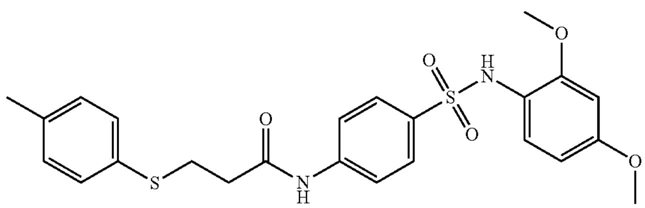 |
| N~2~-(3-fluorophenyl)-N~2~-(methylsulfonyl)-N~1~-[2-(1-pyrrolidinylcarbonyl)phenyl]glycinamide | 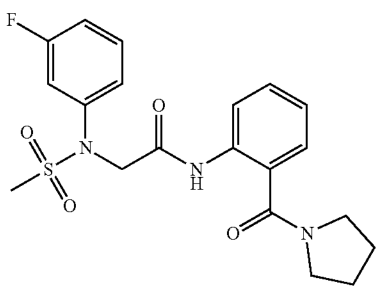 [SMILES: CS(=O)(=O)N(CC(=O)Nc1ccccc1C(=O)N1CCCC1)c1cccc(F)c1] |
| N-(5-chloro-2-methoxyphenyl)-N'-(1-ethyl-3,5-dimethyl-1H-pyrazol-4-yl)thiourea | 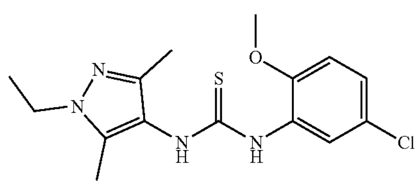 [SMILES: CCn1nc(C)c(NC(=S)Nc2cc(Cl)ccc2OC)c1C] |
| 1-[(4-methylphenyl)sulfonyl]-N-1,3-thiazol-2-ylprolinamide | 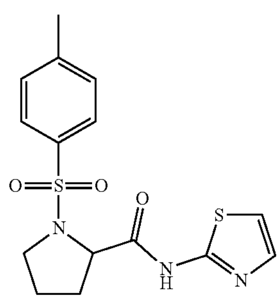 [SMILES: Cc1ccc(S(=O)(=O)N2CCCC2C(=O)Nc2nccs2)cc1] |
| 2,5-dichloro-N-(2-furylmethyl)benzamide | 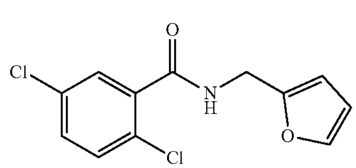 [SMILES: O=C(NCc1ccco1)c1cc(Cl)ccc1Cl] |

TABLE 4-continued

Compounds that resuscitate persister cells and their structures that were identified in the initial screen.

| Name | Structure |
| --- | --- |
| 3-{[(2-methoxyphenyl)amino]methyl}-5-[4-(methylthio)benzylidene]-1,3-thiazolidine-2,4-dione | 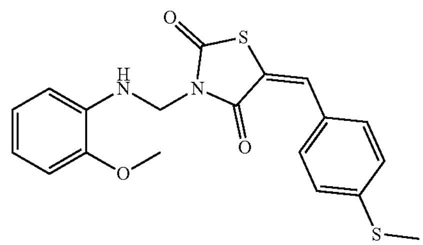 [SMILES: COc1ccccc1NCN1C(=O)S/C(=C/c2ccc(SC)cc2)C1=O] |
| 5-(4-propoxybenzyl)-1H-tetrazole | 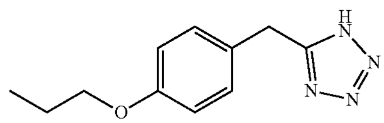 [SMILES: CCCOc1ccc(Cc2nnn[nH]2)cc1] |

Figure 12:
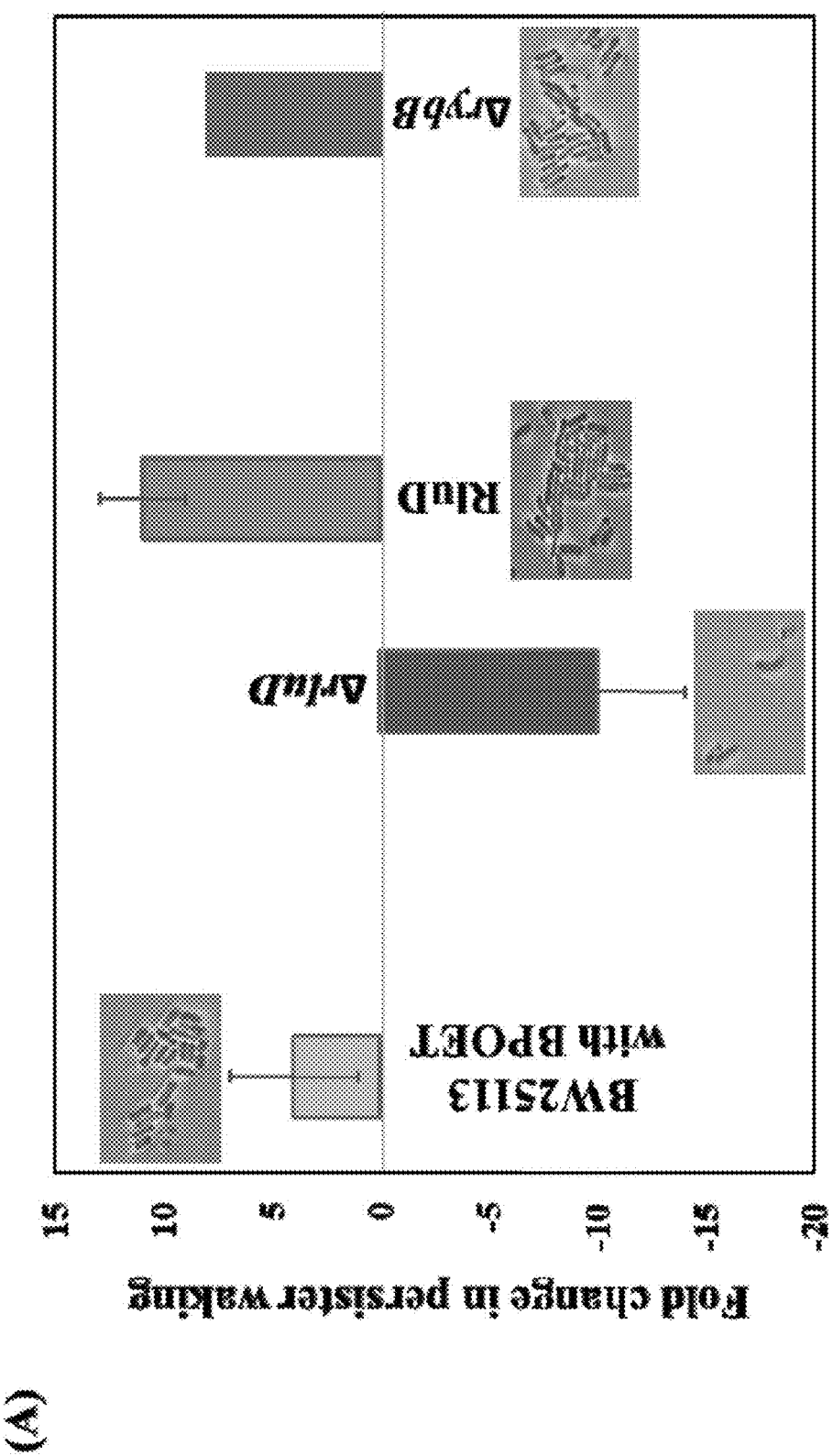
FIG. 12. RluD increases persister resuscitation by increasing ribosomes for resuscitation. (A) Single-cell persister resuscitation as determined using light microscopy (Zeiss Axio Scope.A1). The total and waking number of persister cells are shown in Table 5. Microscope images for waking cells are shown in FIG. 13. The fold-change in resuscitation is relative to BW25113 with DMSO for BW25113 with BPOET, relative to BW25113 for the ΔrluD mutant, relative to BW25113/pCA24N for the strain producing RluD from pCA24N plasmid in BW25113, and relative to MG1655 for ΔrybB. M9 glucose (0.4%) agarose gel pads were used for all the strains except BW25113 with BPOET where M9 alanine (5×) agarose gel pads including 100 μM of BPOET or DMSO were used. The results are the combined observations from two independent experiments after 6 h for the BW25113 with BPOET, after 4 h for BW25113 and its deletion mutants, and after 6 h for cells harboring pCA24N and its derivatives as well as for MG1655 and MG1655 ΔrybB. Error bars indicate standard deviations. (B) Active 70S ribosomes in single persister cells for MG1655-ASV/pCA24N-rluD ("RluD") vs. MG1655-ASV/pCA24N ("Empty"). Cells are shown on agarose gel pads at time 0 for resuscitation; i.e., after the formation of persister cells. Representative results from three independent cultures are shown.
Figure 12:
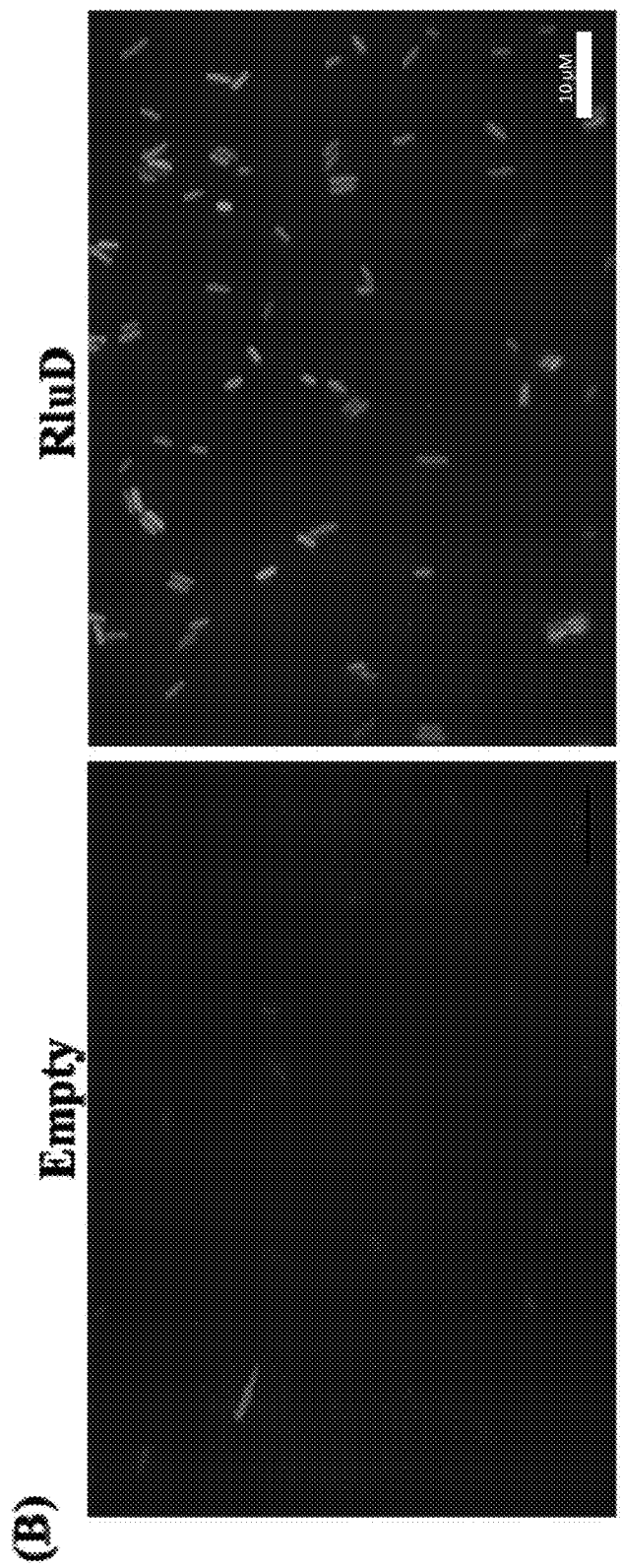

Upon confirming the results of these initial hits in minimal alanine medium, we found BPOET (100 μM) was most effective and increased persister cell waking by 44-fold in 96-well plates based on the increases in turbidity as well as found that BPOET increases the waking of single persister cells by 4-fold (FIG. 12, Table 5). Hence, we focused on this compound.

TABLE 5

Single persister cell resuscitation.

| | Total cells | Waking cells | % waking | Fold-change |
| --- | --- | --- | --- | --- |
| BW25113 on DMSO | 215 ± 46 | 11 ± 4 | 5 ± 7 | 1 |
| BW25113 on BPOET | 213 ± 49 | 38 ± 18 | 20 ± 13 | 4 ± 3 |
| BW25113 | 150 ± 46 | 24 ± 5 | 16 ± 1 | 1 |
| ΔrluD | 327 ± 16 | 5 ± 0 | 1.5 ± 0.1 | −10 ± 1 |
| pCA24N | 233 ± 155 | 5 ± 4 | 1.8 ± 0.3 | 1 |
| pCA24N-rluD | 210 ± 33 | 43 ± 6 | 20 ± 6 | 11 ± 4 |
| MG1655 | 310 ± 103 | 8.5 ± 5 | 2.6 ± 0.7 | 1 |
| ΔrybB | 208 ± 10 | 45 ± 0 | 22 ± 1 | 8 ± 2 |

Figure 13:
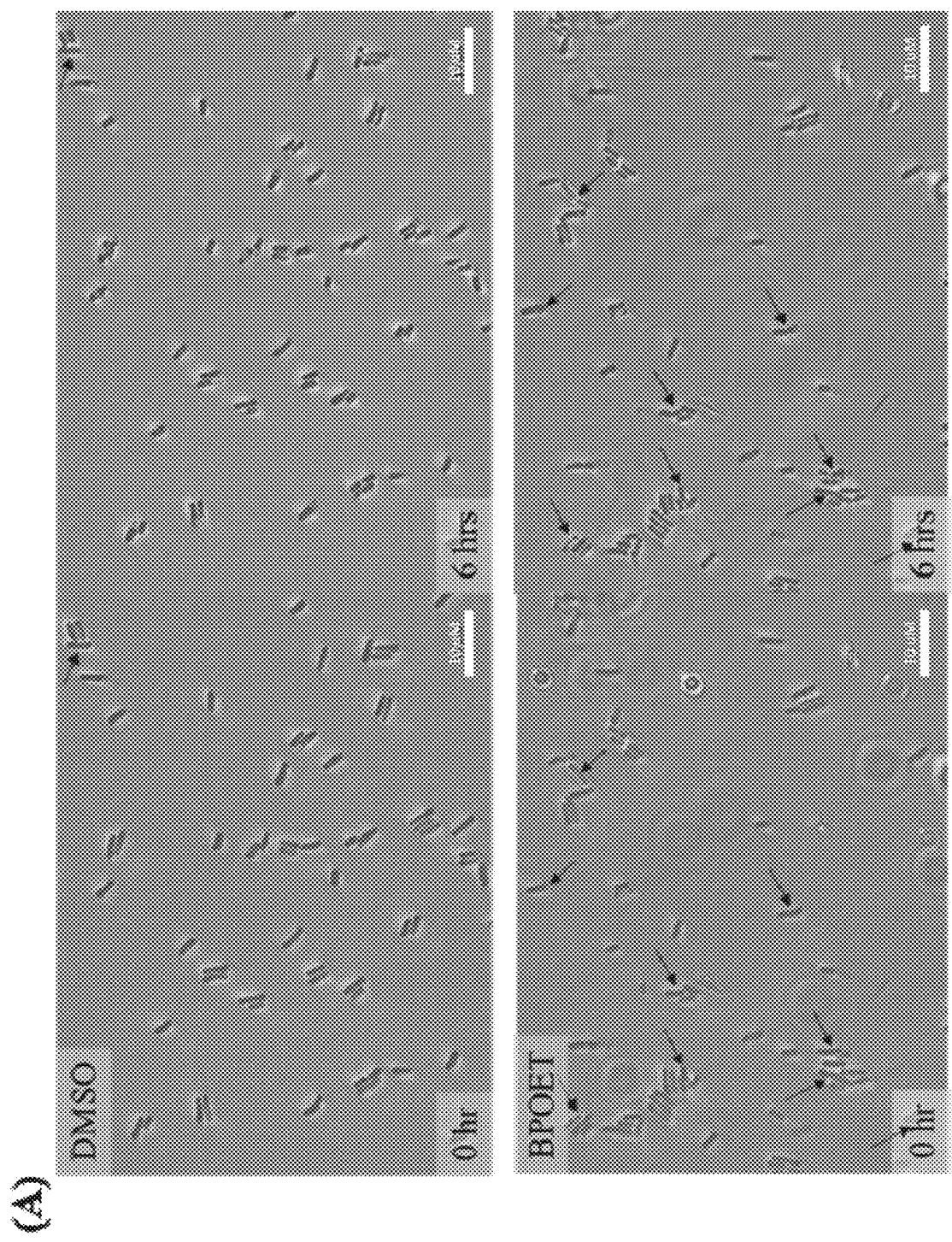
FIG. 13. Single persister cell waking. Persister cells of (A) BW25113 with DMSO (upper panel), and BPOET (lower panel) on M9 5×Ala agarose gel pads containing DMSO and BPOET (100 μM) after 6 h, (B) BW25113 (upper panel) and BW25113 ΔrluD (lower panel) after 4 hours on M9 0.4% glucose agarose gel pads, (C) BW25113/pCA24N ("Empty"), and BW25113/pCA24N-rluD ("RluD") after 6 h on M9 0.4% glucose agarose gel pads, and (D) MG1655, and MG1655 ΔrybB after 6 h on M9 0.4% glucose agarose gel pads. Arrows indicate cells that resuscitate. Scale bar indicates 10 μm. Representative results from two independent cultures are shown.
Figure 13:
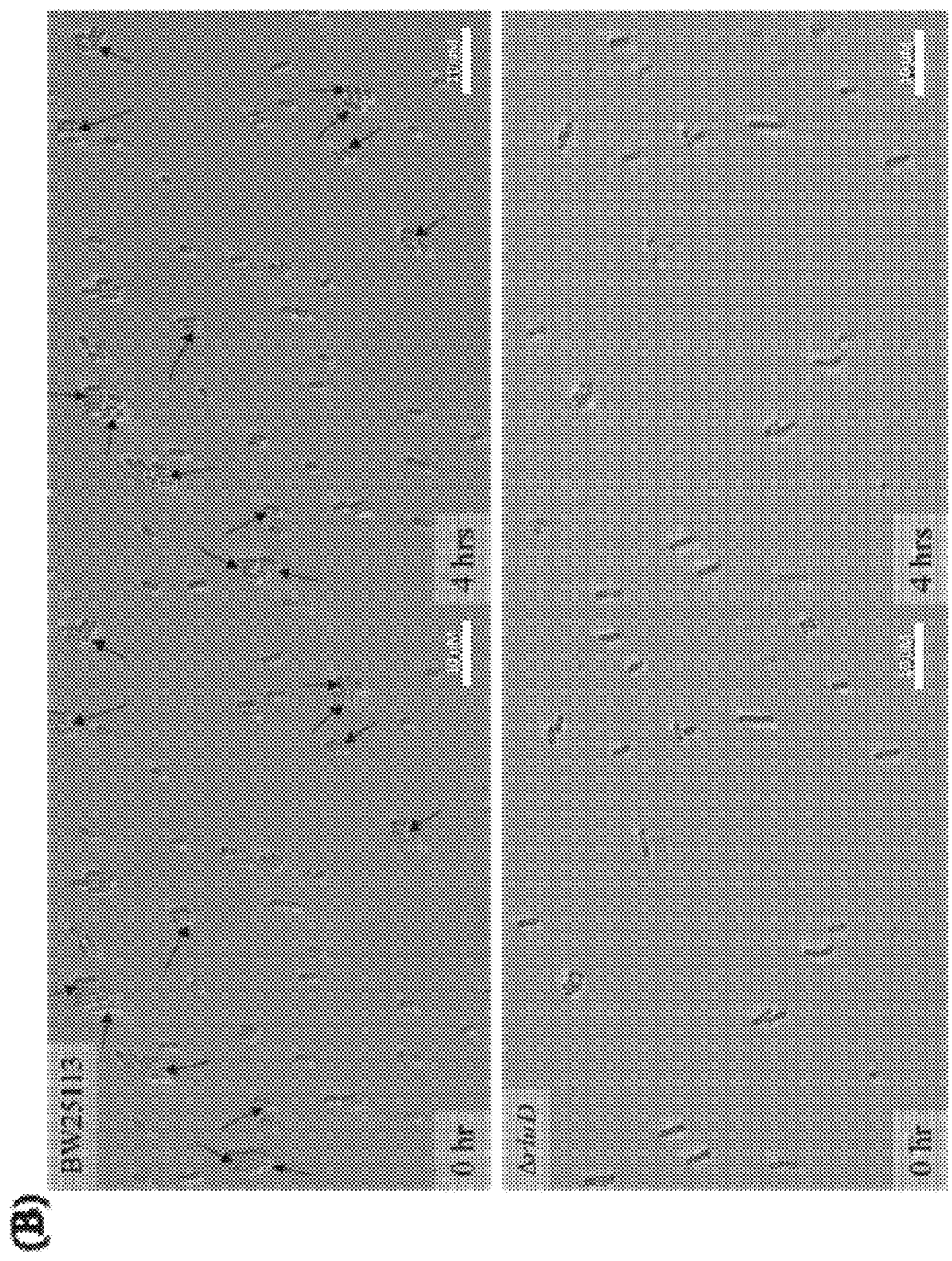
Figure 13:
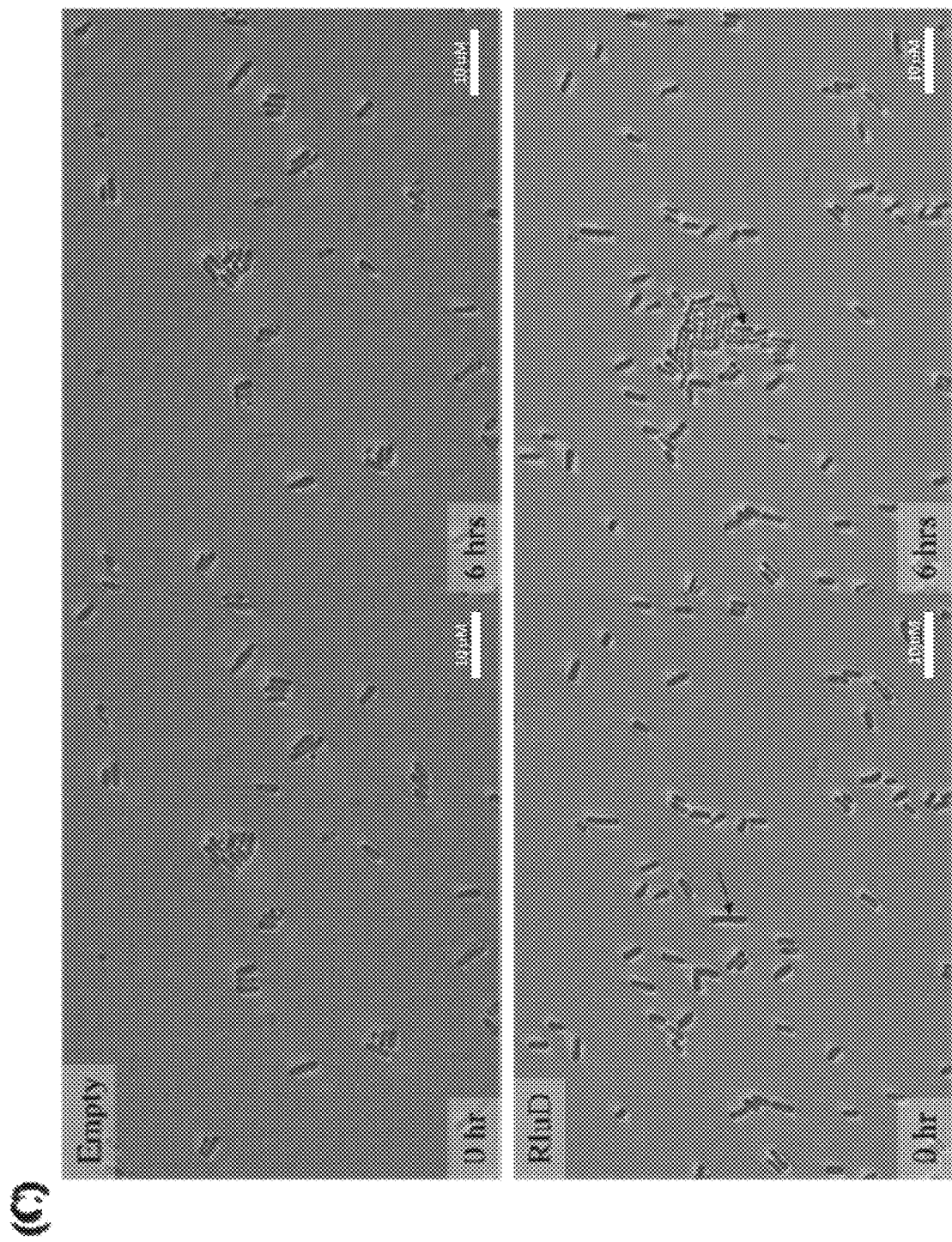
Figure 13:
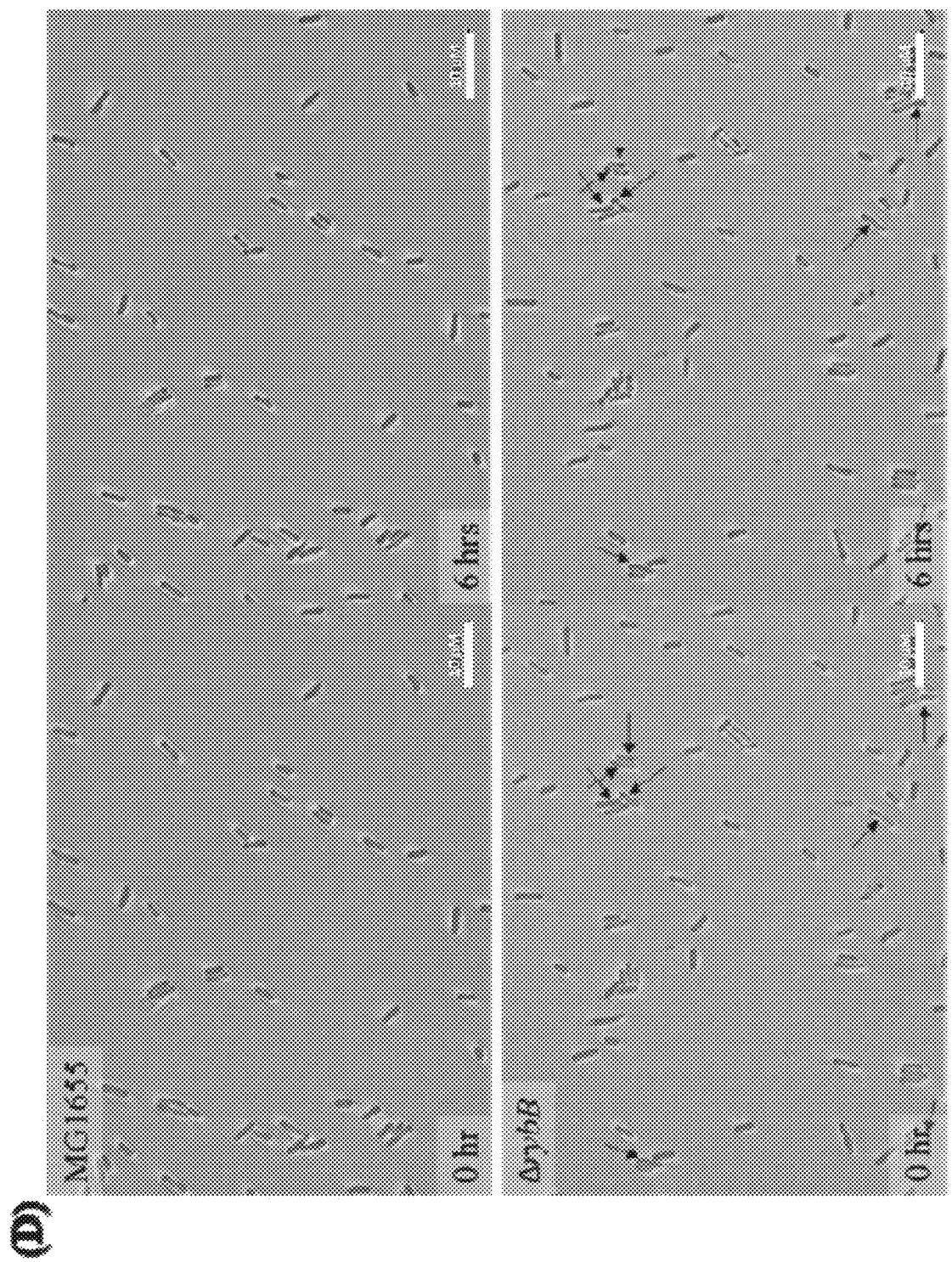

Single-cell persister resuscitation as determined using light microscopy (Zeiss Axio Scope.A1) using agarose gel pads.
Microscope images are shown in FIG. 13. The fold-change in resuscitation is relative to BW25113 with DMSO for BW25113 with BPOET, relative to BW25113 for the ΔrluD, relative to BW25113/pCA24N for the strain producing RluD from pCA24N in BW25113, and relative to MG1655 for ΔrybB. M9 glucose (0.4%) agarose gel pads were used for all the strains except BW25113 with BPOET where M9 alanine (5X) agarose gelpads including 100 μM of BPOET or DMSO were used.
The results are the combined observations from two independent experiments after 6 h for the BW25113 with BPOET and DMSO, after 4 h for BW25113 and its deletion mutants, and after 6 h for cells harboring pCA24N and its derivatives as well as for MG1655, and ΔrybB.
Standard deviations are shown, and each strain was visualized at 14 positions.

TABLE 6

Active 70S ribosomes in single persister cells for MG1655-ASV/pCA24N-rulD ("pCA24N-rluD") vs. MG1655-ASV/pCA24N ("pCA24N").

| | pCA24N-rluD | pCA24N |
| --- | --- | --- |
| Total cells | 140 ± 66 | 11.2 ± 4 |
| High intensity cells | 120 ± 64 | 25 ± 3 |
| Waking % | 85 ± 6 | 22 ± 2 |
| Fold-change | 3.8 ± 0.4 | 1 |

Single-cell persister resuscitation as determined using light microscopy (Zeiss Axio Scope.A1) using agarose gel pads with 0.4% glucose.
Microscope images are shown in FIG. 12B. The fold-change in resuscitation is relative to MG1655-ASV/pCA24N for M1655-ASV/pCA24N-rluD.

BPOET resuscitates *E. coli* persister cells by modifying ribosomes. To determine how BPOET resuscitates persister cells, we pooled the 4,267 ASKA clones in which each *E. coli* protein is produced from plasmid pCA24N, produced persister cells carrying these plasmids, contacted with 100 μM BPOET, plated the cells, and chose the largest colonies that formed on LB plates. Our rationale was that any pathway stimulated by BPOET would be even more active if the number of rate-limiting proteins in that pathway were increased, and cells that wake first would form colonies faster.

Using this approach, we identified five proteins whose production increased resuscitation: RluD, YjiK, SrlR, Smf, and YeeZ. These proteins are related to contacting with BPOET since addition of the diluent DMSO alone and sequencing larger colonies did not identify these five proteins but instead identified TmcA, a tRNA$^{Met}$ cytidine acctyltransferase, which is a general factor required for translation that likely led to larger colony sizes with the diluent. Of the proteins related to BPOET, only RluD (23S rRNA pseudouridine synthase) and SrlR (represses the gut operon for glucitol metabolism) have been characterized; we focused on RluD because it is related to ribosomes, and we have shown inactivating ribosomes causes persistence (23) and activating ribosomes resuscitates persister cells (16, 19, 20). RluD is involved in the synthesis and assembly of 70S ribosomes as well as their function based on its post-transcriptional modification of 23S rRNA to form three pseudouridine (5-ribosyl-uracil) nucleosides at positions 1911, 1915, and 1917 (34). In pseudouridine, uracil is attached via a carbon-carbon bond to the sugar base rather than through a carbon-nitrogen bond. The 23S rRNA pseudouridines increase the stability of the tertiary structure of 23S rRNA and are located in a stem loop structure that is involved in peptidyltransferase and interacts with mRNA, tRNA, 16S rRNA, and ribosome release factor. Hence, RluD is responsible for efficient ribosome function (34).

Figure 14:
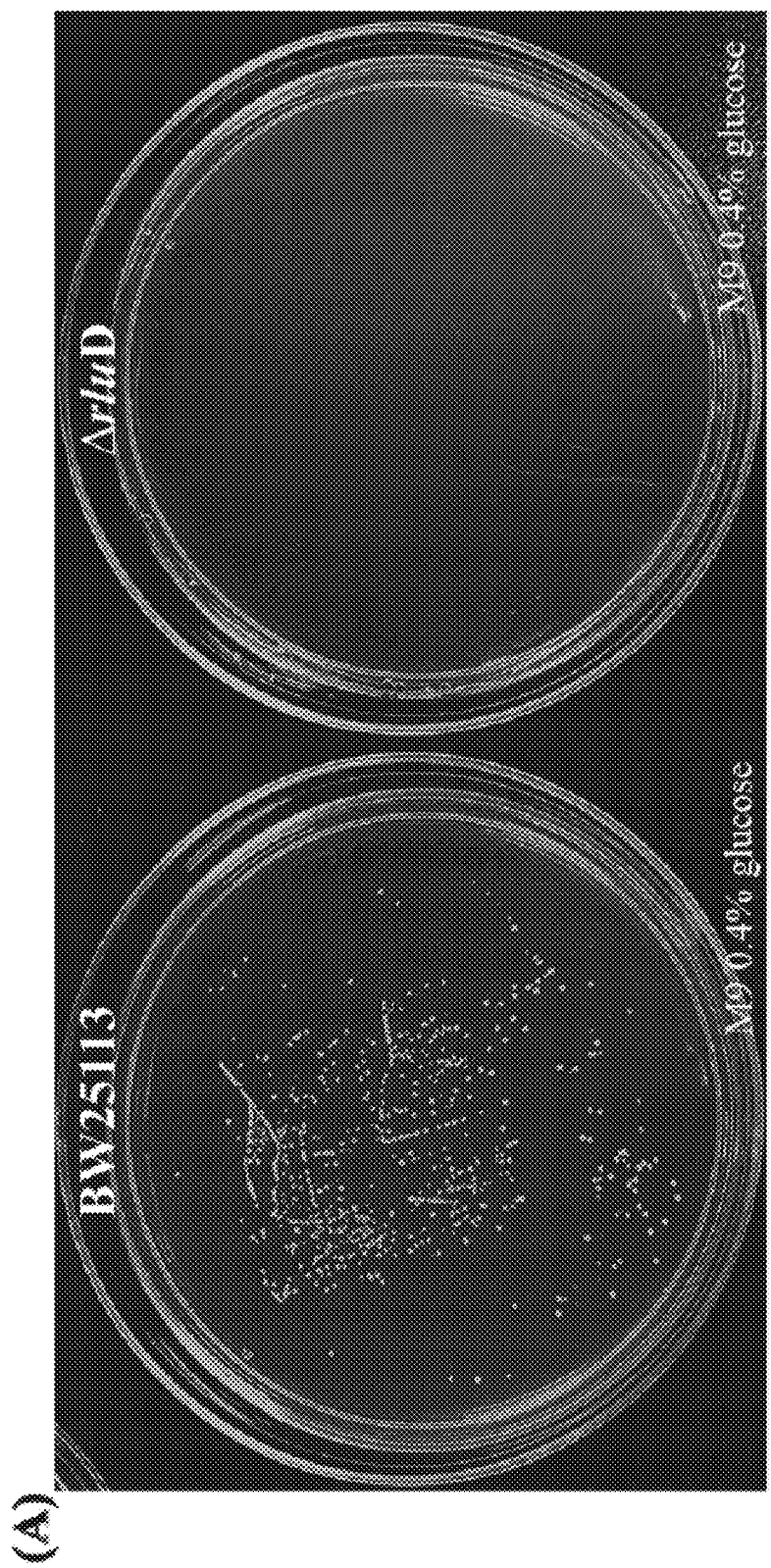
FIG. 14. Inactivating RluD eliminates persister cell waking on minimal glucose medium but does not affect the number of persister cells that are formed. (A) Resuscitation of wild type BW25113 and BW25113 ΔrluD persister at 37° C. on M9 0.4% glucose agar plates for three days. (B) Colonies formed in one day at 37° C. on LB agar plates indicating the number of persister cells for BW25113 and the isogenic ΔrluD mutant. One representative plate of two independent cultures is shown.
Figure 14:
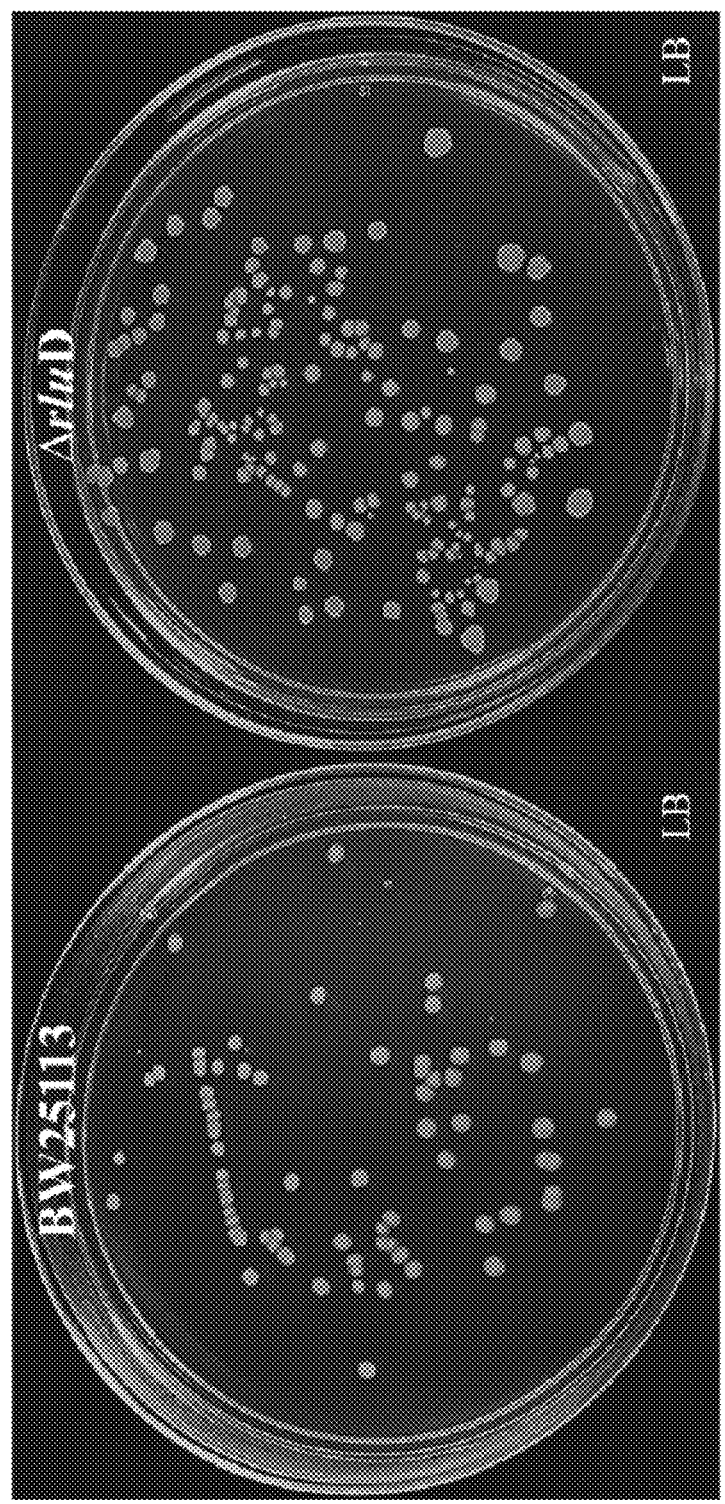

RluD enhances persister cell resuscitation. To explore further the role of RluD and persister resuscitation, we utilized single cell studies since persister cells are heterogeneous (19) and wake with different frequencies (which would be missed if we monitored planktonic populations). We found that deleting rulD reduces the frequency of single-cell persister resuscitation dramatically (11-fold) compared to the isogenic wild-type strain on minimal glucose agarose gel pads (FIG. 12A, Table 5, FIG. 13). In addition, no colonies were found on M9 glucose agar plates after inactivating RluD (FIG. 14), confirming that persister cells are severely challenged in resuscitation without RluD. Corroborating these two results with the rluD mutant, production of RluD increased the frequency of waking by 11-fold on glucose medium (FIG. 12A, Table 5, FIG. 13) and increased waking on rich medium (results not shown). In addition, the rluD deletion has no effect on persister cell formation (FIG. 14). Therefore, RluD stimulates persister cell resuscitation but does not affect persister formation.

RluD increases active ribosomes for resuscitation. Using a GFP reporter that indicates the number of 70S ribosomes in individual persister cells (19), we found that producing RluD before making persister cells makes 85±6% of the cells have high ribosome fractions compared to not producing RluD (FIG. 12B). The GFP reporter indicates transcription of rrsB (16S rRNA), gltT (tRNA-glu), rrlB (23S rRNA) and rrfB (5S rRNA); hence, it indicates production of the three major rRNA building blocks. Although this is not a direct observation of 70S ribosomes, this method is a suitable proxy for the number of ribosomes based on measurement of rRNA concentrations and has been used frequently (19, 35-37), and we have verified its use by isolating ribosomes and comparing GFP fluorescence (19). Hence, the increased persister cell resuscitation with RluD is directly due to the increase in active (70S) ribosomes of persister cells.

RybB antagonizes persister cell resuscitation. Since the small RNA RybB represses RluD (38), we investigated its impact on persister resuscitation. As expected, we found that deletion of rybB increases the frequency of persister cell waking by 8-fold (FIG. 12A, Table 5, FIG. 13).

In summary, the results presented here demonstrate that ribosomes may be activated for specific cell cycles such as recovery from dormancy. Specifically, by screening for compounds for the first time that enhance persister cell resuscitation, we have (i) determined that ribosomes are modified by RluD as cells resuscitate and resume ribosome activity, (ii) identified a novel compound, BPOET, that activates persister cells, and (iii) linked small RNAs to persistence. Hence, these results extend our understanding of how persister cells are activated which has a far-reaching impact in that all bacteria cope with nutrient stress and become dormant.

REFERENCES

1. Hobby G L, Meyer K, & Chaffee E Observations on the mechanism of action of penicillin. P Soc Exp Biol Med 50:281-285 (1942).
2. Bigger J W Treatment of staphylococcal infections with penicillin—By intermittent sterilisation. Lancet 2:497-500 (1944).
3. Song S & Wood T K Post-segregational Killing and Phage Inhibition Are Not Mediated by Cell Death Through Toxin/Antitoxin Systems. Front Microbiol 9:814 (2018).
4. Van den Bergh B, Fauvart M, & Michiels J Formation, physiology, ecology, evolution and clinical importance of bacterial persisters. FEMS Microbiol. Rev. 41:219-251 (2017).
5. Kim J-S & Wood T K Tolerant, Growing Cells from Nutrient Shifts Are Not Persister Cells. mBio 8:e00354-00317 (2017).
6. Ronneau S & Helaine S Clarifying the Link between Toxin-Antitoxin Modules and Bacterial Persistence. J. Mol. Biol. (2019).
7. Wang X, et al. Antitoxin MqsA helps mediate the bacterial general stress response. Nature Chem. Biol. 7:359-366 (2011).
8. Kim J-S & Wood T K Persistent Persister Misperceptions. Front. Microbiol. 7:2134 (2016).
9. Wang X & Wood T K Toxin-antitoxin systems influence biofilm and persister cell formation and the general stress response. Appl. Environ. Microbiol. 77:5577-5583 (2011).
10. Kim Y & Wood T K Toxins Hha and CspD and small RNA regulator Hfq are involved in persister cell formation through MqsR in *Escherichia coli*. Biochem. Biophys. Res. Commun. 391:209-213 (2010).
11. Luidalepp H, Jõers A, Kaldalu N, & Tenson T Age of Inoculum Strongly Influences Persister Frequency and Can Mask Effects of Mutations Implicated in Altered Persistence. J. Bacteriol. 193:3598-3605 (2011).
12. Dorr T, Vulić M, & Lewis K Ciprofloxacin causes persister formation by inducing the TisB toxin in *Escherichia coli*. PLoS Biol. 8:e1000317 (2010).
13. Harrison J J, et al. The chromosomal toxin gene yafQ is a determinant of multidrug tolerance for *Escherichia coli* growing in a biofilm. Antimicrob. Agents Chemother. 53:2253-2258 (2009).
14. Chowdhury N, Kwan B W, & Wood T K Persistence Increases in the Absence of the Alarmone Guanosine Tetraphosphate by Reducing Cell Growth. Scientific Reports 6:20519 (2016).
15. Kim J-S, Chowdhury N, Yamasaki R, & Wood T K Viable But Non-Culturable and Persistence Describe the Same Bacterial Stress State. Environ Microbiol 20:2038-2048 (2018).
16. Song S & Wood T K ppGpp Ribosome Dimerization Model for Bacterial Persister Formation and Resuscitation. bioRxiv: 663658 (2019).
17. Wood T K, Song S, & Yamasaki R Ribosome dependence of persister cell formation and resuscitation. J. Microbiol. 57:DOI 10.1007/s12275-12019-18629-12272 (2019).
18. Cheverton Angela M, et al. A Salmonella Toxin Promotes Persister Formation through Acetylation of tRNA. Mol. Cell 63:86-96 (2016).
19. Kim J-S, Yamasaki R, Song S, Zhang W, & Wood T K Single Cell Observations Show Persister Cells Wake Based on Ribosome Content. Environ. Microbiol. 20:2085-2098 (2018).
20. Yamasaki R, Song S, Benedik M J, & Wood T K Persister Cells Resuscitate Using Membrane Sensors that Activate Chemotaxis, Lower cAMP Levels, and Revive Ribosomes. bioRxiv doi 10.1101/486985:486985 (2019).
21. Aizenman E, Engelberg-Kulka H, & Glaser G An *Escherichia coli* chromosomal "addiction module" regulated by guanosine 3',5'-bispyrophosphate: a model for programmed bacterial cell death. Proc Natl Acad Sci USA 93:6059-6063 (1996).
22. Bertani G Studies on Lysogenesis 0.1. The Mode of Phage Liberation by Lysogenic *Escherichia-Coli*. J. Bacteriol. 62:293-300 (1951).
23. Kwan B W, Valenta J A, Benedik M J, & Wood T K Arrested protein synthesis increases persister-like cell formation. Antimicrob. Agents Chemother. 57:1468-1473 (2013).
24. Rodriguez R L & Tait R C (1983) Recombinant DNA Techniques: An Introduction (Benjamin/Cummings Publishing, Menlo Park, Calif.).
25. Kitagawa M, et al. Complete set of ORF clones of *Escherichia coli* ASKA library (a complete set of *E. coli*

K-12 ORF archive): unique resources for biological research. DNA Res 12:291-299 (2005).
26. Shah D, et al. Persisters: a distinct physiological state of *E. coli*. BMC Microbiol 6:53 (2006).
27. Song S, Gong T, Yamasaki R, Kim J-S. & Wood T K Identification of a Potent Indigoid Persister Antimicrobial by Screening Dormant Cells. Biotechnol. Bioengr. https://doi.org/10.1002/bit.27078 (2019).
28. Cui P, et al. Identification of Genes Involved in Bacteriostatic Antibiotic-Induced Persister Formation. Front Microbiol 9:413 (2018).
29. Grassi L, et al. Generation of Persister Cells of *Pseudomonas aeruginosa* and *Staphylococcus aureus* by Chemical Treatment and Evaluation of Their Susceptibility to Membrane-Targeting Agents. Front Microbiol 8:1917 (2017).
30. Narayanaswamy V P, et al. Novel Glycopolymer Eradicates Antibiotic- and CCCP-Induced Persister Cells in *Pseudomonas aeruginosa*. Front Microbiol 9:1724 (2018).
31. Pu Y, et al. ATP-Dependent Dynamic Protein Aggregation Regulates Bacterial Dormancy Depth Critical for Antibiotic Tolerance. Molecular Cell 73:1-14 (2019).
32. Sulaiman J E, Hao C, & Lam H Specific Enrichment and Proteomics Analysis of *Escherichia coli* Persisters from Rifampin Pretreatment. J Proteome Res 17:3984-3996 (2018).
33. Tkhilaishvili T, Lombardi L, Klatt A-B, Trampuz A, & Di Luca M Bacteriophage Sb-1 enhances antibiotic activity against biofilm, degrades exopolysaccharide matrix and targets persisters of *Staphylococcus aureus*. Int J Antimicrob Agents 52:842-853 (2018).
34. Gutgsell N S, Deutsher M P, & Ofengand J The pseudouridine synthase RluD is required for normal ribosome assembly and function in *Escherichia coli*. RNA 11:1141-1152 (2005).
35. Burger K, et al. Chemotherapeutic Drugs Inhibit Ribosome Biogenesis at Various Levels. J Biol Chem 285: 12416-12425 (2010).
36. Lu T, Stroot P G, & Oerther D B Reverse Transcription of 16S rRNA To Monitor Ribosome-Synthesizing Bacterial Populations in the Environment. Appl Environ Microb 75:4589-4598 (2009).
37. Piques M, et al. Ribosome and transcript copy numbers, polysome occupancy and enzyme dynamics in *Arabidopsis*. Mol Syst Biol 5:314 (2009).
38. Gogol E B, Rhodius V A, Papenfort K, Vogel J, & Gross C A Small RNAs endow a transcriptional activator with essential repressor functions for single-tier control of a global stress regulon. Proc. Natl. Acad. Sci. U.S.A.: 201109379 (2011).
39. Baba T, et al. Construction of *Escherichia coli* K-12 in-frame, single-gene knockout mutants: the Keio collection. Mol. Syst. Biol. 2:2006 0008 (2006).
40. Guyer M S, Reed R R, Steitz J A, & Low K B Identification of a sex-factor-affinity site in *E. coli* as gamma delta. Cold Spring Harbor symposia on quantitative biology 45 Pt 1:135-140 (1981).
41. Hobbs E C, Astarita J L, & Storz G Small RNAs and Small Proteins Involved in Resistance to Cell Envelope Stress and Acid Shock in *Escherichia coli*: Analysis of a Bar-Coded Mutant Collection. J. Bacteriol. 192:59-67 (2010).

In the foregoing description, it will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A method for killing bacterial persister cells and/or dormant "viable but non-culturable" (VBNC) cells in a bacterial population, the method comprising administering to the bacterial population an effective amount of [(5-nitro-3-phenyl-1H-indol-2-yl)methyl]amine having the formula:

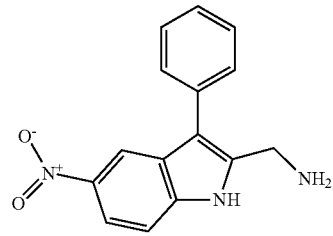 [SMILES: NCc1[nH]c2ccc([N+](=O)[O-])cc2c1-c1ccccc1]

or a salt thereof, [(5-nitro-3-phenyl-1H-indol-2-yl)methyl]amine hydrochloride (NPIMA), having the formula:

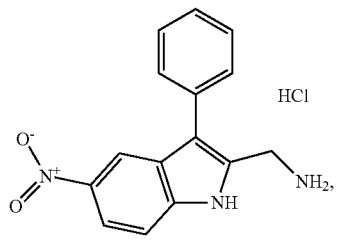 [SMILES: NCc1[nH]c2ccc([N+](=O)[O-])cc2c1-c1ccccc1 ; Cl]

and wherein the bacterial persister cells and/or VBNC comprise bacteria selected from *Escherichia* spp., *Staphylococcus* spp., and *Pseudomonas* spp.

2. The method of claim 1, wherein the bacterial persister cells and/or VBNC cells are resistant to one or more antibiotics which do not comprise any compound of [5-nitro-3-phenyl-1H-indol-2-yl)methyl]amine hydrochloride, 2-({2-[4-chlorophenyl)amino]4-quinazolinyl}amino) ethanol hydrochloride, 1-[2-(4-chlorophenoxy)-2-methylpropanoyl]-4-methylpiperazine, N-benzyl-N-{[3-(4-methoxyphenyl)-1-phenyl-1H-pyrazol-4-yl]methyl}acetamide, N-(3,4-dichlorophenyl)-N'-(3-fluorophenyl)thiourea, 2-({2-[(4-bromophenyl)amino]-4-quinazolinyl}amino)ethanol hydrochloride, N-2-(4-ethoxyphenyl)-2,4-quinazolinediamine hydrochloride, 4-{[(5-nitro-2-thienyl)methylene]amino}benzamide, 2-[(6-phenyl-2,3,4,9-tetrahydro-1H-carbazol-1-yl)amino]ethanol, 2-bromo-4-chlorophenyl phenylcarbamate, 1-(3,6-dichloro-9H-carbazol-9-yl)-3-(2-methyl-1H-imidazol-1-yl)-2-propanol, N-(3-chloro-4-fluorophenyl)-N'-[2-(difluoromethoxy)phenyl]thiourea, 2-(butyryloxy)-1H-benzo[de]isoquinoline-1,3(2H)-dione, N-phenyl-N'-[(1-phenylcyclopentyl)methyl]thiourea, N-[2-(4-fluorophenyl)ethyl]-N'-(4-nitrophenyl)thiourea, 2,4-dichloro-5-(5-nitro-2-furyl)benzoic acid, N-(3-chlorophenyl)-N'-[3-(trifluoromethyl)phenyl]thiourea, N-(3-chloro-4-fluorophenyl)-N'-(2-methoxy-4-nitrophenyl)thiourea, 4-({[3-chloro-4-fluorophenyl]amino}carbonothioyl)amino-N-ethylbenzenesulfonamide, 2-[({2-[(2-chlorobenzyl)oxy]-1-naphthyl}methyl)amino]ethanol hydrochloride, 17-(4-bromophenyl)-17-azapentacyclononadeca-2,4,6,9,11,13-hexaene-16,18-dione, N-(3-chloro-4-fluorophenyl)-N'-3-pyridinylthiourea, N-(4-chlorobenzyl)-N'-4-pyridinylthiourea, 5-bromo-N-{2-[(4-methylphenyl)thio]ethyl}-2-thiophenesulfonamide, N'-(3,5-dichloro-2-hydroxybenzylidene)-2-oxo-4-phenyl-3-pyrrolidinecarbohydrazide, 2-{[2-(4-bromophenyl)-2-oxoethyl]thio}-3-ethyl-5,6,7,8-tetrahydro[1]benzothieno[2,3-d]pyrimidin-4(3H)-one, methyl 5-[(dimethylamino)carbonyl]-4-methyl-2-({[(1-methyl-1H-pyrazol-3-yl)amino]carbonothioyl}amino)-3-thiophenecarboxylate, N-[2-(3,4-dimethoxyphenyl)ethyl]N'-[1-(pentafluorobenzyl)-1H-pyrazol-3-yl]thiourea, 4-chloro-N-(6,7-dimethoxy-4-oxo-1,4-dihydro-2-quinazolinyl)benzamide, (4-methoxyphenyl)(phenyl) methanone, N-(3-acetylphenyl)-4,5-dimethyl-2-furamide, 6-(4-iodophenyl)-2-methylimidazo[2,1-b][1,3]thiazole, N-{[(4-bromophenyl)amino]carbonothioyl}-2,2-dimethylpropanamide, 1-(2,4-dichlorobenzoyl)-2,3-dihydro-1Himidazo[1,2-a]benzimidazole, 3-(3-chlorophenyl)-5,5-dimethyl-4-methylene-1,3-oxazolidin-2-one, 2-methyl-4-[4-(methylthio)phenyl-5-oxo-N-phenyl-1,4,5,6,7,8-hexahydro-3-guinolinecarboxamide, 4-(isopropoxycarbonyl)benzyl 2-pyrazinecarboxylate, N-[4-(2-oxo-1-pyrrolidinyl)phenyl]-1H-1,2,4-triazole-3-carboxamide, 4-chloro-N-(4-oxo-1,4-dihydro-2-quinazolinyl)benzamide, 3-hydroxy-5-(4-propoxyphenyl)-1-(3-pyridinylmethyl)-4-(2-thienylcarbonyl)-1,5-dihydro-2H-pyrrol-2-one, 4-(3,4-dimethoxyphenyl)-2-hydrazino-6-phenylpyrimidine, N'-[1-(3,4-dimethoxyphenyl)ethylidene]-3-phenyl-1Hpyrazole-5-carbohydrazide, 3-[4-(4-chlorophenyl)-1-piperazinyl]-1-(4-iodophenyl)-2,5-pyrrolidinedione, N-(3-oxo-1,3-dihydro-2-benzofuran-5-yl)-1H-1,2,4-triazole-3-carboxamide, 3-[(5-methyl-2-furoyl)amino]benzoic acid, N-(4-{[(2,4-dimethoxyphenyl)amino]sulfonyl}phenyl)-3-[(4-methylphenyl)thio]propenamide, N~2~-(3-fluorophenyl)N~2~-(methylsulfonyl)N~1~-[2-(1-pyrrolidinylcarbonyl)phenyl]glycinamide, N-(5-chloro-2-methoxyphenyl)-N'-(1-ethyl-3,5-dimethyl-1Hpyrazol-4-yl)thiourea, 1-[(4-methylphenyl)sulfonyl]N-1 3-thiazol-2-ylprolinamide, 2,5-dichloro-N-(2-furylmethyl)benzamide, 3-{[(2-methoxyphenyl)amino]methyl}-5-[4-(methylthio)benzylidene]-1,3-thiazolidine-2,4-dione, 5-(4-propoxybenzyl)-1H-tetrazole or a salt or non-salt form thereof.

3. The method of claim 1, wherein the bacterial persister cells and/or VBNC cells comprise *Escherichia* spp.

4. The method of claim 1, wherein the bacterial persister cells and/or VBNC cells comprise *Staphylococcus* spp.

5. The method of claim 1, wherein the bacterial persister cells and/or VBNC cells comprise *Pseudomonas* spp.

6. The method of claim 1, wherein the bacterial persister cells and/or VBNC cells comprise *E. coli*.

7. The method of claim 1, wherein the bacterial persister cells and/or VBNC cells comprise *S. aureus*.

8. The method of claim 1, wherein the bacterial persister cells and/or VBNC cells comprise *P. aeruginosa*.

9. The method of claim 1, wherein the bacterial persister cells and/or VBNC cells are present in anaerobic conditions.

10. The method of claim 1, wherein the bacterial population is present in a biofilm.

11. The method of claim 1, wherein the bacterial population is present in a biofilm and the bacterial persister cells and/or VBNC cells are reduced, but the biofilm is not dispersed.

12. The method of claim 1, wherein the bacterial population is present in an infection in a wound of an individual, and/or wherein the bacterial population is present in a liquid biological sample or liquid environment.

13. The method of claim 1, wherein the population comprises an infection in an individual, wherein the individual has been previously diagnosed with a bacterial infection and has been treated with at least one antibiotic which does not comprise any compound of [5-nitro-3-phenyl-1H-indol-2-yl)methyl]amine hydrochloride, 2-({2-[4-chlorophenyl)amino]4-quinazolinyl}amino) ethanol hydrochloride, 1-[2-(4-chlorophenoxy)-2-methylpropanoyl]-4-methylpiperazine, N-benzyl-N-{[3-(4-methoxyphenyl)-1-phenyl-1H-pyrazol-4-yl]methyl}acetamide, N-(3,4-dichlorophenyl)-N'-(3-fluorophenyl)thiourea, 2-({2-[(4-bromophenyl)amino]-4-quinazolinyl}amino)ethanol hydrochloride, N-2-(4-ethoxyphenyl)-2,4-quinazolinediamine hydrochloride, 4-{[(5-nitro-2-thienyl)methylene]amino}benzamide, 2-[(6-phenyl-2,3,4,9-tetrahydro-1H-carbazol-1-yl)amino]ethanol, 2-bromo-4-chlorophenyl phenylcarbamate, 1-(3,6-dichloro-9H-carbazol-9-yl)-3-(2-methyl-1H-imidazol-1-yl)-2-propanol, N-(3-chloro-4-fluorophenyl)-N'-[2-(difluoromethoxy)phenyl]thiourea, 2-(butyryloxy)-1H-benzo[de]isoquinoline-1,3(2H)-dione, N-phenyl-N'-[(1-phenylcyclopentyl)methyl]thiourea, N-[2-(4-fluorophenyl)ethyl]-N'-(4-nitrophenyl)thiourea, 2,4-dichloro-5-(5-nitro-2-furyl)benzoic acid, N-(3-chlorophenyl)-N'-[3-(trifluoromethyl)phenyl]thiourea, N-(3-chloro-4-fluorophenyl)-N'-(2-methoxy-4-nitrophenyl)thiourea, 4-({[3-chloro-4-fluorophenyl]amino}carbonothioyl)amino-N-ethylbenzenesulfonamide, 2-[({2-[(2-chlorobenzyl)oxy]-1-naphthyl}methyl)amino]ethanol hydrochloride, 17-(4-bromophenyl)-17-azapentacyclononadeca-2,4,6,9,11,13-hexaene-16,18-dione, N-(3-chloro-4-fluorophenyl)-N'-3-pyridinylthiourea, N-(4-chlorobenzyl)-N'-4-pyridinylthiourea, 5-bromo-N-{2-[(4-methylphenyl)thio]ethyl}-2-thiophenesulfonamide, N'-(3,5-dichloro-2-hydroxybenzylidene)-2-oxo-4-phenyl-3-pyrrolidinecarbohydrazide, 2-{[2-(4-bromophenyl)-2-oxoethyl]thio}-3-ethyl-5,6,7,8-tetrahydro[1]benzothieno[2,3-d]pyrimidin-4(3H)-one, methyl 5-[(dimethylamino)carbonyl]-4-methyl-2-({[(1-methyl-1H-pyrazol-3-yl)amino]carbonothioyl}amino)-3-thiophenecarboxylate, N-[2-(3,4-dimethoxyphenyl)ethyl]N'-[1-(pentafluorobenzyl)-1H-pyrazol-3-yl]thiourea, 4-chloro-N-(6,7-dimethoxy-4-oxo-1,4-dihydro-2-quinazolinyl)benzamide, (4-methoxyphenyl)(phenyl) methanone, N-(3-acetylphenyl)-4,5-dimethyl-2-furamide, 6-(4-iodophenyl)-2-methylimidazo[2,1-b][1,3]thiazole, N-{[(4-bromophenyl)amino]

carbonothioyl}-2,2-dimethylpropanamide, 1-(2,4-dichlorobenzoyl)-2,3-dihydro-1Himidazo[1,2-a]benzimidazole, 3-(3-chlorophenyl)-5,5-dimethyl-4-methylene-1,3-oxazolidin-2-one, 2-methyl-4-[4-(methylthio)phenyl]-5-oxo-N-phenyl-1,4,5,6,7,8-hexahydro-3-quinolinecarboxamide, 4-(isopropoxycarbonyl)benzyl 2-pyrazinecarboxylate, N-[4-(2-oxo-1-pyrrolidinyl)phenyl]-1H-1,2,4-triazole-3-carboxamide, 4-chloro-N-(4-oxo-1,4-dihydro-2-quinazolinyl)benzamide, 3-hydroxy-5-(4-propoxyphenyl)-1-(3-pyridinylmethyl)-4-(2-thienylcarbonyl)-1,5-dihydro-2H-pyrrol-2-one, 4-(3,4-dimethoxyphenyl)-2-hydrazino-6-phenylpyrimidine, N'-[1-(3,4-dimethoxyphenyl)ethylidene]-3-phenyl-1Hpyrazole-5-carbohydrazide, 3-[4-(4-chlorophenyl)-1-piperazinyl]-1-(4-iodophenyl)-2,5-pyrrolidinedione, N-(3-oxo-1,3-dihydro-2-benzofuran-5-yl)-1H-1,2,4-triazole-3-carboxamide, 3-[(5-methyl-2-furoyl)amino]benzoic acid, N-(4-{[(2,4-dimethoxyphenyl)amino]sulfonyl}phenyl)-3-[(4-methylphenyl)thio]propenamide, N~2~-(3-fluorophenyl)N~2~-(methylsulfonyl)N~1~-[2-(1-pyrrolidinylcarbonyl)phenyl]glycinamide, N-(5-chloro-2-methoxyphenyl)-N'-(1-ethyl-3,5-dimethyl-1Hpyrazol-4-yl)thiourea, 1-[(4-methylphenyl)sulfonyl]N-1 3-thiazol-2-ylprolinamide, 2,5-dichloro-N-(2-furylmethyl)benzamide, 3-{[(2-methoxyphenyl)amino]methyl}-5-[4-(methylthio)benzylidene]-1,3-thiazolidine-2,4-dione, 5-(4-propoxybenzyl)-1H-tetrazole or a salt or non-salt form thereof.

14. The method of claim 1, further comprising administering to the bacterial population an antibiotic which does not comprise any compound of [5-nitro-3-phenyl-1H-indol-2-yl)methyl]amine hydrochloride, 2-({2-[4-chlorophenyl)amino]4-quinazolinyl}amino) ethanol hydrochloride, 1-[2-(4-chlorophenoxy)-2-methylpropanoyl]-4-methylpiperazine, N-benzyl-N-{[3-(4-methoxyphenyl)-1-phenyl-1H-pyrazol-4-yl]methyl}acetamide, N-(3,4-dichlorophenyl)-N'-(3-fluorophenyl)thiourea, 2-({2-[(4-bromophenyl)aminol-4-quinazolinyl}amino)ethanol hydrochloride, N-2-(4-ethoxyphenyl)-2,4-quinazolinediamine hydrochloride, 4-{[(5-nitro-2-thienyl)methylene]amino}benzamide, 2-[(6-phenyl-2,3,4,9-tetrahydro-1H-carbazol-1-yl)amino]ethanol, 2-bromo-4-chlorophenyl phenylcarbamate, 1-(3,6-dichloro-9H-carbazol-9-yl)-3-(2-methyl-1H-imidazol-1-yl)-2-propanol, N-(3-chloro-4-fluorophenyl)-N'-[2-(difluoromethoxy)phenyl]thiourea, 2-(butyryloxy)-1H-benzo[de]isoquinoline-1,3(2H)-dione, N-phenyl-N'-[(1-phenylcyclopentyl)methyl]thiourea, N-[2-(4-fluorophenyl)ethyl]-N'-(4-nitrophenyl)thiourea, 2,4-dichloro-5-(5-nitro-2-furyl)benzoic acid, N-(3-chlorophenyl)-N'-[3-(trifluoromethyl)phenyl]thiourea, N-(3-chloro-4-fluorophenyl)-N'-(2-methoxy-4-nitrophenyl)thiourea, 4-({[3-chloro-4-fluorophenyl]amino}carbonothioyl)amino-N-ethylbenzenesulfonamide, 2-[({2-[(2-chlorobenzyl)oxy]-1-naphthyl}methyl)amino]ethanol hydrochloride, 17-(4-bromophenyl)-17-azapentacyclononadeca-2,4,6,9,11,13-hexaene-16,18-dione, N-(3-chloro-4-fluorophenyl)-N'-3-pyridinylthiourea, N-(4-chlorobenzyl)-N'-4-pyridinylthiourea, 5-bromo-N-{2-[(4-methylphenyl)thio]ethyl}-2-thiophenesulfonamide, N'-(3,5-dichloro-2-hydroxybenzylidene)-2-oxo-4-phenyl-3-pyrrolidinecarbohydrazide, 2-{[2-(4-bromophenyl)-2-oxoethyl]thio}-3-ethyl-5,6,7,8-tetrahydro[1]benzothieno[2,3-d]pyrimidin-4(3H)-one, methyl 5-[(dimethylamino)carbonyl]-4-methyl-2-({[(1-methyl-1H-pyrazol-3-yl)amino]carbonothioyl}amino)-3-thiophenecarboxylate, N-[2-(3,4-dimethoxyphenyl)ethyl]N'-[1-(pentafluorobenzyl)-1H-pyrazol-3-yl]thiourea, 4-chloro-N-(6,7-dimethoxy-4-oxo-1,4-dihydro-2-quinazolinyl)benzamide, (4-methoxyphenyl)(phenyl) methanone, N-(3-acetylphenyl)-4,5-dimethyl-2-furamide, 6-(4-iodophenyl)-2-methylimidazo[2,1-b][1,3]thiazole N-{[(4-bromophenyl)amino]carbonothioyl}-2,2-dimethylpropanamide, 1-(2,4-dichlorobenzoyl)-2,3-dihydro-1Himidazo[1,2-a]benzimidazole, 3-(3-chlorophenyl)-5,5-dimethyl-4-methylene-1,3-oxazolidin-2-one, 2-methyl-4-[4-(methylthio)phenyl]-5-oxo-N-phenyl-1,4,5,6,7,8-hexahydro-3-quinolinecarboxamide, 4-(isopropoxycarbonyl)benzyl 2-pyrazinecarboxylate, N-[4-(2-oxo-1-pyrrolidinyl)phenyl]-1H-1,2,4-triazole-3-carboxamide, 4-chloro-N-(4-oxo-1,4-dihydro-2-quinazolinyl)benzamide, 3-hydroxy-5-(4-propoxyphenyl)-1-(3-pyridinylmethyl)-4-(2-thienylcarbonyl)-1,5-dihydro-2H-pyrrol-2-one, 4-(3,4-dimethoxyphenyl)-2-hydrazino-6-phenylpyrimidine, N'-[1-(3,4-dimethoxyphenyl)ethylidene]-3-phenyl-1Hpyrazole-5-carbohydrazide, 3-[4-(4-chlorophenyl)-1-piperazinyl]-1-(4-iodophenyl)-2,5-pyrrolidinedione, N-(3-oxo-1,3-dihydro-2-benzofuran-5-yl)-1H-1,2,4-triazole-3-carboxamide, 3-[(5-methyl-2-furoyl)amino]benzoic acid, N-(4-{[(2,4-dimethoxyphenyl)amino]sulfonyl}phenyl)-3-[(4-methylphenyl)thio]propenamide, N~2~-(3-fluorophenyl)N~2~-(methylsulfonyl)N~1~-[2-(1-pyrrolidinylcarbonyl)phenyl]glycinamide, N-(5-chloro-2-methoxyphenyl)-N'-(1-ethyl-3,5-dimethyl-1Hpyrazol-4-yl)thiourea, 1-[(4-methylphenyl)sulfonyl]N-1 3-thiazol-2-ylprolinamide, 2,5-dichloro-N-(2-furylmethyl)benzamide, 3-{[(2-methoxyphenyl)amino]methyl}-5-[4-(methylthio)benzylidene]-1,3-thiazolidine-2,4-dione, 5-(4-propoxybenzyl)-1H-tetrazole or a salt or non-salt form thereof.

15. The method of claim 1, wherein the bacterial persister cells and/or VBNC cells are reduced in the bacterial population.

16. The method of claim 1, wherein a reduction in the bacterial persister cells and/or the VBNC cells in the population occurs after the compound is administered to the population.

17. The method of claim 16, wherein the reduction of the persister cells and/or the VBNC cells is greater than a reference, wherein the reference comprises a value obtained from reducing persister cells and/or or reducing VBNC cells of the same bacterial species using a corresponding amount of an antibiotic which does not comprise any compound of [5-nitro-3-phenyl-1H-indol-2-yl)methyl]amine hydrochloride, 2-({2-[4-chlorophenyl)amino]4-quinazolinyl}amino) ethanol hydrochloride, 1-[2-(4-chlorophenoxy)-2-methylpropanoyl]-4-methylpiperazine, N-benzyl-N-{[3-(4-methoxyphenyl)-1-phenyl-1H-pyrazol-4-yl]methyl}acetamide, N-(3,4-dichlorophenyl)-N'-(3-fluorophenyl)thiourea, 2-({2-[(4-bromophenyl)amino]-4-quinazolinyl}amino)ethanol hydrochloride, N-2-(4-ethoxyphenyl)-2,4-quinazolinediamine hydrochloride, 4-{[(5-nitro-2-thienyl)methylene]amino}benzamide, 2-[(6-phenyl-2,3,4,9-tetrahydro-1H-carbazol-1-yl)amino]ethanol, 2-bromo-4-chlorophenyl phenylcarbamate, 1-(3,6-dichloro-9H-carbazol-9-yl)-3-(2-methyl-1H-imidazol-1-yl)-2-propanol, N-(3-chloro-4-fluorophenyl)-N'-[2-(difluoromethoxy)phenyl]thiourea, 2-(butyryloxy)-1H-benzo[de]isoquinoline-1,3(2H)-dione, N-phenyl-N'-[(1-phenylcyclopentyl)methyl]thiourea, N-[2-(4-fluorophenyl)ethyl]-N'-(4-nitrophenyl)thiourea, 2,4-dichloro-5-(5-nitro-2-furyl)benzoic acid, N-(3-chlorophenyl)-N'-[3-(trifluoromethyl)phenyl]thiourea, N-(3-chloro-4-fluorophenyl)-N'-(2-methoxy-4-nitrophenyl)thiourea, 4-({[3-chloro-4-fluorophenyl]amino}carbonothioyl)amino-N-ethylbenzenesulfonamide, 2-[({2-[(2-chlorobenzyl)oxy]-1-naphthyl}methyl)amino] ethanol hydrochloride, 17-(4-bromophenyl)-17-azapentacyclononadeca-2,4,6,9,11,13-hexaene-16,18-dione, N-(3-chloro-4-fluorophenyl)-N'-3-pyridinylthiourea, N-(4-chlorobenzyl)-N'-4-pyridinylthiourea, 5-bromo-N-{2-[(4-methylphenyl)thio]ethyl}-2-thiophenesulfonamide, N'-(3,5-dichloro-2-hydroxybenzylidene)-2-oxo-4-phenyl-3-pyrrolidinecarbohydrazide, 2-{[2-(4-bromophenyl)-2-oxoethyl]thio}-3-ethyl-5,6,7,8-tetrahydro[1]benzothieno[2,3-d]pyrimidin-4(3H)-one, methyl 5-[(dimethylamino) carbonyl]-4-methyl-2-({[(1-methyl-1H-pyrazol-3-yl)amino]carbonothioyl}amino)-3-thiophenecarboxylate, N-[2-(3,4-dimethoxyphenyl)ethyl]N'-[1-(pentafluorobenzyl)-1H-pyrazol-3-yl]thiourea, 4-chloro-N-(6,7-dimethoxy-4-oxo-1,4-dihydro-2-quinazolinyl)benzamide, (4-methoxyphenyl)(phenyl) methanone, N-(3-acetylphenyl)-4,5-dimethyl-2-furamide, 6-(4-iodophenyl)-2-methylimidazo[2,1-b][1,3]thiazole, N-{[(4-bromophenyl)amino] carbonothioyl}-2,2-dimethylpropanamide, 1-(2,4-dichlorobenzoyl)-2,3-dihydro-1Himidazo[1,2-a] benzimidazole, 3-(3-chlorophenyl)-5,5-dimethyl-4-methylene-1,3-oxazolidin-2-one, 2-methyl-4-[4-(methylthio)phenyl]-5-oxo-N-phenyl-1,4,5,6,7,8-hexahydro-3-quinolinecarboxamide, 4-(isopropoxycarbonyl)benzyl 2-pyrazinecarboxylate, N-[4-(2-oxo-1-pyrrolidinyl)phenyl]-1H-1,2,4-triazole-3-carboxamide, 4-chloro-N-(4-oxo-1,4-dihydro-2-quinazolinyl)benzamide, 3-hydroxy-5-(4-propoxyphenyl)-1-(3-pyridinylmethyl)-4-(2-thienylcarbonyl)-1,5-dihydro-2H-pyrrol-2-one, 4-(3,4-dimethoxyphenyl)-2-hydrazino-6-phenylpyrimidine, N'-[1-(3,4-dimethoxyphenyl)ethylidene]-3-phenyl-1Hpyrazole-5-carbohydrazide, 3-[4-(4-chlorophenyl)-1-piperazinyl]-1-(4-iodophenyl)-2,5-pyrrolidinedione, N-(3-oxo-1,3-dihydro-2-benzofuran-5-yl)-1H-1,2,4-triazole-3-carboxamide, 3-[(5-methyl-2-furoyl)amino]benzoic acid, N-(4-{[(2,4-dimethoxyphenyl)amino]sulfonyl}phenyl)-3-[(4-methylphenyl)thio]propenamide, N~2~-(3-fluorophenyl)N~2~-(methylsulfonyl)N~1~-[2-(1-pyrrolidinylcarbonyl phenyl]glycinamide, N-(5-chloro-2-methoxyphenyl)-N'-(1-ethyl-3,5-dimethyl-1Hpyrazol-4-yl)thiourea, 1-[(4-methylphenyl)sulfonyl]N-1 3-thiazol-2-ylprolinamide, 2,5-dichloro-N-(2-furylmethyl)benzamide, 3-{[(2-methoxyphenyl)amino]methyl}-5-[4-(methylthio)benzylidene]-1,3-thiazolidine-2,4-dione, 5-(4-propoxybenzyl)-1H-tetrazole.

* * * * *

UNITED STATES PATENT AND TRADEMARK OFFICE
CERTIFICATE OF CORRECTION

PATENT NO. : 11,654,146 B2
APPLICATION NO. : 17/337097
DATED : May 23, 2023
INVENTOR(S) : Thomas Keith Wood et al.

It is certified that error appears in the above-identified patent and that said Letters Patent is hereby corrected as shown below:

In the Specification

Column 16, Line 49, "5 mm" should be --5 min--.

Column 28, Line 53, "Iu" should be --Hu--.

Column 32, Line 47, "10.000" should be --10,000--.

Column 32, Line 52, "L. coli" should be --E. coli--.

Column 32, Line 58, "rhuD" should be --rluD--.

Column 34, Table 3, Line 7, "$\Delta$rhD Km$^R$" should be --$\Delta$rluD Km$^R$--.

Column 34, Table 3, Line 12, "pC7A24N" should be --pCA24N--.

Column 34, Table 3, Line 13, "$P_{T5-Inc}$" should be --$P_{T5-Iac}$--.

Column 34, Line 66, "F. coli" should be --E. coli--.

Column 37, 4$^{th}$ Name, 2$^{nd}$ Line, "1H" should be --1h--.

Column 37, 6$^{th}$ Name, 1$^{st}$ Line, "methyl-4-[4" should be --methyl-4-(4--.

Column 37, 6$^{th}$ Name, 2$^{nd}$ Line, "phenyl]-5" should be --phenyl)-5--.

Column 44, Lines 37-38, "acctyltransferase" should be --acetyltransferase--.

Signed and Sealed this
Eighth Day of August, 2023

Katherine Kelly Vidal
*Director of the United States Patent and Trademark Office*

CERTIFICATE OF CORRECTION (continued)
U.S. Pat. No. 11,654,146 B2

In the Claims

Column 49, Claim 2, Line 42, "phenyl-5-oxo" should be --phenyl]-5-oxo--.

Column 51, Claim 14, Line 38, "aminol-4-quinazolinyl" should be --amino]-4-quinazolinyl--.